US012777844B2

(12) United States Patent
Song et al.

(10) Patent No.: US 12,777,844 B2
(45) Date of Patent: Oct. 27, 2026

(54) LIGHT EMITTING DEVICE AND LIGHT EMITTING DISPLAY DEVICE INCLUDING THE SAME

(71) Applicant: LG Display Co., Ltd., Seoul (KR)

(72) Inventors: Wook Song, Paju-si (KR); Sae Mi Park, Paju-si (KR); Myeong Seon Cho, Paju-si (KR); Min Hyeong Hwang, Paju-si (KR); Chun Ki Kim, Paju-si (KR); Jung Keun Kim, Paju-si (KR); Byung Soo Kim, Paju-si (KR); Young Jun Yu, Paju-si (KR); Sang Beom Kim, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 958 days.

(21) Appl. No.: 18/078,731

(22) Filed: Dec. 9, 2022

(65) Prior Publication Data

US 2023/0217821 A1 Jul. 6, 2023

(30) Foreign Application Priority Data

Dec. 31, 2021 (KR) ........................ 10-2021-0194800
Jan. 1, 2022 (KR) ........................ 10-2022-0000005

(51) Int. Cl.

| | |
|---|---|
| ***H10K 85/60*** | (2023.01) |
| ***C07C 211/61*** | (2006.01) |
| ***C07D 235/08*** | (2006.01) |
| ***C07D 235/18*** | (2006.01) |
| ***C07D 401/14*** | (2006.01) |
| ***C09K 11/06*** | (2006.01) |
| ***H10K 50/13*** | (2023.01) |
| *H10K 50/11* | (2023.01) |
| *H10K 50/16* | (2023.01) |
| *H10K 50/17* | (2023.01) |
| *H10K 50/18* | (2023.01) |
| *H10K 50/19* | (2023.01) |
| *H10K 59/12* | (2023.01) |
| *H10K 101/10* | (2023.01) |
| *H10K 102/00* | (2023.01) |

(52) U.S. Cl.

CPC ........ *H10K 85/6572* (2023.02); *C07C 211/61* (2013.01); *C07D 235/08* (2013.01); *C07D 235/18* (2013.01); *C07D 401/14* (2013.01); *C09K 11/06* (2013.01); *H10K 50/13* (2023.02); *H10K 85/60* (2023.02); *H10K 85/615* (2023.02); *H10K 85/626* (2023.02); *H10K 85/633* (2023.02); *H10K 85/654* (2023.02); *C07B 2200/05* (2013.01); *C07C 2603/18* (2017.05); *C07C 2603/97* (2017.05); *C09K 2211/1007* (2013.01); *C09K 2211/1011* (2013.01); *C09K 2211/1014* (2013.01); *C09K 2211/1018* (2013.01); *H10K 50/11* (2023.02); *H10K 50/16* (2023.02); *H10K 50/171* (2023.02); *H10K 50/18* (2023.02); *H10K 50/19* (2023.02); *H10K 59/12* (2023.02); *H10K 85/624* (2023.02); *H10K 2101/10* (2023.02); *H10K 2102/351* (2023.02)

(58) Field of Classification Search

CPC ............................. H01K 50/13; C07D 403/00
See application file for complete search history.

(56) References Cited

U.S. PATENT DOCUMENTS

| | | | |
|---|---|---|---|
| 9,391,281 | B2 | 7/2016 | Lee et al. |
| 9,412,954 | B2 | 8/2016 | Lee et al. |
| 9,882,146 | B2 | 1/2018 | Lee et al. |
| 11,239,427 | B2 | 2/2022 | Lee et al. |
| 11,476,425 | B2 | 10/2022 | Oh et al. |
| 2006/0240277 | A1 | 10/2006 | Hatwar et al. |
| 2011/0073844 | A1 | 3/2011 | Pieh et al. |
| 2014/0299192 | A1 | 10/2014 | Lee et al. |
| 2015/0162543 | A1 | 6/2015 | Lee et al. |
| 2016/0218298 | A1 | 7/2016 | Lee et al. |

(Continued)

FOREIGN PATENT DOCUMENTS

| | | | |
|---|---|---|---|
| CN | 102034934 | A | 4/2011 |
| CN | 108473394 | A | 8/2018 |

(Continued)

OTHER PUBLICATIONS

Chen, J. et al. "Hybrid White OLEDs with Fluorophors and Phosphors." Materials Today, vol. 17, No. 4, May 2014, pp. 175-183.
European Patent Office, Extended European Search Report, European Patent Application No. 22215494.0, May 31, 2023, 11 pages.
European Patent Office, Extended European Search Report, European Patent Application No. 22216748.8, May 30, 2023, nine pages.
Miao, Y. et al. "High-Efficiency/CRI/Color Stability Warm White Organic Light-Emitting Diodes by Incorporating Ultrathin Phosphorescence Layers in a Blue Fluorescence Layer." Nanophotonics, vol. 7, No. 1, Jan. 2018, pp. 295-304.
Intellectual Property India, Examination Report, Indian Patent Application No. 202214072937, Oct. 29, 2025, six pages.
The Japan Patent Office, Notice of Allowance, Japanese Patent Application No. 2022-204068, Feb. 1, 2024, six pages.

(Continued)

*Primary Examiner* — Geraldina Visconti
(74) *Attorney, Agent, or Firm* — Fenwick & West LLP

(57) ABSTRACT

A light emitting device and a light emitting display device that are capable of improving efficiency, driving voltage, and lifespan by varying the configuration of a layer adjacent to a blue light emitting layer in a blue fluorescent stack contacting a cathode are disclosed. The light emitting device includes stacks between an anode and a cathode, wherein an $n^{th}$ stack contacting the cathode is a first blue stack that includes a first hole transport layer, a first electron-blocking layer, a first blue light emitting layer containing a boron-based dopant having an emission peak of 430 nm to 480 nm, a first electron transport layer contacting the first blue light emitting layer, and an electron injection layer having two sides contacting the first electron transport layer and the cathode, respectively, wherein the first electron transport layer contains a mixture of a first material and a second material.

18 Claims, 14 Drawing Sheets

(56) References Cited

U.S. PATENT DOCUMENTS

| | | | | |
|---|---|---|---|---|
| 2018/0013064 | A1 | 1/2018 | Wu et al. | |
| 2018/0166647 | A1 | 6/2018 | Shin et al. | |
| 2019/0319195 | A1 | 10/2019 | Lee et al. | |
| 2019/0348613 | A1 | 11/2019 | Kim et al. | |
| 2020/0052234 | A1 | 2/2020 | Kum et al. | |
| 2021/0130355 | A1 | 5/2021 | Gao et al. | |
| 2021/0226133 | A1 | 7/2021 | Oh et al. | |
| 2021/0273192 | A1 | 9/2021 | Kim et al. | |
| 2021/0384436 | A1 | 12/2021 | Yoon et al. | |
| 2022/0246863 | A1 | 8/2022 | Lee et al. | |
| 2023/0056059 | A1 | 2/2023 | Lee et al. | |
| 2023/0217815 | A1* | 7/2023 | Song | H10K 85/633 257/40 |
| 2023/0217821 | A1* | 7/2023 | Song | H10K 85/60 257/40 |
| 2023/0255078 | A1* | 8/2023 | Song | C07D 209/08 257/40 |

FOREIGN PATENT DOCUMENTS

| | | | |
|---|---|---|---|
| CN | 109476607 | A | 3/2019 |
| EP | 3483146 | A1 | 5/2019 |
| EP | 3923364 | A1 | 12/2021 |
| EP | 4207995 | A1 | 7/2023 |
| JP | 2016-132642 | A | 7/2016 |
| JP | 2019-161218 | A | 9/2019 |
| KR | 10-2013-0051875 | A | 5/2013 |
| KR | 10-2017-0084917 | A | 7/2017 |
| KR | 10-2018-0001826 | A | 1/2018 |
| KR | 10-2018-0005534 | A | 1/2018 |
| KR | 10-2107199 | B1 | 5/2020 |
| KR | 10-2020-0081979 | A | 7/2020 |
| KR | 10-2021-0072414 | A | 6/2021 |
| TW | 201821590 | A | 6/2018 |
| WO | WO 2014/010824 | A1 | 1/2014 |
| WO | WO 2017/122988 | A1 | 7/2017 |
| WO | WO 2020/067593 | A1 | 4/2020 |
| WO | WO 2020/138876 | A1 | 7/2020 |
| WO | WO 2021/034039 | A1 | 2/2021 |

OTHER PUBLICATIONS

Korean Intellectual Property Office, Office Action, Korean Patent Application No. 10-2021-0194800, May 15, 2025, 19 pages.

Taiwan Intellectual Property Office, Office Action, Taiwanese Patent Application No. 111147657, Dec. 12, 2023, 26 pages.

* cited by examiner

LIGHT EMITTING DEVICE AND LIGHT EMITTING DISPLAY DEVICE INCLUDING THE SAME

CROSS-REFERENCE TO RELATED APPLICATIONS

This application claims the benefit of Republic of Korea Patent Application No. 10-2021-0194800, filed on Dec. 31, 2021, and Republic of Korean Patent Application No. 10-2022-0000005, filed on Jan. 1, 2022, each of which are hereby incorporated by reference in its entirety.

BACKGROUND

Field of Technology

The present disclosure relates to a light emitting device, and more particularly to a light emitting device including a plurality of stacks to realize white color, wherein the light emitting device is capable of improving the efficiency of a blue stack adjacent to a cathode, and reducing a driving voltage and improving white efficiency in an overall stack structure, and a light emitting display device including the same.

Discussion of the Related Art

Recently, a light emitting display device that does not require a separate light source and has a light emitting device in a display panel without a separate light source to make the display device compact and realize clear color has been considered a competitive application.

Meanwhile, the light emitting device used in light emitting display devices requires higher efficiency in order to realize a desired image quality, and is implemented in the form of a plurality of stacks. However, there is a limitation in efficiency increase using a plurality of stacks due to the difference in the emission color and emission mechanism implemented between respective stacks. In addition, there is a problem in that reliability is reduced because there is no consideration for stability when changing materials to increase efficiency.

SUMMARY

Accordingly, the present disclosure is directed to a light emitting device and a light emitting display device including the same that substantially obviate one or more problems due to the limitations and disadvantages of the related art.

It is an object of the present disclosure to provide a light emitting device that is capable of improving both the driving voltage and lifespan to desired levels based on modification of a fluorescent light emitting layer having low internal quantum efficiency and structures adjacent thereto.

Additional advantages, objects, and features of the disclosure will be set forth in part in the description which follows and in part will become apparent to those having ordinary skill in the art upon examination of the following, or may be learned from practice of the disclosure. The objectives and other advantages of the disclosure may be realized and attained by the structure particularly pointed out in the written description and claims hereof as well as the appended drawings.

In the light emitting device and light emitting display device of the present disclosure, improved efficiency, reduced driving voltage, and prolonged lifespan can be achieved by changing the configuration of a layer adjacent to a blue light emitting layer in a blue fluorescent stack that comes into contact with a cathode.

To achieve these objects and other advantages and in accordance with the purpose of the disclosure, as embodied and broadly described herein, a light emitting device according to an embodiment of the present disclosure includes n (wherein n is a natural number of 2 or more) stacks between an anode and a cathode facing each other, wherein an $n^{th}$ stack contacting the cathode is a first blue stack, wherein the first blue stack includes a first hole transport layer, a first electron-blocking layer, a first blue light emitting layer containing a boron-based dopant having an emission peak of 430 nm to 480 nm, a first electron transport layer contacting the first blue light emitting layer, and an electron injection layer having two sides contacting the first electron transport layer and the cathode, respectively, wherein the first electron transport layer contains a mixture of a first material of Formula 1 with a second material of Formula 2.

In another aspect, a light emitting display device includes a substrate including a plurality of subpixels, a thin film transistor provided in each of the subpixels on the substrate, and the light emitting device connected to the thin film transistor.

It is to be understood that both the foregoing general description and the following detailed description of the present disclosure are exemplary and explanatory and are intended to provide further explanation of the disclosure as claimed.

BRIEF DESCRIPTION OF THE DRAWINGS

The accompanying drawings, which are included to provide a further understanding of the disclosure and are incorporated in and constitute a part of this application, illustrate embodiment(s) of the disclosure and together with the description serve to explain the principle of the disclosure. In the drawings.

Throughout the drawings and the detailed description, unless otherwise described, the same drawing reference numerals should be understood to refer to the same elements, features, and structures.

DETAILED DESCRIPTION

Figure 1:
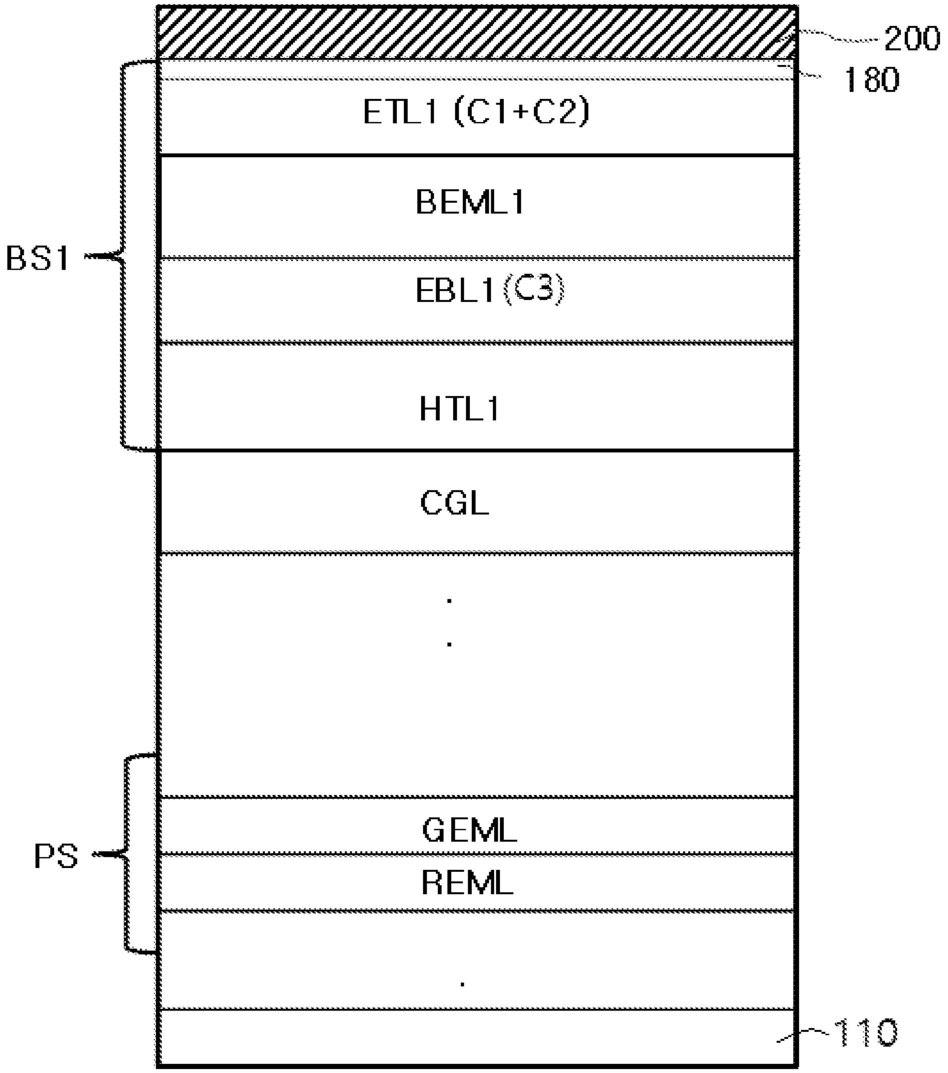
FIG. 1 is a cross-sectional view schematically illustrating a light emitting device according to one embodiment of the present disclosure.

Reference will now be made in detail to the preferred embodiments of the present disclosure, examples of which are illustrated in the accompanying drawings. Wherever possible, the same reference numbers will be used throughout the drawings to refer to the same or like parts. In the following description of the present disclosure, detailed descriptions of known functions and configurations incorporated herein will be omitted when the same may obscure the subject matter of the present disclosure. In addition, the names of elements used in the following description are selected in consideration of clear description of the specification, and may differ from the names of elements of actual products.

The shape, size, ratio, angle, number, and the like shown in the drawings to illustrate various embodiments of the present disclosure are merely provided for illustration, and are not limited to the content shown in the drawings. Wherever possible, the same reference numbers will be used throughout the drawings to refer to the same or like parts. In the following description, detailed descriptions of technologies or configurations related to the present disclosure may be omitted so as to avoid unnecessarily obscuring the subject matter of the present disclosure. When terms such as "including", "having", and "comprising" are used throughout the specification, an additional component may be present, unless "only" is used. A component described in a singular form encompasses a plurality thereof unless particularly stated otherwise.

The components included in the embodiments of the present disclosure should be interpreted to include an error range, even if there is no additional particular description thereof.

In describing a variety of embodiments of the present disclosure, when terms for positional relationships such as "on", "above", "under" and "next to" are used, at least one intervening element may be present between two elements, unless "immediately" or "directly" is used.

In describing a variety of embodiments of the present disclosure, when terms related to temporal relationships, such as "after", "subsequently", "next" and "before", are used, the non-continuous case may be included, unless "immediately" or "directly" is used.

In describing a variety of embodiments of the present disclosure, terms such as "first" and "second" may be used to describe a variety of components, but these terms only aim to distinguish the same or similar components from one another. Accordingly, throughout the specification, a "first" component may be the same as a "second" component within the technical concept of the present disclosure, unless specifically mentioned otherwise.

Features of various embodiments of the present disclosure may be partially or completely coupled to or combined with each other, and may be variously inter-operated with each other and driven technically. The embodiments of the present disclosure may be carried out independently from each other, or may be carried out together in an interrelated manner.

As used herein, the term "doped" means that, in a material that occupies most of the weight ratio of a layer, a material (for example, N-type and P-type materials, or organic and inorganic substances) having physical properties different from the material that occupies most of the weight ratio of the layer is added in an amount of less than 30% by weight. In other words, the "doped" layer refers to a layer that is used to distinguish a host material from a dopant material of a certain layer, in consideration of the specific gravity of the weight ratio. Also, the term "undoped" refers to any case other than a "doped" case. For example, when a layer contains a single material or a mixture of materials having the same properties as each other, the layer is included in the "undoped" layer. For example, if at least one of the materials constituting a certain layer is p-type and not all materials constituting the layer are n-type, the layer is included in the "undoped" layer. For example, if at least one of materials constituting a layer is an organic material and not all materials constituting the layer are inorganic materials, the layer is included in the "undoped" layer. For example, when all materials constituting a certain layer are organic materials, at least one of the materials constituting the layer is n-type and the other is p-type, when the n-type material is present in an amount of less than 30 wt %, or when the p-type material is present in an amount of less than 30 wt %, the layer is considered a "doped" layer.

Hereinafter, a light emitting device of the present disclosure and a light emitting display device including the same will be described with reference to the drawings.

FIG. 1 is a cross-sectional view schematically illustrating a light emitting device according to one embodiment of the present disclosure.

As shown in FIG. 1, the light emitting device according to the present disclosure has n (wherein n is a natural number of 2 or more) stacks such as blue stacks BS1 and phosphorescent stacks PS between an anode 110 and a cathode 200, and the stacks are divided through a charge generation layer CGL.

The light emitting device of the present disclosure has a basic configuration including at least one blue stack BS1 and a phosphorescent stack PS, and may further include a corresponding light emitting stack depending on the efficiency of production of a specific color that is required. This will be described with reference to FIGS. 2A and 2B.

In the light emitting device of the present disclosure, the stack contacting the cathode 200 is a first blue stack BS1. The first blue stack BS1 includes a first hole transport layer HTL1, a first electron-blocking layer EBL1, a first blue light emitting layer BEML1 including a boron-based dopant having an emission peak of 430 nm to 480 nm, a first electron transport layer ETL1 contacting the first blue light emitting layer BEML1, and an electron injection layer 180 having both sides contacting the first electron transport layer ETL1 and the cathode 200, respectively.

In addition, the light emitting device of the present disclosure includes a phosphorescent stack PS that emits a longer wavelength than blue light at a side thereof closer to the anode 110. The phosphorescent stack PS includes at least a red phosphorescent light emitting layer REML and a green phosphorescent light emitting layer GEML. The light emitted from the first blue light emitting layer BEML1, the light emitted from the red phosphorescent light emitting layer REML, and the light emitted from the green phosphorescent light emitting layer GEML may be collected on at least one side of the anode 110 and the cathode 200 to emit white light.

The light emitting device may further include a hole-related transport layer and electron-related transport layers below and above the phosphorescent light emitting layers REML and GEML of FIG. 1, respectively.

When the light emitting device is a bottom emission type, the anode 110 may be a transparent electrode made of ITO, IZO, or ITZO, and the cathode 200 may be aluminum (Al), an aluminum alloy, silver (Ag), a silver alloy, magnesium (Mg), or a magnesium alloy.

When the light emitting device is a top emission type, the anode 110 may include a reflective metal such as silver, a silver alloy, or aluminum, and the cathode 200 may be a thin transparent electrode or reflective transparent electrode.

The first blue stack BS1 applied to the light emitting device of the present disclosure is a stack that emits fluorescent light in consideration of both lifetime and external quantum efficiency. The boron-based dopant, which is the fluorescent material of the first blue light emitting layer BEML1, has improved stability and a longer lifespan than the phosphorescent blue dopant, and has improved external quantum efficiency compared to other fluorescent dopants. In addition, in the light emitting device of the present disclosure, the first blue stack BS1 is disposed so as to contact the cathode 200, thereby optically increasing blue emission efficiency according to a resonance effect using a microcavity.

Meanwhile, in the light emitting device of the present disclosure, the phosphorescent stack PS and the first blue stack BS1 are connected via the charge generation layer CGL in order to secure efficiency of realization of white above a certain level. The light emitting device of the present disclosure aims to increase the efficiency of the first blue stack BS1, which is in contact with the cathode 200, in order to overcome the difference in internal quantum efficiency between the phosphorescent light emission mechanism and the fluorescent light emission mechanism. For this purpose, triplet-triplet annihilation (TTA) in the first blue light emitting layer BEML1 of the first blue stack BS1 is facilitated in order to improve the electron injection efficiency in the cathode 200 and the electron transport efficiency in the first blue stack BS1 and thereby rapidly transfer electrons into the first blue light emitting layer BEML1 and confine electrons and excitons in the first blue light emitting layer BEML1.

The electron injection layer 180 provided to inject electrons from the cathode 200 contains a compound containing lithium (Li), thereby reducing resistance at the interface with the organic material disposed in the cathode 200 to facilitate injection of electrons. The electron injection layer 180 may, for example, contain any one of lithium fluoride LiF and lithium quinolate Liq.

In the light emitting device of the present disclosure, the electron transport efficiency is improved by changing the inorganic material constituting the first electron transport layer ETL1 which contacts the electron injection layer 180. In addition, the light emitting device of the present disclosure contains a second material C2 as well as a first material C1 having high electron transport efficiency of Formula 1 below in order to avoid the phenomenon in which the energy barrier to transfer electrons from the cathode 200 to the first electron transport layer ETL1 is increased due to the difference in physical properties or a repulsive force at the interface between the first electron transport layer ETL1 and the electron injection layer 180, when the first electron transport layer ETL1 includes a single material having high electron transport efficiency. In addition, the second material C2 is a material that is represented by Formula 2 below and has little or no energy barrier and low interfacial resistance with a material, for example, LiF or Liq, constituting the electron injection layer 180. That is, in the blue fluorescent stack closest to the cathode 200, the first electron transport layer ETL1 contains a mixture of the first material C1 having high electron transport efficiency and the second material C2 that enables injection of electrons with little or no repulsive force at the interface between the first electron transport layer ETL1 and the electron injection layer 180.

[Formula 1]

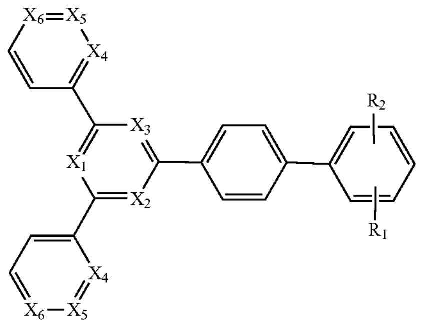

$R_1$ and $R_2$ are each independently selected from a cycloalkyl group, an aryl group, a heteroaryl group, and a carbazole group. $X_1$, $X_2$ and $X_3$ are each independently N or CH. At least one of $X_4$, $X_5$ and $X_6$ should be N, and the remaining ones are CH.

Here, the first material of Formula 1 constituting the first electron transport layer ETL1 maintains the structural bond of each symmetrical benzene ring on the outside of the structure and is capable of transferring electrons to the first blue light emitting layer EML1 with high efficiency due to strong electron donor activity of the nitrogen (N) at the end of the symmetrical benzene ring.

[Formula 2]

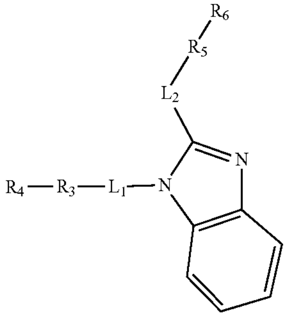

$L_1$ and $L_2$ may be independently a single bond. Or $L_1$ and $L_2$ may independently include one selected from a phenyl group and a naphthyl group. In some embodiments, $L_1$ and $L_2$ may independently include one selected from a phenylene group and a naphthylene group.

$R_3$, $R_4$ and $R_6$ may independently include one selected from a phenyl group, a naphthyl group, and an anthracene group. $R_5$ may be a single bond or may include one selected from a methyl, an ethyl, a phenyl group, a naphthyl group, and an anthracene group.

In some embodiments, $R_3$ may be independently selected from a phenylene group, a naphthylene group, and an anthrylene group. $R_4$ may be selected from a phenyl group, a naphthyl group, and an anthracene group. $R_5$ may be a single bond or include an alkylene group, such as a phenylene group, a naphthylene group, and an anthrylene group. $R_6$ may be selected from an alkyl group such as a phenyl group, a naphthyl group, and an anthracene group.

Meanwhile, in the light emitting device of the present disclosure, electrons and excitons may be rapidly transferred to the interface between the first blue light emitting layer EML1 and the first electron-blocking layer EBL1 due to the excellent electron transport efficiency of the first electron transport layer ETL1.

As another feature of the light emitting device of the present disclosure, the first electron-blocking layer EBL1 may be formed of a deuterium-substituted material in order to prevent reduction in the efficiency and lifespan of the light emitting device due to transfer of electrons to the first electron-blocking layer EBL1.

For example, the first electron-blocking layer EBL1 may contain a third material C3 represented by Formula 3 below.

[Formula 3]

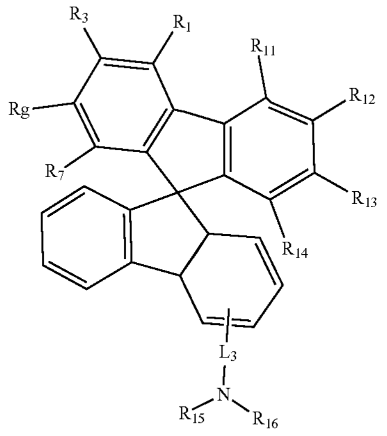

$L_3$ may be a single bond, or may include a phenyl group or a naphthyl group. In some embodiments, $L_3$ may include one selected from a phenylene group and a naphthylene group. $R_7$ to $R_{14}$ may be deuterium. Or $R_7$ to $R_{14}$ $R_7$ to $R_{14}$ may be substituted with deuterium. $R_{15}$ and $R_{16}$ may be each independently selected from a phenyl group, a deuterium-substituted phenyl group, a biphenyl group, a deuterium-substituted biphenyl group, a fluorenyl group, a deuterium-substituted fluorenyl group, a heteroaryl group, a deuterium-substituted heteroaryl group, a carbazole group, a deuterium-substituted carbazole group, a dibenzofuran group, a deuterium-substituted dibenzofuran group, a dibenzothiophene group, and a deuterium-substituted dibenzothiophene group. In an embodiment, the deuterium substitution is partial. In a preferred embodiment, the deuterium substitution is full.

Specifically, examples of the third material C3 of Formula 3 will be described later with reference to experiments.

Hereinafter, examples in which the light emitting device of the present disclosure is applied to a two-stack structure and a three-stack structure will be described, respectively. However, the light emitting device of the present disclosure is not limited to the suggested two- or three-stack structure, and may be applicable to a structure having any number of stacks, including four stacks or more, as long as it includes a blue fluorescent stack and a phosphorescent stack, the stack contacting the cathode is the blue fluorescent stack, and the first electron transport layer contacting the electron injection layer includes both the first material and the second material.

Figure 2A:
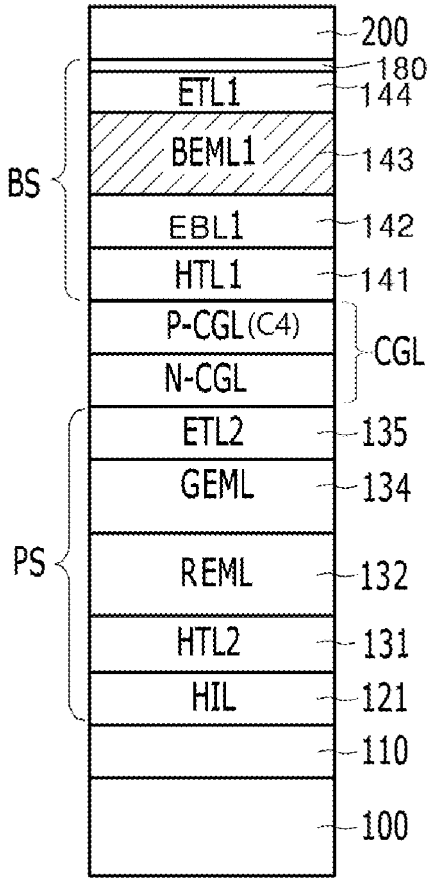
FIGS. 2A and 2B are cross-sectional views illustrating embodiments of a light emitting device of the present disclosure, respectively.
Figure 2B:
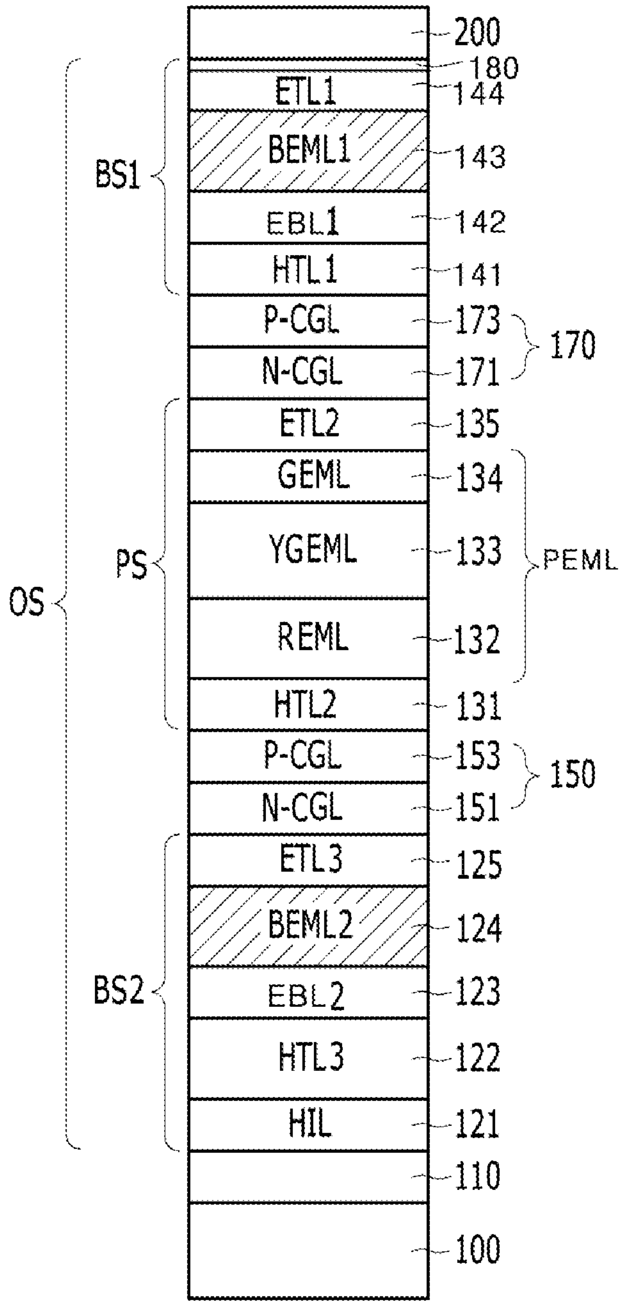

FIGS. 2A and 2B are cross-sectional views illustrating embodiments of a light emitting device of the present disclosure.

As shown in FIG. 2A, the light emitting device according to a first embodiment of the present disclosure includes an anode 110 and a cathode 200 facing each other on a substrate 100, and a phosphorescent stack PS, a charge generation layer CGL, and a blue fluorescent stack BS sequentially provided between the anode 110 and the cathode 200.

Like the first blue fluorescent stack BS1 of FIG. 1, the blue fluorescent stack BS includes a first hole transport layer HTL1 141, a first electron-blocking layer EBL1 142, a first blue light emitting layer BEML1 143 containing a boron-based dopant having an emission peak of 430 nm to 480 nm, a first electron transport layer ETL1 144 contacting the blue light emitting layer BEML1, and an electron injection layer 180 having both sides contacting the first electron transport layer ETL1 144 and the cathode 200, respectively. The first electron transport layer ETL1 144 contains the first material C1 of Formula 1 and the second material C2 of Formula 2.

In addition, the phosphorescent stack PS includes a hole injection layer (HIL) 121, a second hole transport layer (HTL2) 131, a red phosphorescent light emitting layer (REML) 132, a green phosphorescent light emitting layer (GEML) 134, and a second electron transport layer (ETL2) 135.

Here, the charge generation layer CGL between the blue fluorescent stack BS and the phosphorescent stack PS may include an n-type charge generation layer N-CGL and a p-type charge generation layer P-CGL. The n-type charge generation layer N-CGL is formed by doping an electron-transporting host with an alkali metal, alkaline earth metal, or transition metal to generate electrons and supply the same to an electron transport layer of an adjacent stack. Referring to FIG. 2A, the n-type charge generation layer N-CGL supplies the generated electrons to the second electron transport layer (ETL2) 135 of the phosphorescent stack PS disposed thereunder. In addition, the p-type charge generation layer P-CGL generates holes and supplies the generated holes to the first hole transport layer (HTL1) 141 of the blue fluorescent stack BS disposed thereon. The p-type charge generation layer P-CGL includes a p-type dopant in a hole-transporting host. In the light emitting device of the present disclosure, the first material C1, having high electron transport efficiency, is used for the first electron transport layer 144 in the blue fluorescent stack BS, so electrons can be rapidly transferred to the first blue light emitting layer 143. In response thereto, the light emitting device of the present disclosure is also characterized in that an organic dopant (a fourth material: C4) of Formula 4, having high hole transport efficiency, is used as a p-type dopant in the p-type charge generation layer P-CGL.

[Formula 4]

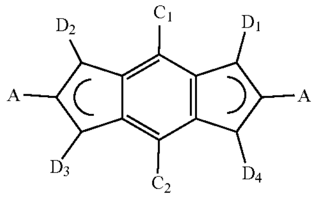

Here, A may be selected from hydrogen, deuterium, a halogen group, a cyano group, a malononitrile group, a trifluoromethyl group, a trifluoromethoxy group, a substituted or unsubstituted aryl or heteroaryl group, a substituted or unsubstituted $C_1$-$C_{12}$ alkyl group. In the Formula 2, a substituent of A may include one of a cyano group, a halogen group, a trifluoromethyl group, a trifluoromethoxy group, hydrogen and deuterium. $C_1$ and $C_2$ may be each independently one of hydrogen, deuterium, a halogen group, or a cyano group. $D_1$ to $D_4$ are each independently connected by a single or double bond, and are substituted with one of a halogen group, a cyano group, a malononitrile group, a trifluoromethyl group, or a trifluoromethoxy group, and at least two thereof include a cyano group.

Specifically, examples of the fourth material C4 of Formula 4 will be described later with reference to experiments.

The light emitting device according to the second embodiment of the present disclosure shown in FIG. 2B aims at further improving blue light emission efficiency, and includes a first blue fluorescent stack BS1 and a second blue fluorescent stack BS2, which contact the cathode 200 and the anode 110, respectively, and a phosphorescent stack PS between the first blue fluorescent stack BS1 and the second blue fluorescent stack BS2. The first blue fluorescent stack BS1 is the same as that of FIGS. 1 and 2A described above, so a description thereof will be omitted.

The second blue fluorescent stack BS2 includes a hole injection layer (HIL) 121, a third hole transport layer (HTL3) 122, a second electron-blocking layer (EBL2) 123, a second blue light emitting layer (BEML2) 124, and a third electron transport layer (ETL3) 125, which are sequentially stacked on the anode 110.

In addition, the phosphorescent stack PS includes a second hole transport layer (HTL2) 131, a phosphorescent light emitting layer PEML, and a second electron transport layer (ETL2) 135. In the second embodiment of FIG. 2B, the phosphorescent light emitting layer PEML includes a red phosphorescent light emitting layer (REML) 132, a yellow-green phosphorescent light emitting layer (YGEML) 133, and a green phosphorescent light emitting layer (GEML) 134. The second embodiment of FIG. 2B is different from the first embodiment of FIG. 1A in that the second embodiment of FIG. 2B further includes the yellow-green phosphorescent light emitting layer YGEML between the red phosphorescent light emitting layer and the green phosphorescent light emitting layer. The second embodiment can express a greater variety of colors across a wider color gamut than the first embodiment.

A first charge generation layer 170 is provided between the first blue fluorescent stack BS1 and the phosphorescent stack PS, and a second charge generation layer 150 is provided between the phosphorescent stack PS and the second blue fluorescent stack BS2.

Each of the first and second charge generation layers 170 and 150 is provided with an n-type charge generation layer N-CGL 151 or 171 and a p-type charge generation layer P-CGL 153 or 173 sequentially from the bottom.

Hereinafter, the effect of change in the material of the electron transport layer in the blue fluorescent stack close to the cathode will be described based on experiments.

In addition, examples of the first material C1 of Formula 1 to form the electron transport layer include the following materials ETM-01 to ETM-60.

<ETM-01>

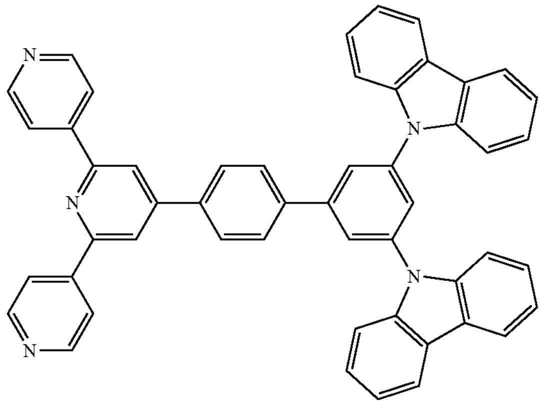

<ETM-02>

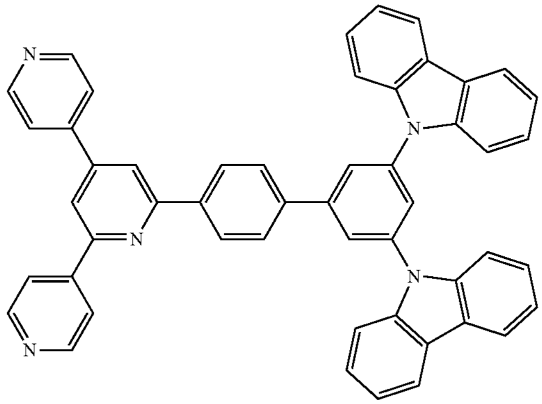

<ETM-03>

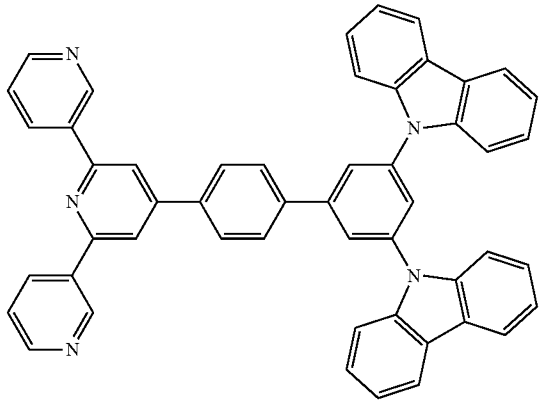

-continued
<ETM-04>
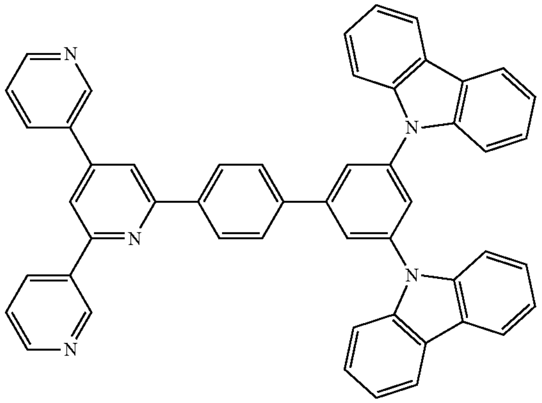
<ETM-05>
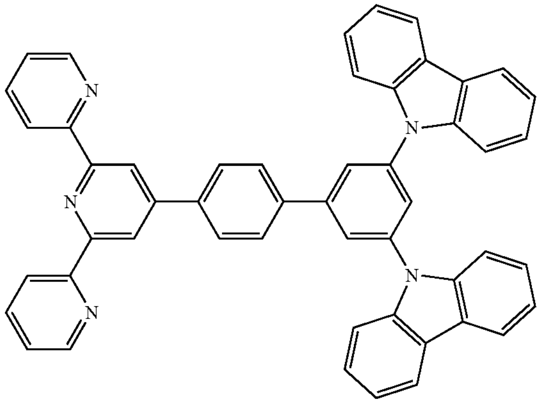
<ETM-06>
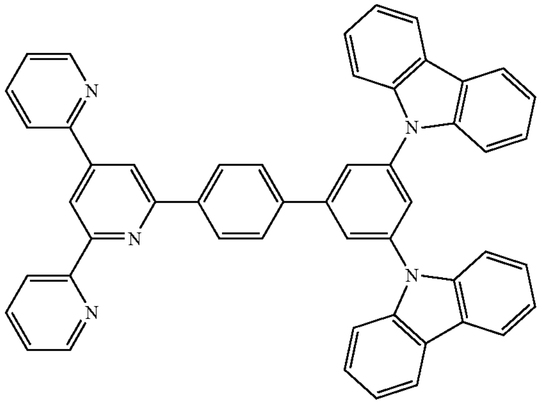
-continued
<ETM-07>
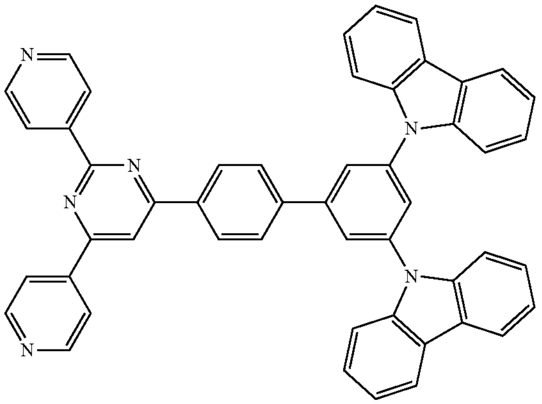
<ETM-08>
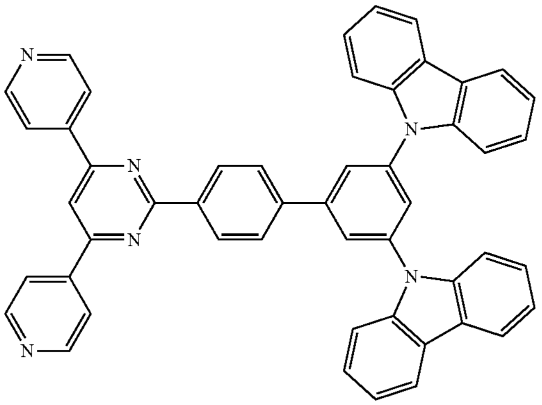
<ETM-09>
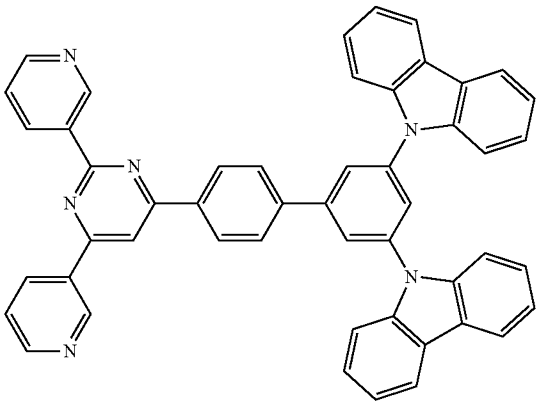

-continued
<ETM-10>
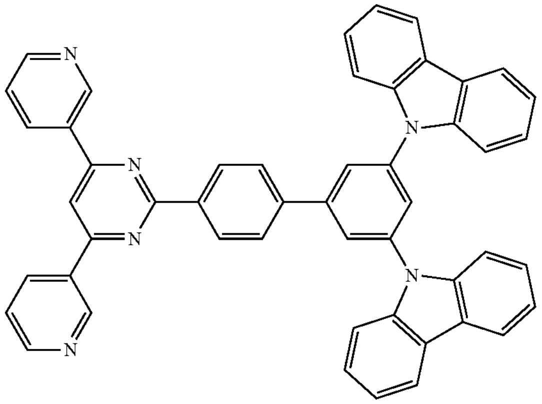
<ETM-11>
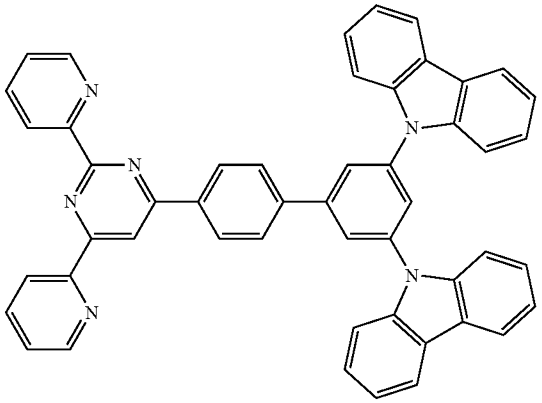
<ETM-12>
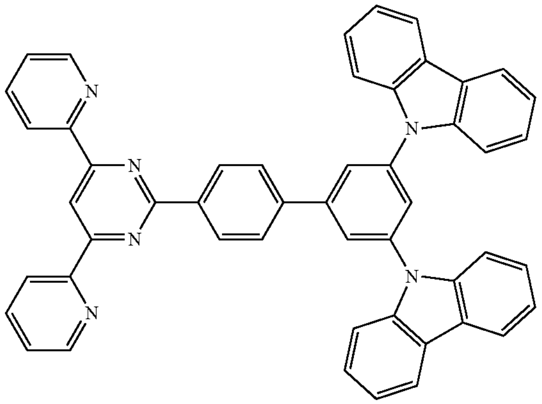
<ETM-13>
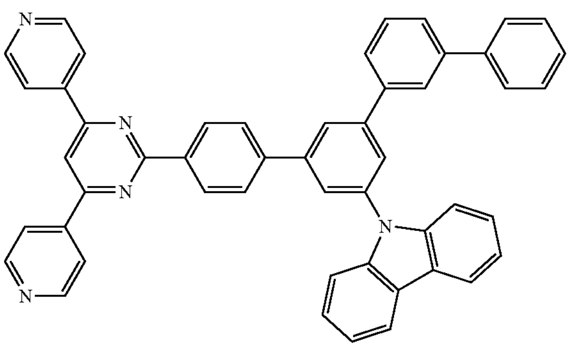
-continued
<ETM-14>
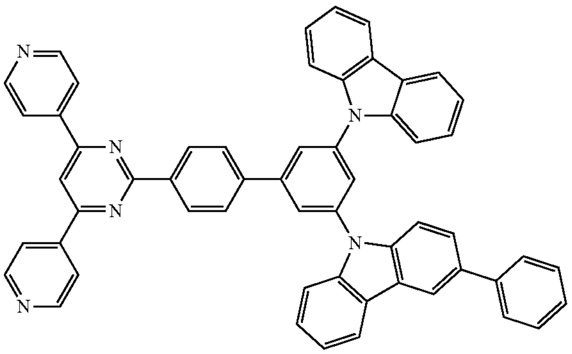
<ETM-15>
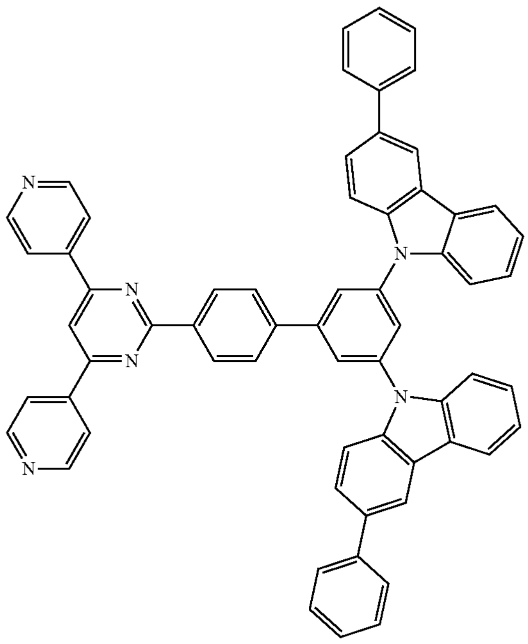
<ETM-16>
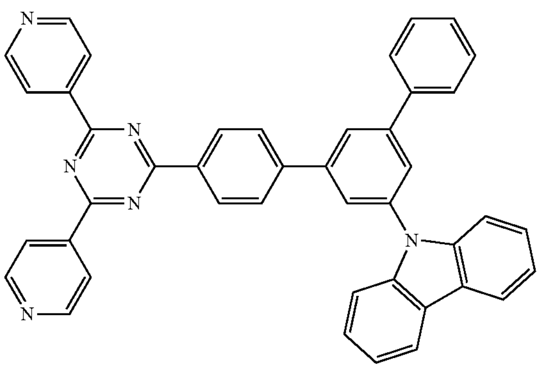

-continued
<ETM-17>
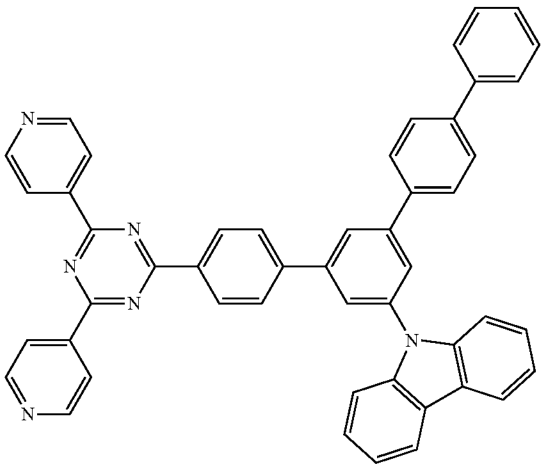
<ETM-18>
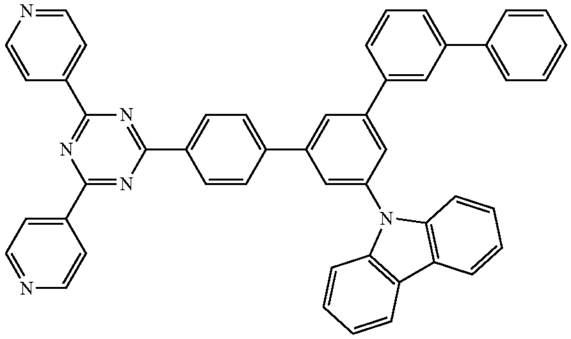
<ETM-19>
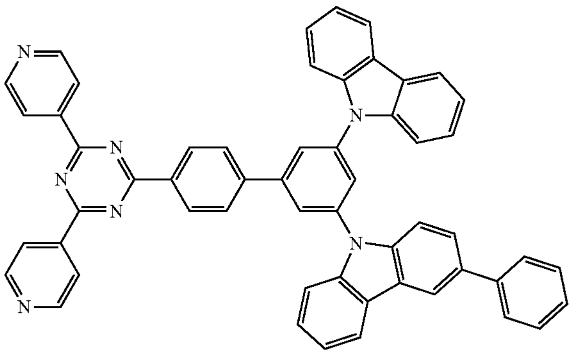
-continued
<ETM-20>
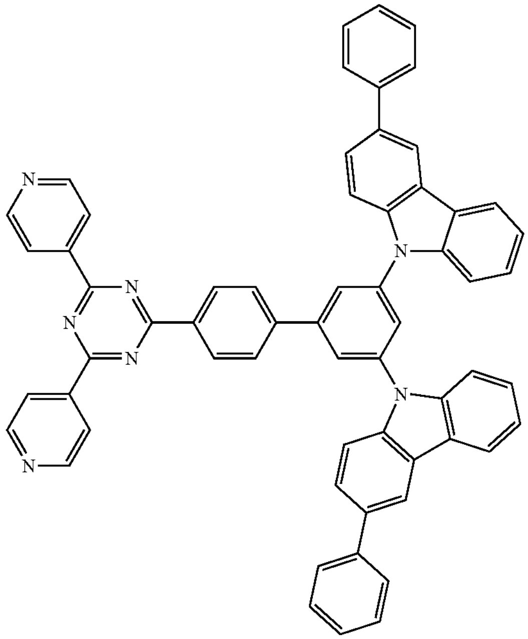
<ETM-21>
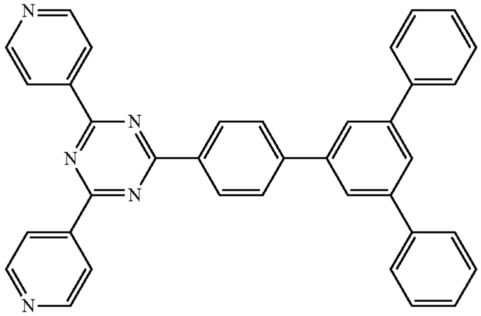
<ETM-22>
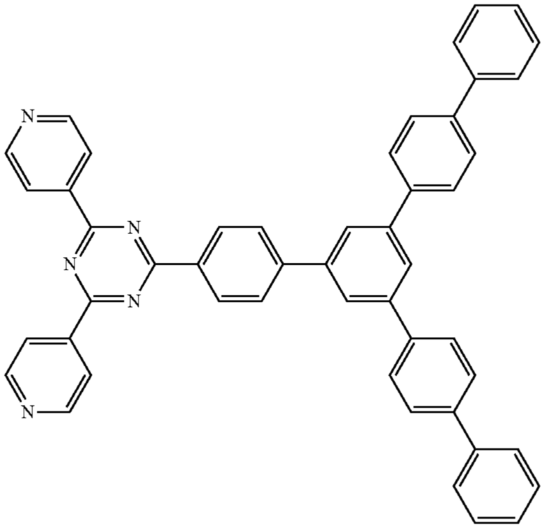

-continued
<ETM-23>
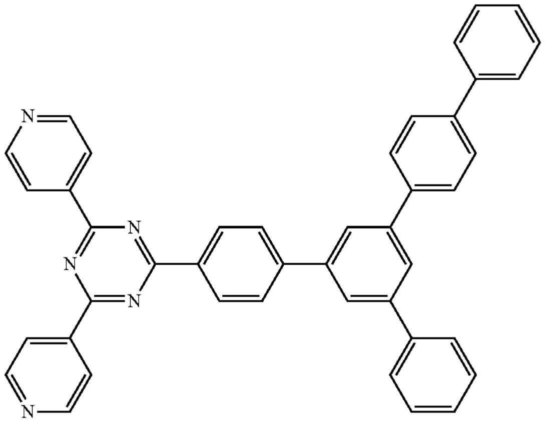
<ETM-24>
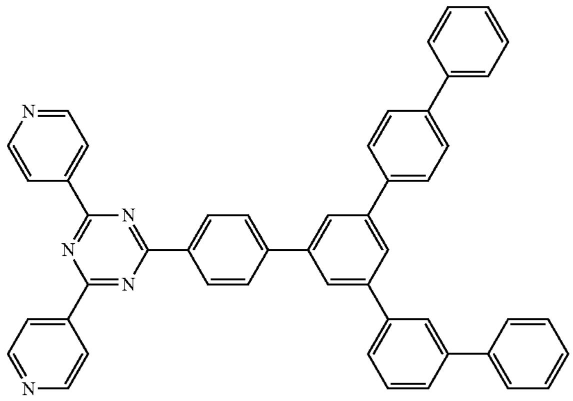
<ETM-25>
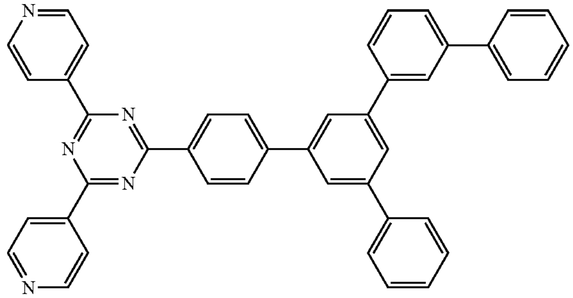
<ETM-26>
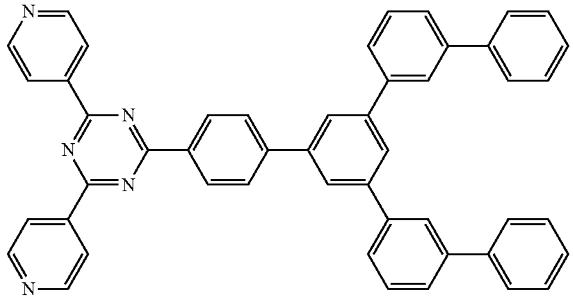
-continued
<ETM-27>
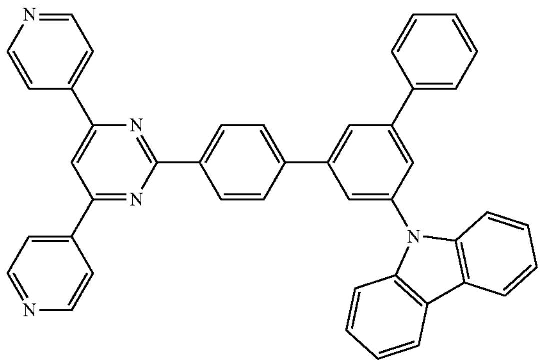
<ETM-28>
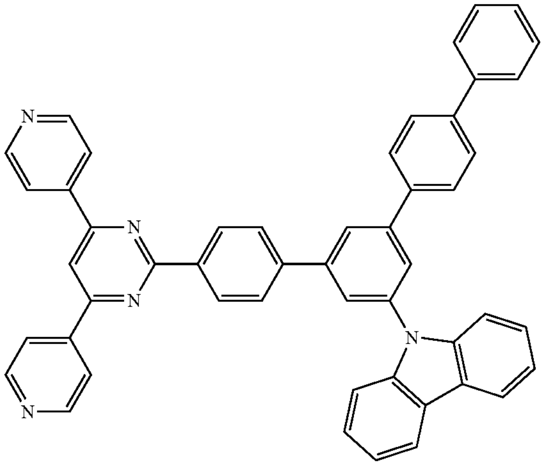
<ETM-29>
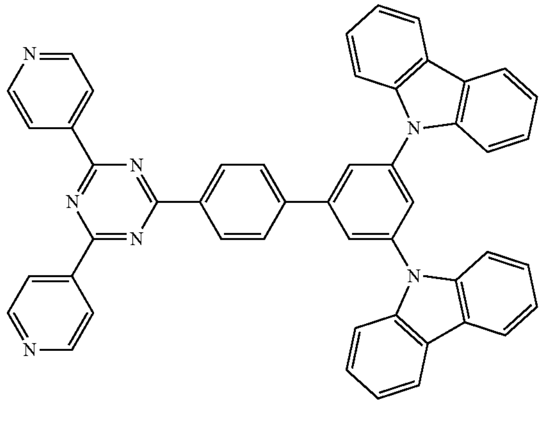

-continued
<ETM-30>
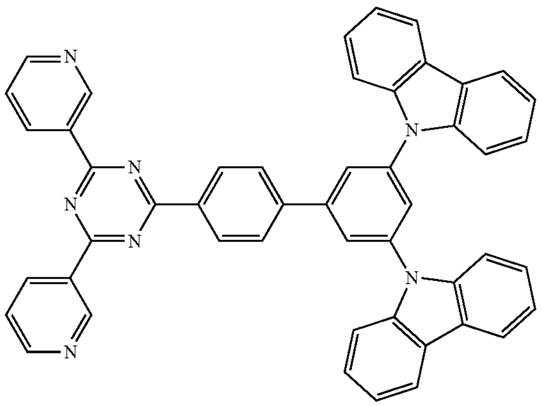
<ETM-31>
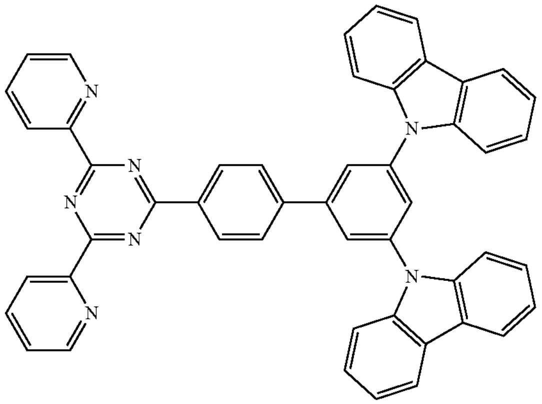
<ETM-32>
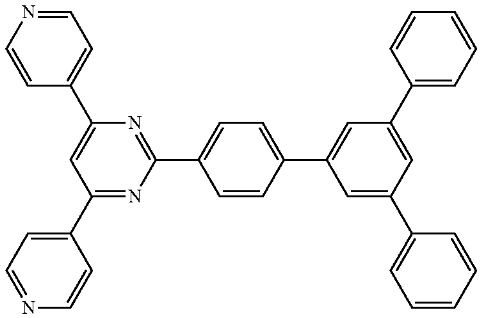
-continued
<ETM-33>
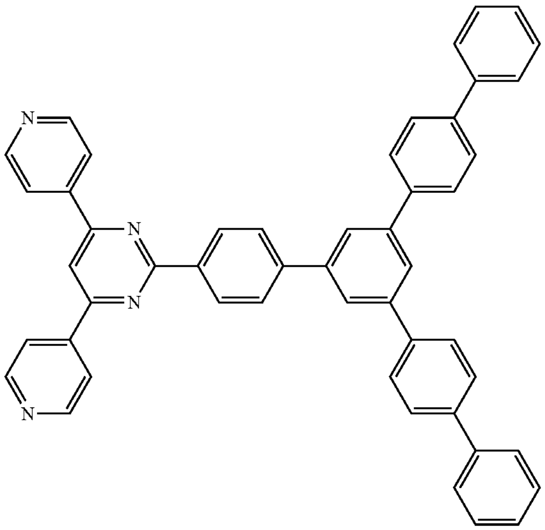
<ETM-34>
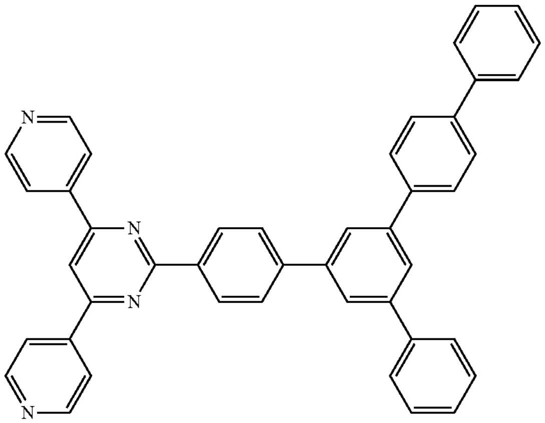
<ETM-35>
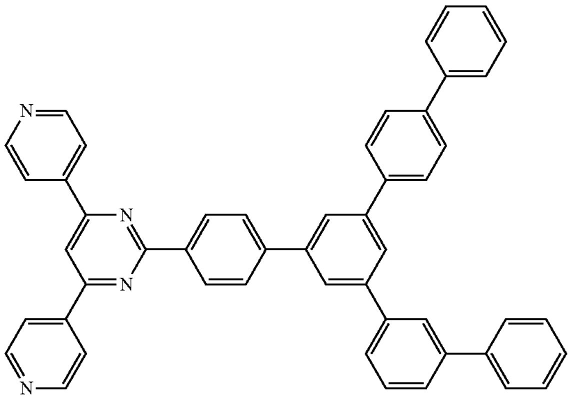

-continued
<ETM-36>
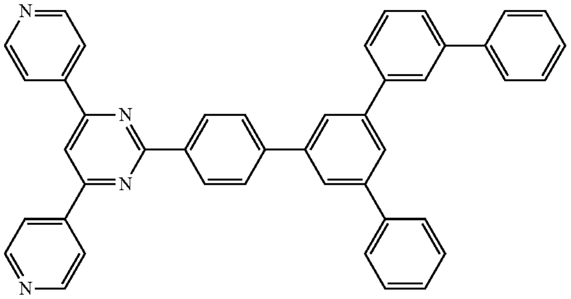
<ETM-37>
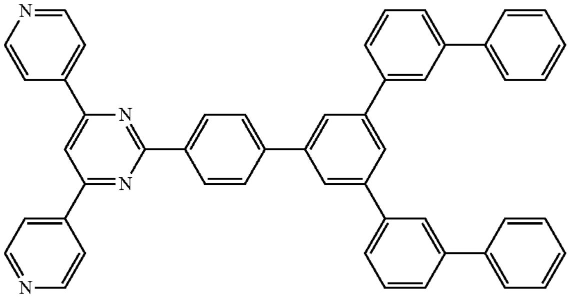
<ETM-38>
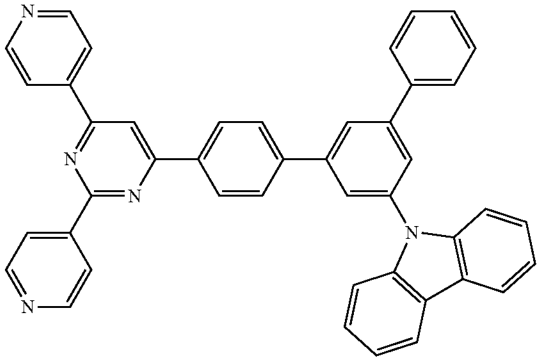
<ETM-39>
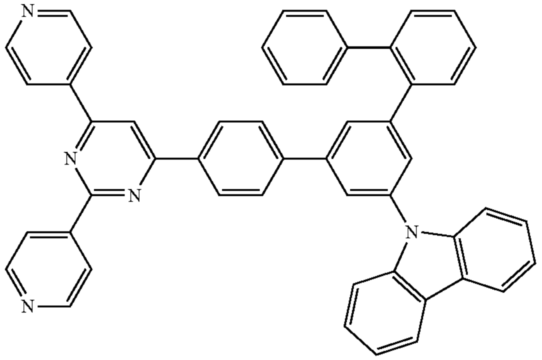
-continued
<ETM-40>
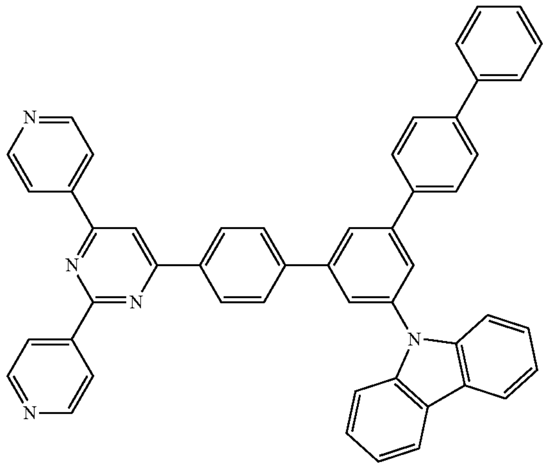
<ETM-41>
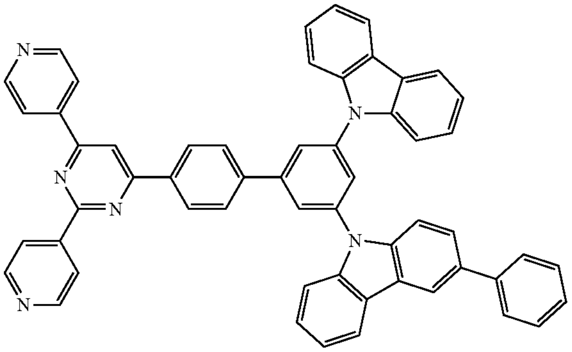
<ETM-42>
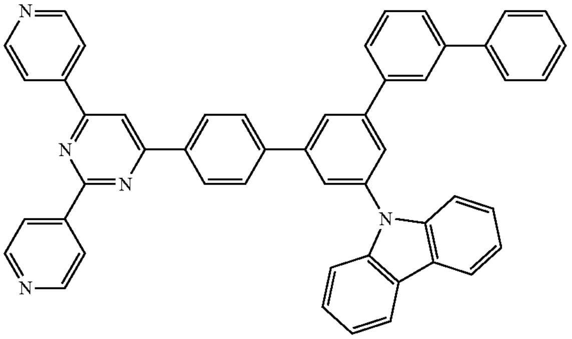

-continued
<ETM-43>
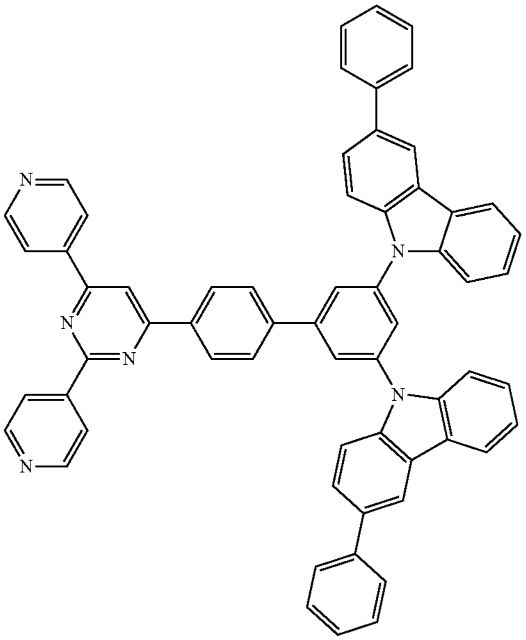
<ETM-44>
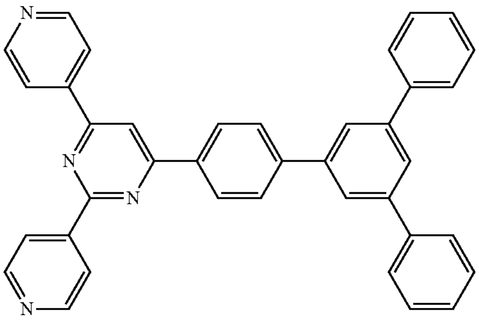
<ETM-45>
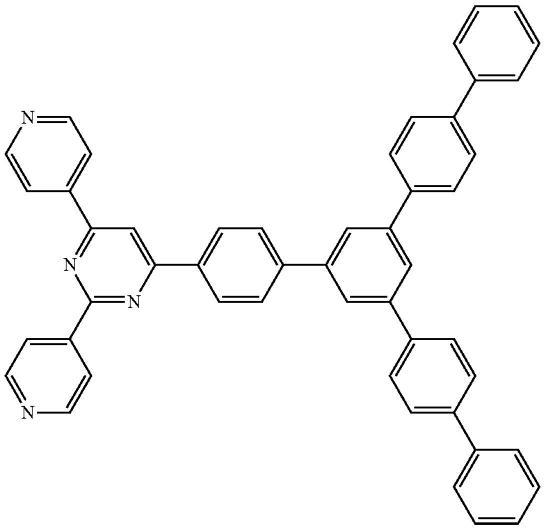
-continued
<ETM-46>
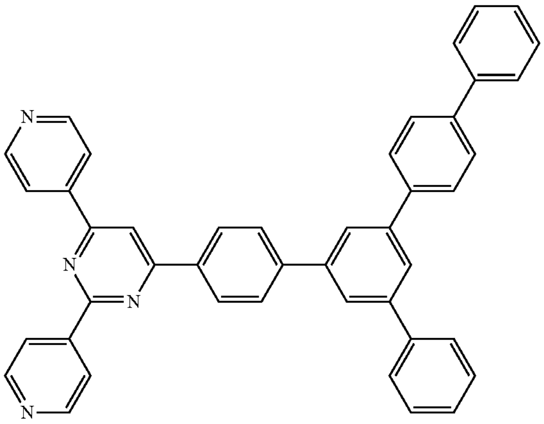
<ETM-47>
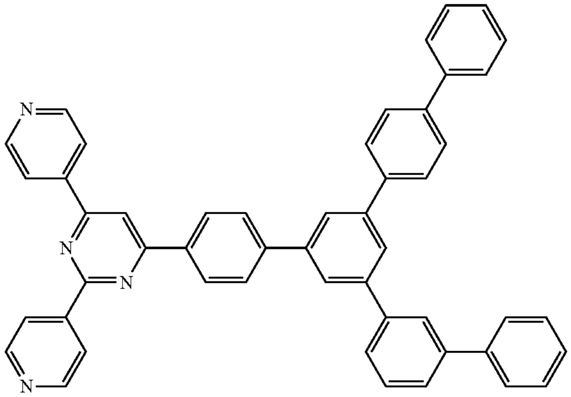
<ETM-48>
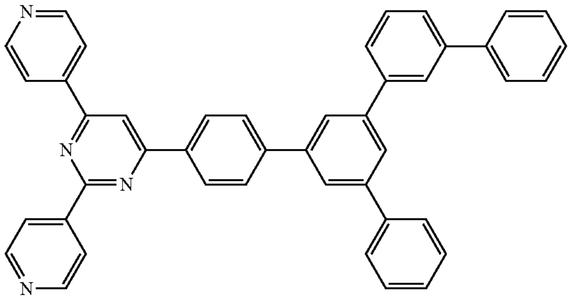
<ETM-49>
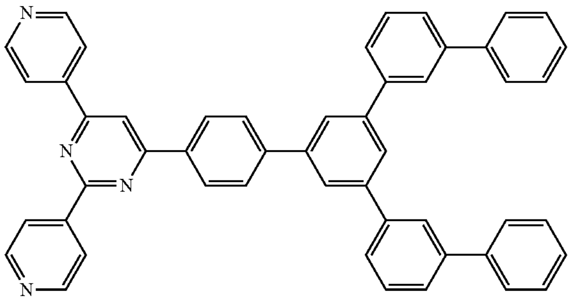

-continued
<ETM-50>
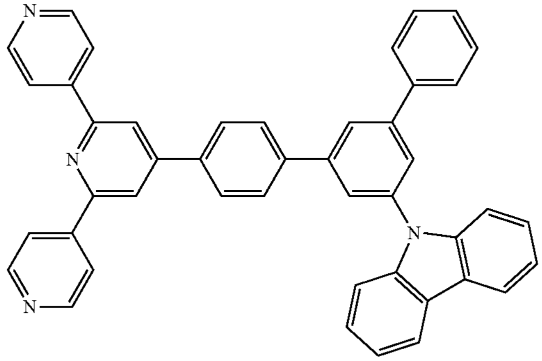
<ETM-51>
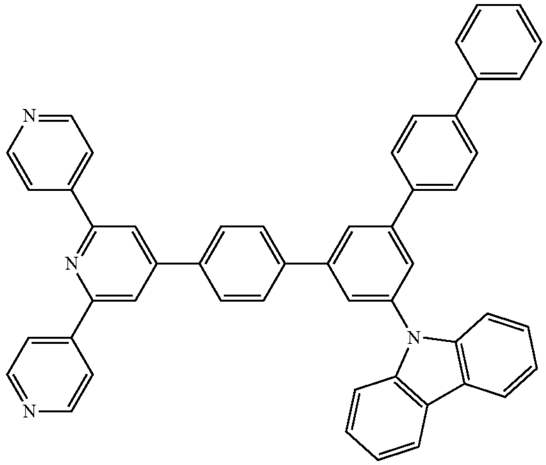
<ETM-52>
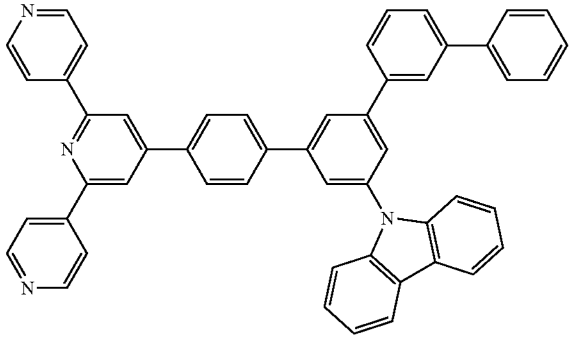
<ETM-53>
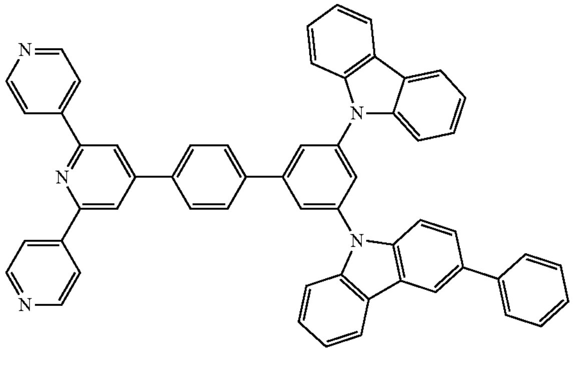
-continued
<ETM-54>
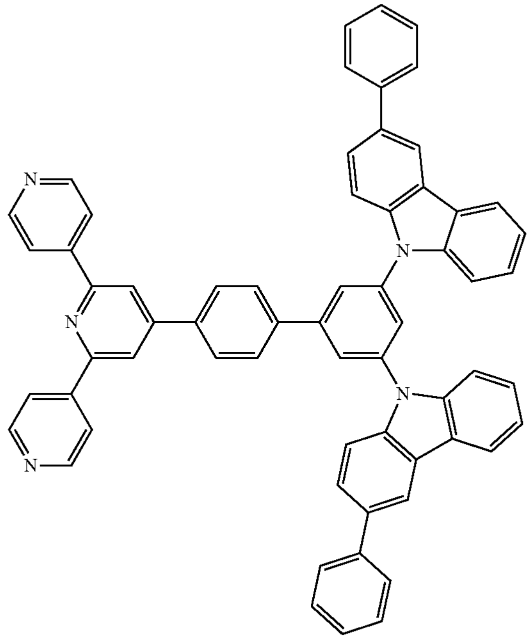
<ETM-55>
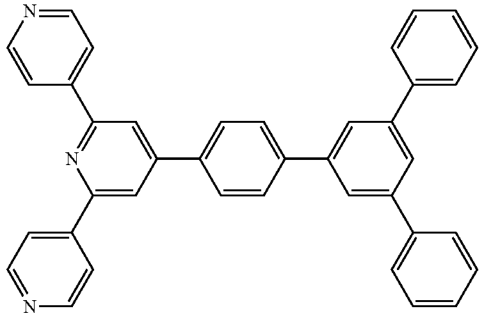
<ETM-56>
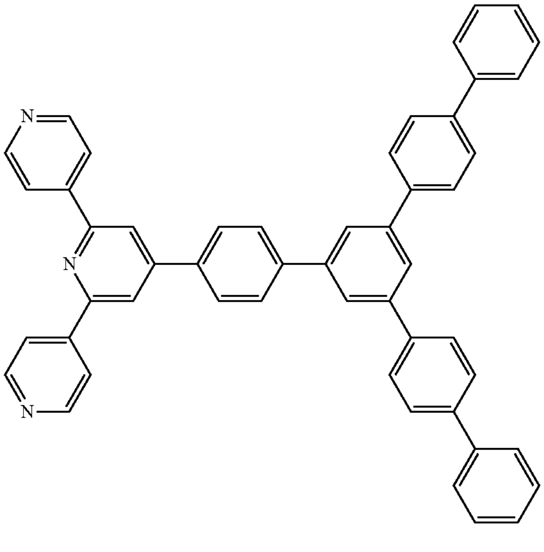

-continued

<ETM-57>

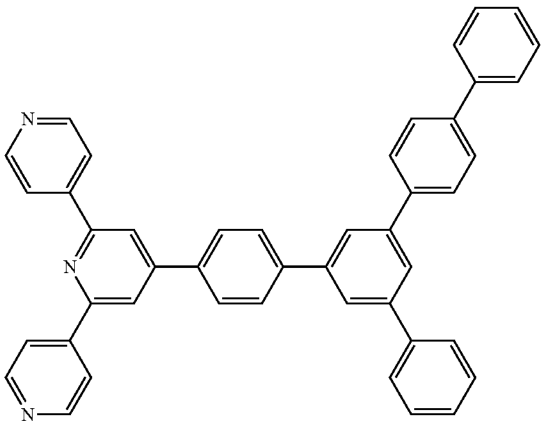

<ETM-58>

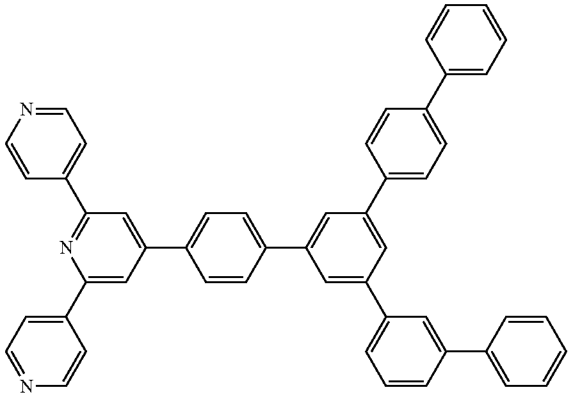

<ETM-59>

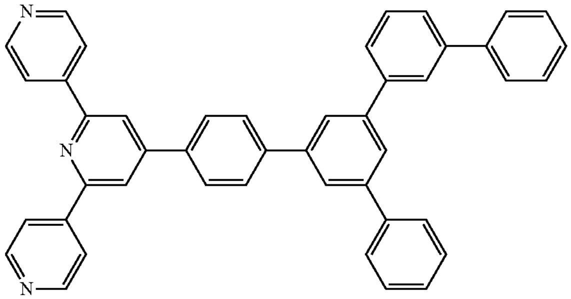

<ETM-60>

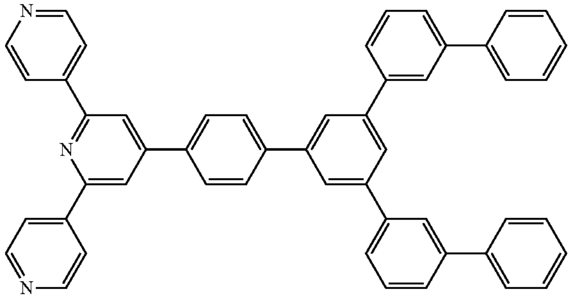

As a representative material of Formula 1, ETM-01 was obtained through the following preparation method.

(1) Synthesis of first compound:

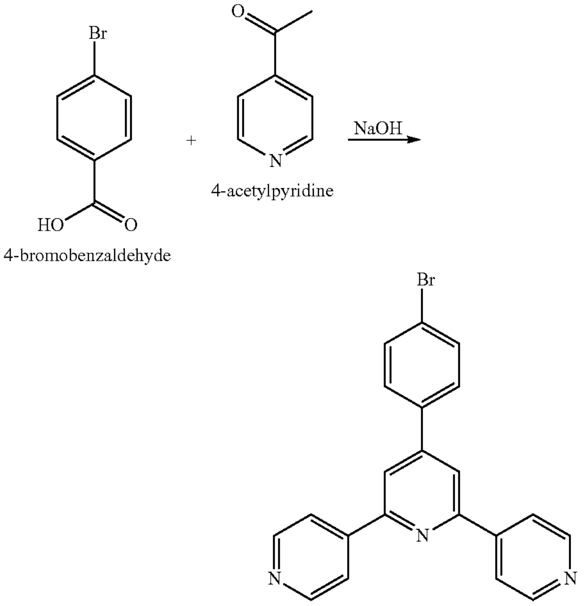

4-bromobenzaldehyde 4-acetylpyridine

First Compound 6.0 g (49.5 mmol) of 4-acetylpyridine and 9.0 g (48.6 mmol) of 4-bromobenzaldehyde were prepared and placed in a flask along with 200 mL of a 2 wt % NaOH aqueous solution, followed by stirring at room temperature for 10 hours and observation of the color change of the reaction solution. Then, 6.0 g (49.5 mmol) of 4-acetylpyridine was added thereto, and an NaOH concentration was set to 20 wt %, followed by stirring at 80° C. for 8 hours. The product was dehydrated without purification and stirred under reflux conditions in a solution containing more than 36.0 g of ammonium acetate in 500 mL of ethanol for 5 hours. Then, the product was recrystallized from the resulting reaction solution ethanol to obtain a first compound (11g, 60% yield).

(2) Synthesis of second compound:

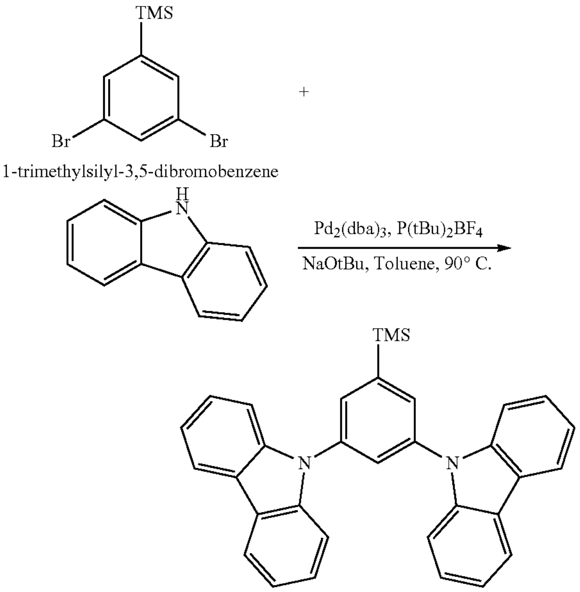

1-trimethylsilyl-3,5-dibromobenzene 8.1 g (48.75 mmol) of Carbazole, 6.0 g (19.5 mmol) of 1-trimethylsilyl-3,5-dibromobenzene, 0.89 g (1.0 mmol) of tris(dibenzylideneacetone)dipalladium(0) ($Pd_2(dba)_3$), 0.59 g (2.0 mmol) of tri-tert-butylphosphine tetrafluoroborate ($P(tBu)_3BF_4$) and 4.7 g (48.8 mmol) of NaOtBu were added to dry toluene (200 mL), followed by stirring at 90° C. for 10 hours. Upon completion of the reaction, the NaOtBu residue was filtered and then the product was extracted with ethyl acetate. The resulting product was dehydrated with $MgSO_4$ and purified by column chromatography (hexane: EA=20:1(v/v)) to obtain a second compound (6.1 g, 65% yield).

(3) Synthesis of third compound:

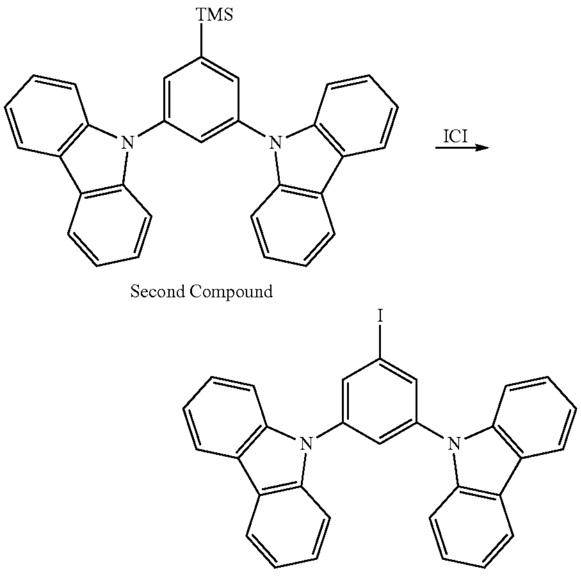

Second Compound

Third Compound

The second compound (4.0 g, 8.3 mmol) was dissolved in $CCl_4$ (70 mL), and an iodine monochloride solution (1.0 M in methylene chloride, 8.3 mL, 8.3 mmol) was added dropwise thereto at 0° C., followed by stirring for 1 hour. Then, the reaction solution was added to a 5 wt % aqueous solution of sodium thiosulfate ($Na_2S_2O_3$), followed by vigorously stirring until the reaction solution became transparent. The reaction solution was extracted with ethylene acetate, dehydrated with $MsSO_4$, and purified through column chromatography (hexane:EA=20:1(v/v)) to obtain a third compound (3.6 g, 80% yield).

(4) Synthesis of fourth compound:

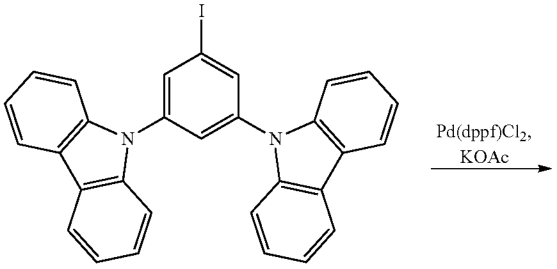

Third Compound

-continued

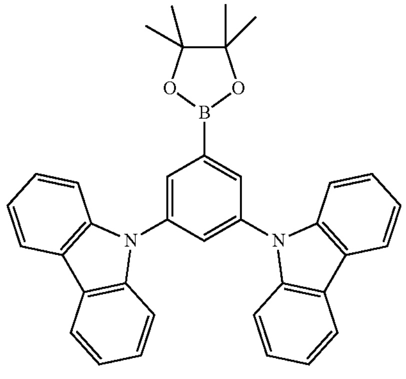

Fourth Compound

The third compound (3 g, 5.6 mmol), 4,4,4',4',5,5,5',5'-octamethyl-2,2'-bi(1,3,2,-dioxaborolane) (2.1 g, 8.4 mmol), [1,1'-Bis(diphenylphosphino)ferrocene]dichloropalladium (II) ($Pd(dppf)Cl_2$) (0.21 g, 0.28 mmol), and potassium acetate (KOAc) (1.65 g, 16.8 mmol) were mixed under an inert atmosphere formed by injection of nitrogen, and then 1,4-dioxane (30 mL) was added thereto, followed by stirring at 130° C. for 12 hours. After completion of the reaction, the mixture was extracted with ethyl acetate, dehydrated with $MgSO_4$, and purified through column chromatography (hexane:EA=7:1 (v/v)) to obtain a fourth compound (2.3 g, 75% yield).

(5) Synthesis of ETM-01:

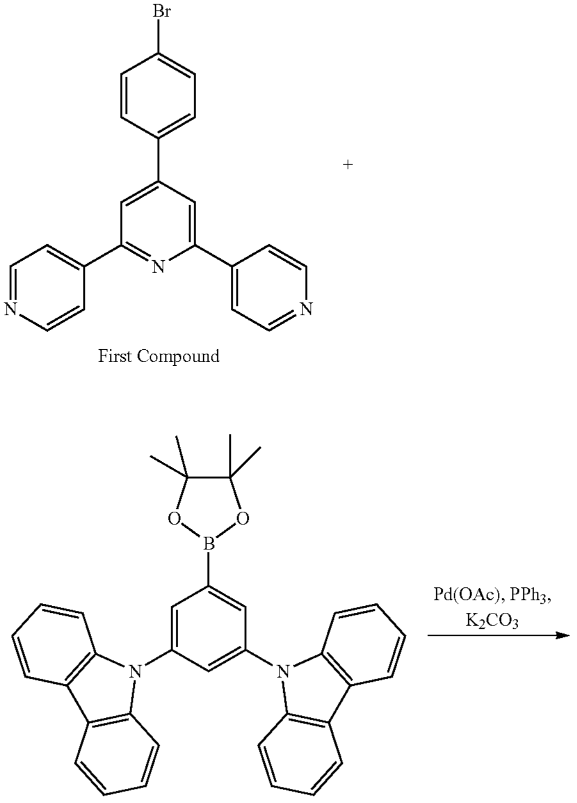

First Compound

+

Fourth Compound

-continued

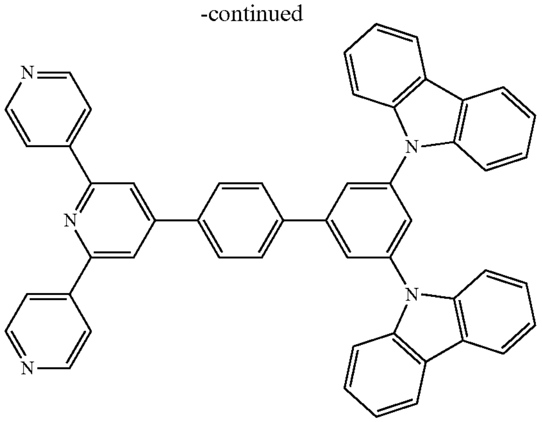

ETM-01

The first compound (1.8 g, 4.6 mmol), the fourth compound (2.3 g, 4.3 mmol), palladium(II) acetate ($Pd(OAc)_2$) (0.048 g, 0.2 mmol), triphenylphosphine ($PPh_3$) (0.28 g, 1.0 mmol), and potassium carbonate ($K_2CO_3$) (3.0 g, 21.5 mmol) were charged in a round-bottom flask in which an inert atmosphere was formed, and degassed THF/$H_2O$ (35 mL/5 mL) was added thereto, followed by stirring at 70° C. for 10 hours. After completion of the reaction, the reaction solution was extracted with dichloromethane, dehydrated with $MgSO_4$ and purified by column chromatography (hexane:EA=7:1 (v/v)) to obtain ETM-01 (2.6 g, 85% yield).

Meanwhile, the above synthesis method is used to synthetize the representative material ETM-01 of Formula 1, and ETM-02 to ETM-60, the materials of other Formulas, may be obtained by changing the number of nitrogen substituents during synthesis of the first compound in (1) or by changing the number of synthesized carbazoles or phenyl groups during synthesis of the second compound in (2).

In addition, examples of the second material C2 of Formula 2 to form the electron transport layer include the following materials ETMB-01 to ETMB-40.

<ETMB-01>

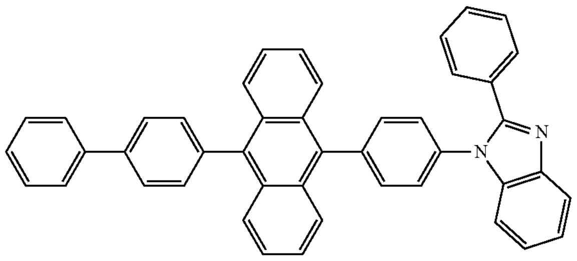

<ETMB-02>

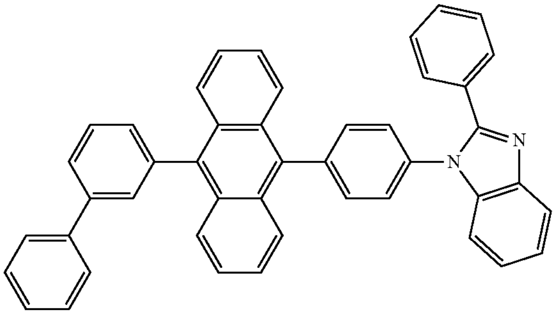

-continued

<ETMB-03>

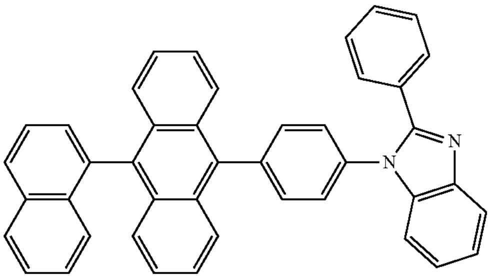

<ETMB-04>

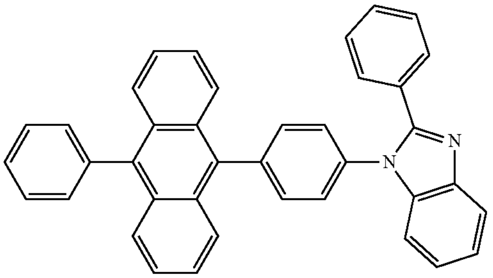

<ETMB-05>

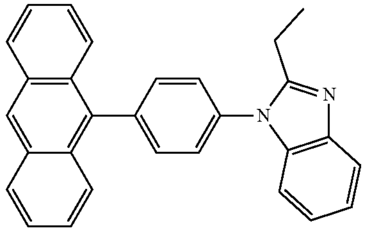

<ETMB-06>

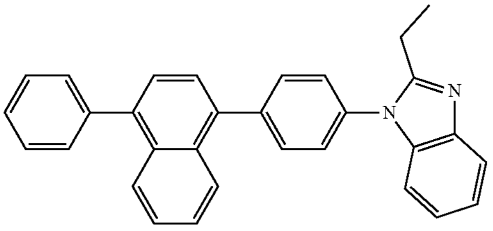

<ETMB-07>

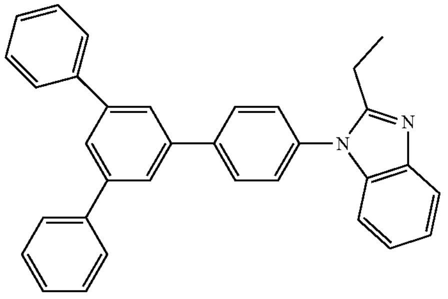

-continued
<ETMB-08>
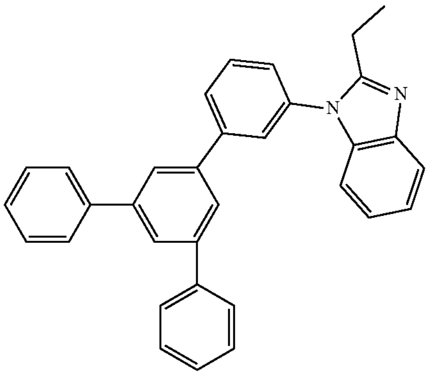
<ETMB-09>
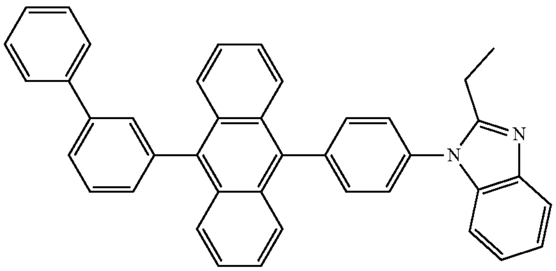
<ETMB-10>
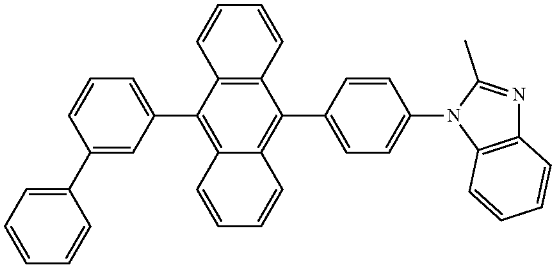
<ETMB-11>
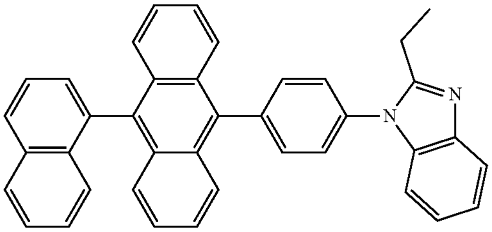
<ETMB-12>
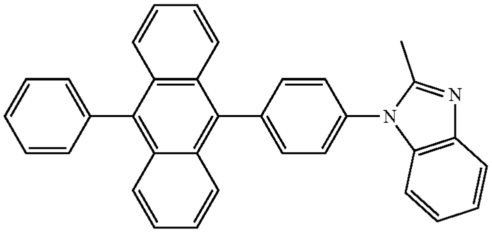
-continued
<ETMB-13>
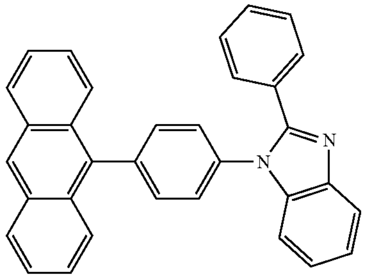
<ETMB-14>
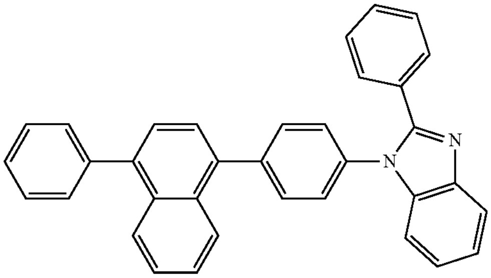
<ETMB-15>
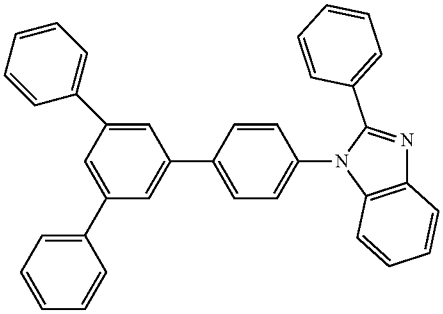
<ETMB-16>
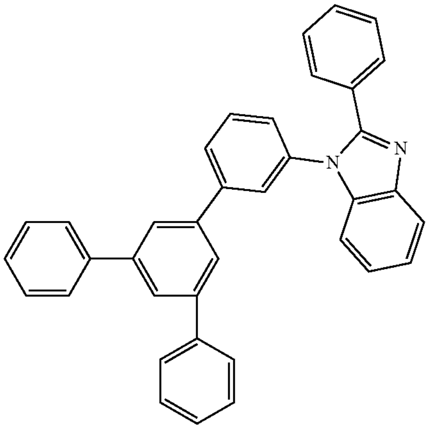
<ETMB-17>
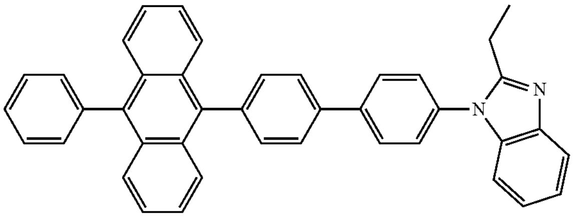

-continued
<ETMB-18>
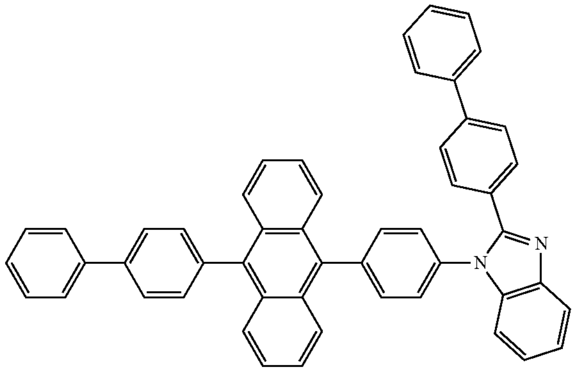
<ETMB-19>
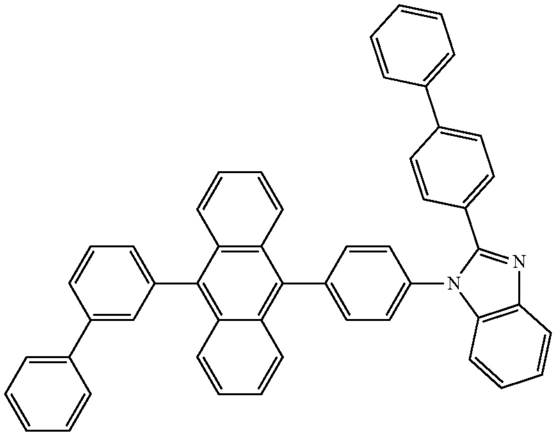
<ETMB-20>
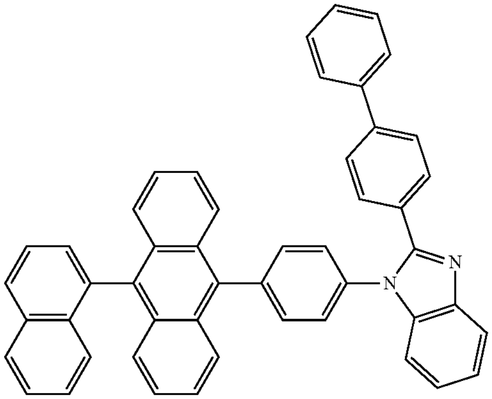
<ETMB-21>
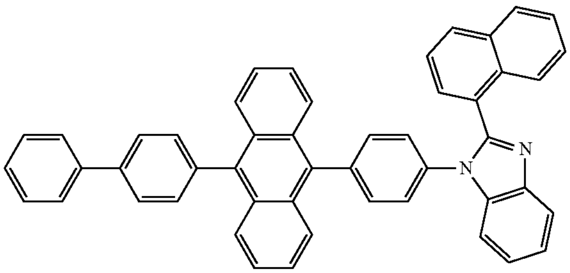
-continued
<ETMB-22>
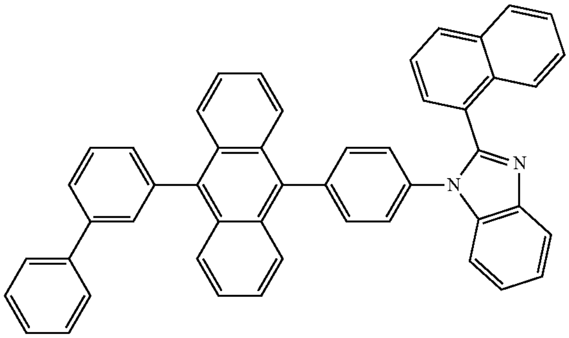
<ETMB-23>
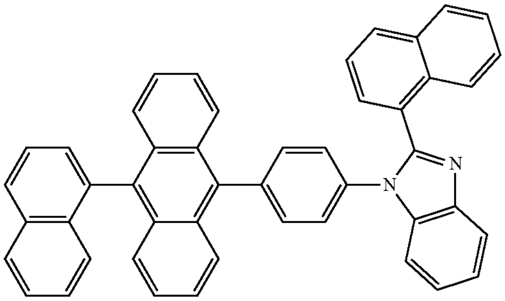
<ETMB-24>
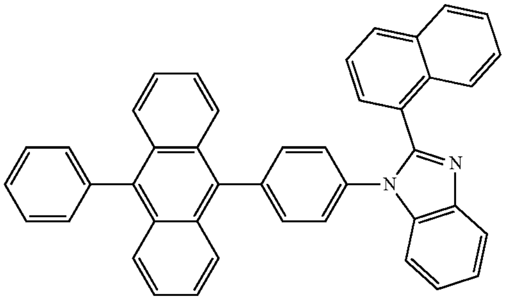
<ETMB-25>
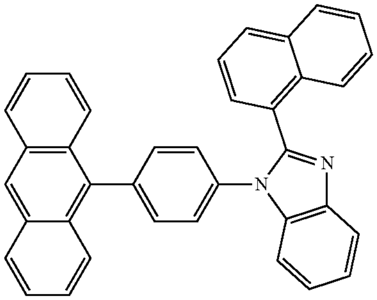

-continued
<ETMB-26>
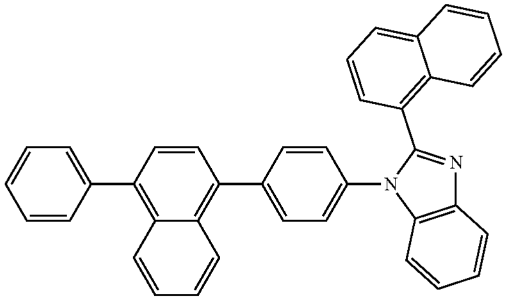
<ETMB-27>
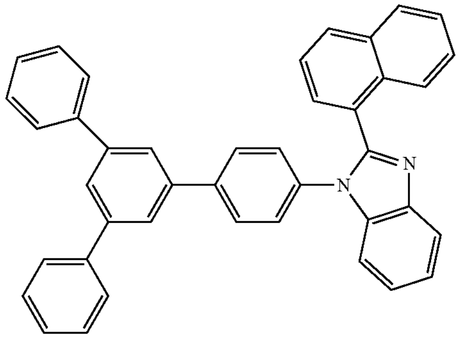
<ETMB-28>
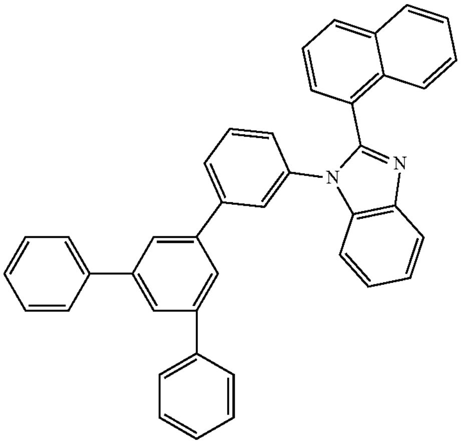
<ETMB-29>
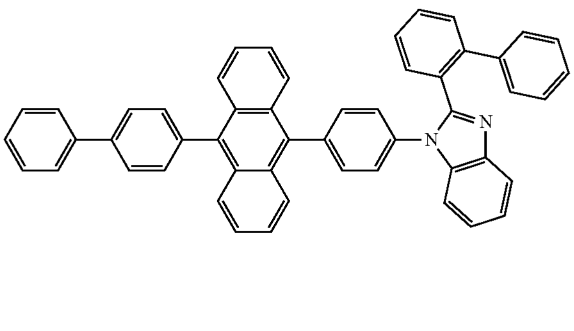
-continued
<ETMB-30>
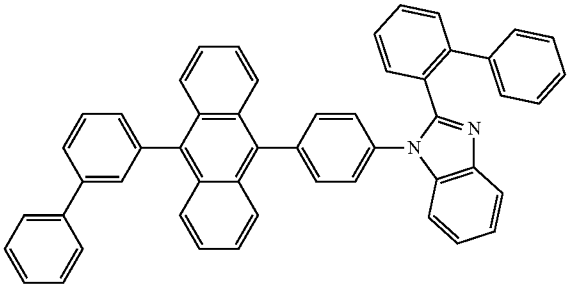
<ETMB-31>
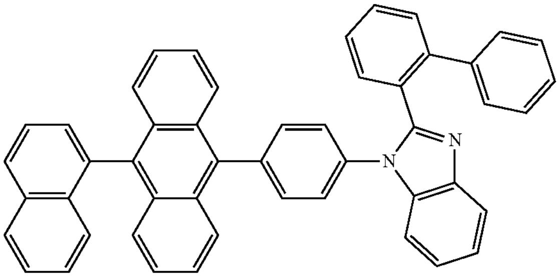
<ETMB-32>
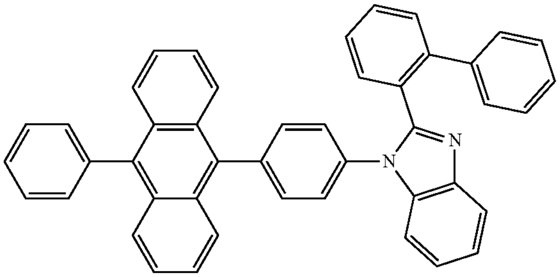
<ETMB-33>
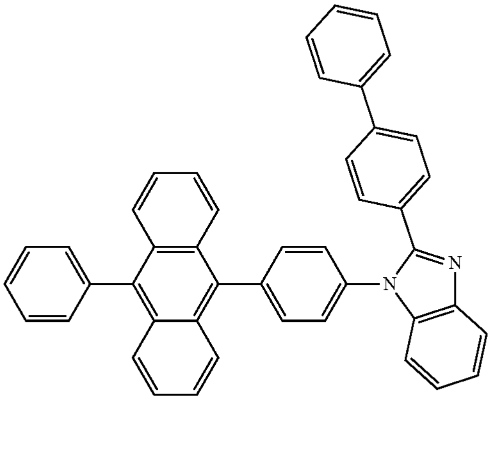

-continued

<ETMB-34>

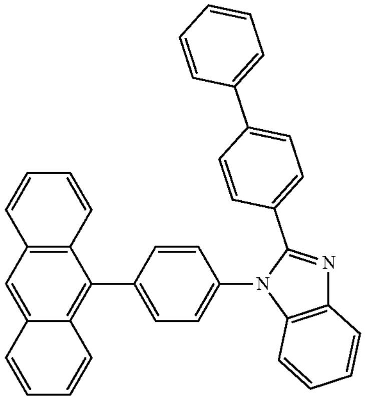

<ETMB-35>

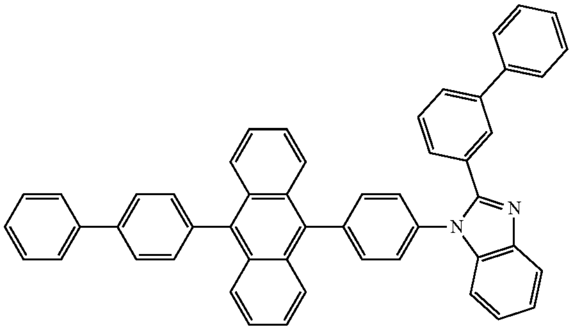

<ETMB-36>

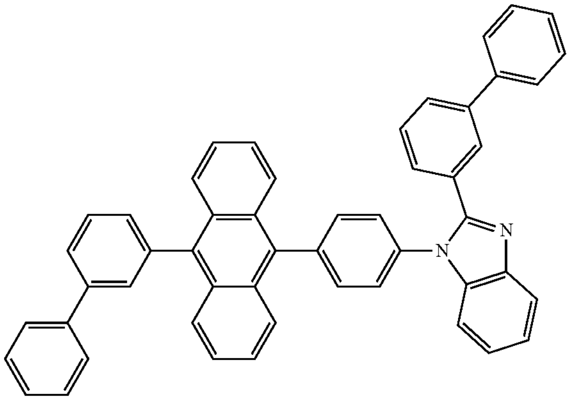

<ETMB-37>

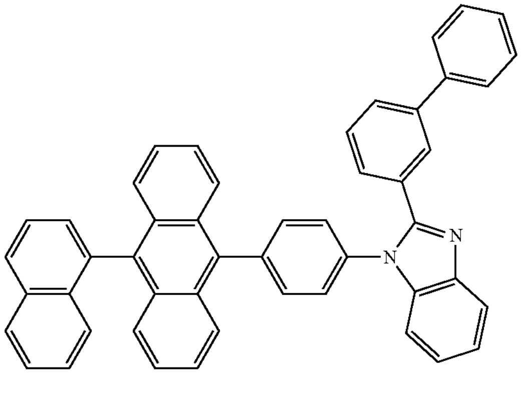

-continued

<ETMB-38>

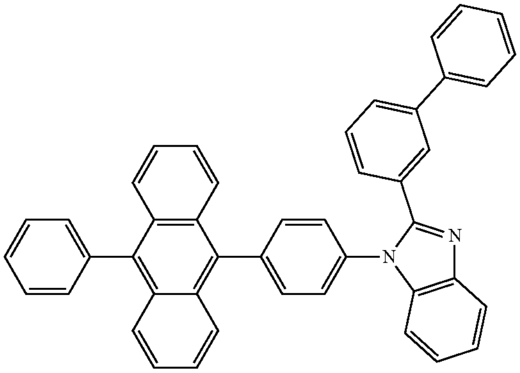

<ETMB-39>

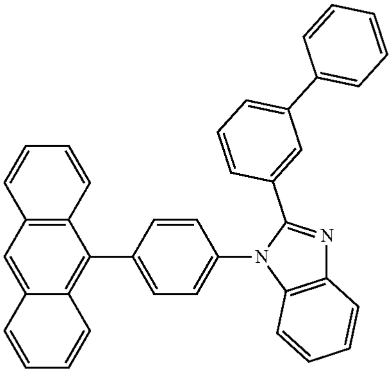

<ETMB-40>

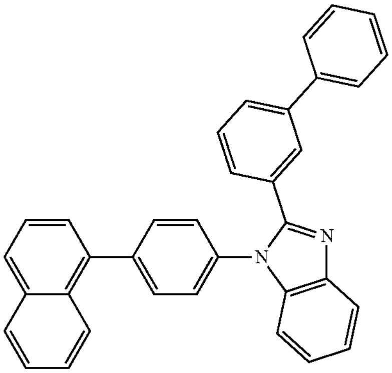

Figure 3:
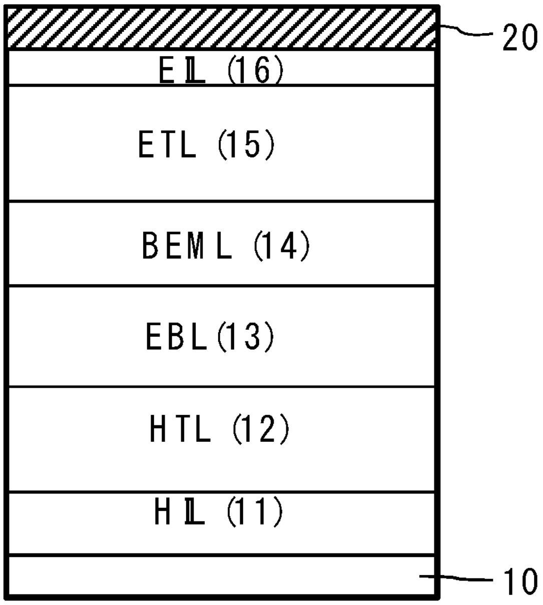
FIG. 3 is a cross-sectional view illustrating the light emitting device used in the first to fourth experimental example groups.

FIG. 3 is a cross-sectional view illustrating the light emitting devices used in the first to fourth experimental example groups.

Experiments in the first to fourth experimental example groups were conducted to determine the change in the blue fluorescent stack adjacent to the cathode and were carried out in a unit fluorescent stack that was not connected to a phosphorescent stack, as shown in FIG. 3.

As shown in FIG. 3, the light emitting devices used for the first experimental example group (Ex1-1 to Ext-40), the second experimental example group (Ex2-1 to Ex2-60), the third experimental example group (Ex3-1 to Ex3-60), and the fourth experimental example group (Ex4-1 to Ex4-27) have the following configurations sequentially on the anode 10 formed of ITO.

That is, DNTPD of Formula 5 and $MgF_2$ were mixed at a weight ratio of 1:1 on the anode 10 and the resulting mixture was deposited to a thickness of 7.5 nm to form a hole injection layer HIL 11.

[Formula 5]

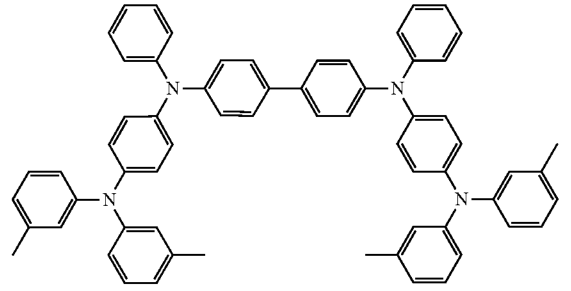

Then, α-NPD was deposited to a thickness of 80 nm on the hole injection layer 11 to form a hole transport layer HTL 12.

Then, an electron-blocking layer 13 was formed to a thickness of 20 nm on the hole transport layer 12 using TAPC of Formula 6.

[Formula 6]

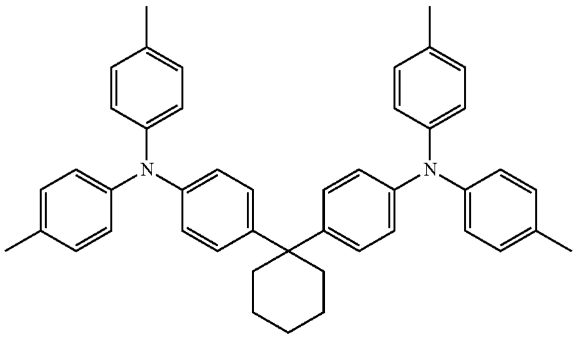

Then, MADN of Formula 7 and a boron-based dopant of DABNA-1 of Formula 8 were doped at 3 wt % on the electron-blocking layer 13 to form a blue light emitting layer BEML 14 having a thickness of 30 nm.

[Formula 7]

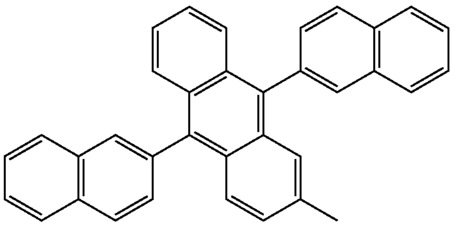

[Formula 8]

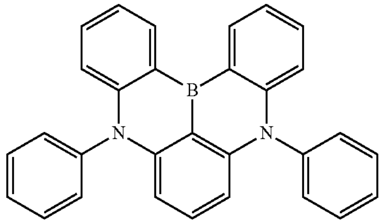

Then, in each experimental example of the first experimental example groups (Ex1-1 to Ext-40), an electron transport layer ETL 15 having a thickness of 25 nm was formed using the second material C2 (ETMB-01 to ETMB-40) of Formula 2 as a single material. By the same process, in the second experimental example group (Ex2-1 to Ex2-60), the electron transport layer 15 was formed to a thickness of 25 nm using the first material C1 (ETM-01 to ETM-60) of Formula 1 as a single material. Meanwhile, in the third experimental example group (Ex3-1 to Ex3-60), the first material C1 and the second material C2 were mixed at a weight ratio of 5:5, and the resulting mixture was used to form an electron transport layer 15 having a thickness of 25 nm. In the fourth experimental example group (Ex4-1 to Ex4-27), the weight ratio of the second material C2 to the first material C1 was changed to the range from 1:9 to 9:1 to form an electron transport layer 15 having a thickness of 25 nm.

Then, an electron injection layer EIL 16 having a thickness of 2 nm was formed using LiF on the electron transport layer 15. Then, a cathode 20 made of an aluminum (Al) component was formed on the electron injection layer 16.

First, in the first experimental example group (Ex1-1 to Ext-40) of Table 1, in the light emitting device structure of FIG. 3, the material of the electron transport layer 15 was a single material of Formula 2, and was one of ETMB-01 to ETMB-40, and the turn-on voltage at a luminance of 0.1 $Cd/m^2$, the driving voltage at a current density of 10 $mA/cm^2$, the driving voltage at a current density of 100 $mA/cm^2$, and the luminance and the external quantum efficiency at a current density of 10 $mA/cm^2$ were comparatively evaluated.

TABLE 1

| Item | ETL (C2) | Turn-on voltage [V], 0.1 $Cd/m^2$ | Voltage [V] at 10 $mA/cm^2$ | Voltage [V] at 100 $mA/cm^2$ | Luminance [Cd/A] at 10 $mA/cm^2$ | EQE (%) at 10 $mA/cm^2$ |
|---|---|---|---|---|---|---|
| Ex1-1 | ETMB-01 | 2.83 | 3.95 | 4.71 | 3.9 | 6.3 |
| Ex1-2 | ETMB-02 | 2.76 | 3.95 | 4.74 | 3.1 | 5.0 |
| Ex1-3 | ETMB-03 | 2.84 | 3.99 | 4.67 | 3.2 | 5.1 |
| Ex1-4 | ETMB-04 | 2.88 | 3.84 | 4.77 | 2.8 | 4.6 |

TABLE 1-continued

| Item | ETL (C2) | Turn-on voltage [V], 0.1 Cd/m$^2$ | Voltage [V] at 10 mA/cm$^2$ | Voltage [V] at 100 mA/cm$^2$ | Luminance [Cd/A] at 10 mA/cm$^2$ | EQE (%) at 10 mA/cm$^2$ |
|---|---|---|---|---|---|---|
| Ex1-5 | ETMB-05 | 2.78 | 4.02 | 4.70 | 4.2 | 6.7 |
| Ex1-6 | ETMB-06 | 2.83 | 4.06 | 5.53 | 2.7 | 4.4 |
| Ex1-7 | ETMB-07 | 2.77 | 4.24 | 5.83 | 3.8 | 6.1 |
| Ex1-8 | ETMB-08 | 2.71 | 4.27 | 5.63 | 3.1 | 5.0 |
| Ex1-9 | ETMB-09 | 2.74 | 3.75 | 4.72 | 3.8 | 6.1 |
| Ex1-10 | ETMB-10 | 2.77 | 3.76 | 4.85 | 2.9 | 4.7 |
| Ex1-11 | ETMB-11 | 2.78 | 4.06 | 4.99 | 4.2 | 6.7 |
| Ex1-12 | ETMB-12 | 2.71 | 3.83 | 4.90 | 3.9 | 6.3 |
| Ex1-13 | ETMB-13 | 2.74 | 4.08 | 4.86 | 2.9 | 4.7 |
| Ex1-14 | ETMB-14 | 2.84 | 4.06 | 5.03 | 4.3 | 7.0 |
| Ex1-15 | ETMB-15 | 2.74 | 4.48 | 5.78 | 3.5 | 5.7 |
| Ex1-16 | ETMB-16 | 2.80 | 4.33 | 5.80 | 3.2 | 5.2 |
| Ex1-17 | ETMB-17 | 2.79 | 3.86 | 4.78 | 3.9 | 6.2 |
| Ex1-18 | ETMB-18 | 2.88 | 3.97 | 4.80 | 2.7 | 4.3 |
| Ex1-19 | ETMB-19 | 2.87 | 3.76 | 4.62 | 2.9 | 4.6 |
| Ex1-20 | ETMB-20 | 2.87 | 3.88 | 4.96 | 3.7 | 6.0 |
| Ex1-21 | ETMB-21 | 2.79 | 4.08 | 4.62 | 2.7 | 4.3 |
| Ex1-22 | ETMB-22 | 2.74 | 3.89 | 4.93 | 2.7 | 4.3 |
| Ex1-23 | ETMB-23 | 2.89 | 4.00 | 5.00 | 3.3 | 5.4 |
| Ex1-24 | ETMB-24 | 2.86 | 4.03 | 4.62 | 3.0 | 4.8 |
| Ex1-25 | ETMB-25 | 2.84 | 3.78 | 4.89 | 3.2 | 5.1 |
| Ex1-26 | ETMB-26 | 2.77 | 3.97 | 5.20 | 3.8 | 6.2 |
| Ex1-27 | ETMB-27 | 2.82 | 4.09 | 6.25 | 3.3 | 5.2 |
| Ex1-28 | ETMB-28 | 2.82 | 4.28 | 5.51 | 4.2 | 6.7 |
| Ex1-29 | ETMB-29 | 2.87 | 3.79 | 4.79 | 3.5 | 5.6 |
| Ex1-30 | ETMB-30 | 2.79 | 3.77 | 4.73 | 4.0 | 6.5 |
| Ex1-31 | ETMB-31 | 2.87 | 3.82 | 4.68 | 3.6 | 5.7 |
| Ex1-32 | ETMB-32 | 2.72 | 3.94 | 4.91 | 4.1 | 6.6 |
| Ex1-33 | ETMB-33 | 2.84 | 4.08 | 4.85 | 2.9 | 4.7 |
| Ex1-34 | ETMB-34 | 2.81 | 4.08 | 5.00 | 3.7 | 6.0 |
| Ex1-35 | ETMB-35 | 2.72 | 3.71 | 4.71 | 3.3 | 5.3 |
| Ex1-36 | ETMB-36 | 2.77 | 3.78 | 4.81 | 3.3 | 5.3 |
| Ex1-37 | ETMB-37 | 2.79 | 3.98 | 4.92 | 3.4 | 5.5 |
| Ex1-38 | ETMB-38 | 2.84 | 4.01 | 4.93 | 3.3 | 5.3 |
| Ex1-39 | ETMB-39 | 2.71 | 4.01 | 5.00 | 3.0 | 4.9 |
| Ex1-40 | ETMB-40 | 2.86 | 4.28 | 5.55 | 3.4 | 5.5 |

In the first experimental example group (Ex1-1 to Ext-40), the turn-on voltage at the luminance of 0.1 Cd/$m^2$ was 2.71V to 2.89V, the driving voltage at the current density of 10 mA/$cm^2$ was 3.71V to 4.48V, and the driving voltage at a current density of 100 mA/$cm^2$ was 4.62 V to 6.25 V. In addition, the luminance at a current density of 10 mA/$cm^2$ was 2.7 Cd/A to 4.3 Cd/A, and the external quantum efficiency was 4.3% to 7.0%. In the second experimental example group (Ex2-1 to Ext-60) of Table 2, in the structure of the light emitting device of FIG. 3, the material of the electron transport layer 15 was a single material of Formula 1, the material was changed from ETM-01 to ETM-60, and the turn-on voltage at a luminance of 0.1 Cd/$m^2$, the driving voltage at a current density of 10 mA/$cm^2$, the driving voltage at a current density of 100 mA/$cm^2$, and the luminance and external quantum efficiency at a current density of 10 mA/$cm^2$ were comparatively evaluated.

TABLE 2

| Item | ETL (C1) | Turn-on voltage [V] at 0.1 Cd/$m^2$ | Voltage [V] at 10 mA/$cm^2$ | Voltage [V] at 100 mA/$cm^2$ | Luminance [Cd/A] at 10 mA/$cm^2$ | EQE (%) at 10 mA/$cm^2$ |
|---|---|---|---|---|---|---|
| Ex2-1 | ETM-01 | 4.25 | 5.52 | 8.57 | 4.3 | 6.9 |
| Ex2-2 | ETM-02 | 4.17 | 5.55 | 8.59 | 3.3 | 5.3 |
| Ex2-3 | ETM-03 | 4.29 | 5.51 | 8.35 | 3.8 | 6.1 |
| Ex2-4 | ETM-04 | 4.20 | 5.70 | 8.65 | 3.7 | 5.9 |
| Ex2-5 | ETM-05 | 4.20 | 5.64 | 8.42 | 4.3 | 7.0 |
| Ex2-6 | ETM-06 | 4.13 | 5.59 | 8.44 | 2.7 | 4.4 |
| Ex2-7 | ETM-07 | 4.25 | 5.64 | 8.67 | 4.2 | 6.7 |
| Ex2-8 | ETM-08 | 4.16 | 5.42 | 8.52 | 2.6 | 4.2 |
| Ex2-9 | ETM-09 | 4.15 | 5.46 | 8.60 | 2.7 | 4.3 |
| Ex2-10 | ETM-10 | 4.29 | 5.54 | 8.60 | 3.7 | 6.0 |
| Ex2-11 | ETM-11 | 4.29 | 5.80 | 8.56 | 2.9 | 4.7 |
| Ex2-12 | ETM-12 | 4.23 | 5.58 | 8.45 | 3.5 | 5.7 |
| Ex2-13 | ETM-13 | 4.27 | 5.80 | 8.54 | 3.3 | 5.4 |
| Ex2-14 | ETM-14 | 4.12 | 5.40 | 8.48 | 4.0 | 6.5 |
| Ex2-15 | ETM-15 | 4.28 | 5.44 | 8.56 | 4.3 | 6.8 |
| Ex2-16 | ETM-16 | 4.27 | 5.72 | 8.47 | 4.2 | 6.8 |
| Ex2-17 | ETM-17 | 4.17 | 5.44 | 8.46 | 2.9 | 4.6 |
| Ex2-18 | ETM-18 | 4.20 | 5.70 | 8.69 | 3.2 | 5.1 |
| Ex2-19 | ETM-19 | 4.10 | 5.42 | 8.64 | 3.7 | 5.9 |
| Ex2-20 | ETM-20 | 4.10 | 5.45 | 8.57 | 4.2 | 6.8 |
| Ex2-21 | ETM-21 | 4.16 | 5.55 | 8.54 | 3.4 | 5.4 |
| Ex2-22 | ETM-22 | 4.18 | 5.75 | 8.70 | 3.4 | 5.5 |
| Ex2-23 | ETM-23 | 4.15 | 5.76 | 8.34 | 3.7 | 6.0 |
| Ex2-24 | ETM-24 | 4.14 | 5.72 | 8.50 | 3.4 | 5.5 |
| Ex2-25 | ETM-25 | 4.12 | 5.69 | 8.58 | 4.2 | 6.7 |
| Ex2-26 | ETM-26 | 4.24 | 5.60 | 8.34 | 2.7 | 4.4 |
| Ex2-27 | ETM-27 | 4.13 | 5.48 | 8.63 | 2.6 | 4.1 |
| Ex2-28 | ETM-28 | 4.23 | 5.45 | 8.46 | 4.1 | 6.7 |
| Ex2-29 | ETM-29 | 4.12 | 5.50 | 8.45 | 3.0 | 4.9 |
| Ex2-30 | ETM-30 | 4.24 | 5.46 | 8.32 | 3.4 | 5.4 |
| Ex2-31 | ETM-31 | 4.11 | 5.66 | 8.70 | 2.7 | 4.3 |
| Ex2-32 | ETM-32 | 4.22 | 5.59 | 8.31 | 2.7 | 4.4 |
| Ex2-33 | ETM-33 | 4.27 | 5.55 | 8.61 | 3.9 | 6.3 |
| Ex2-34 | ETM-34 | 4.20 | 5.76 | 8.58 | 4.2 | 6.7 |
| Ex2-35 | ETM-35 | 4.17 | 5.51 | 8.59 | 3.3 | 5.4 |
| Ex2-36 | ETM-36 | 4.19 | 5.60 | 8.35 | 3.8 | 6.0. |
| Ex2-37 | ETM-37 | 4.20 | 5.79 | 8.41 | 4.2 | 6.8 |
| Ex2-38 | ETM-38 | 4.27 | 5.50 | 8.45 | 2.6 | 4.2 |
| Ex2-39 | ETM-39 | 4.20 | 5.55 | 8.43 | 3.7 | 5.9 |
| Ex2-40 | ETM-40 | 4.25 | 5.60 | 8.70 | 2.8 | 4.6 |
| Ex2-41 | ETM-41 | 4.16 | 5.72 | 8.70 | 3.8 | 6.2 |
| Ex2-42 | ETM-42 | 4.21 | 5.48 | 8.65 | 3.6 | 5.7 |
| Ex2-43 | ETM-43 | 4.12 | 5.56 | 8.52 | 4.3 | 6.9 |
| Ex2-44 | ETM-44 | 4.27 | 5.45 | 8.31 | 3.6 | 5.8 |
| Ex2-45 | ETM-45 | 4.21 | 5.45 | 8.45 | 3.2 | 5.2 |
| Ex2-46 | ETM-46 | 4.26 | 5.73 | 8.42 | 4.1 | 6.6 |
| Ex2-47 | ETM-47 | 4.21 | 5.62 | 8.48 | 2.6 | 4.2 |
| Ex2-48 | ETM-48 | 4.29 | 5.44 | 8.62 | 3.6 | 5.8 |
| Ex2-49 | ETM-49 | 4.27 | 5.55 | 8.35 | 3.2 | 5.1 |
| Ex2-50 | ETM-50 | 4.12 | 5.73 | 8.35 | 3.9 | 6.3 |
| Ex2-51 | ETM-51 | 4.18 | 5.66 | 8.34 | 2.8 | 4.5 |
| Ex2-52 | ETM-52 | 4.27 | 5.46 | 8.38 | 4.3 | 6.8 |
| Ex2-53 | ETM-53 | 4.25 | 5.79 | 8.52 | 2.7 | 4.3 |
| Ex2-54 | ETM-54 | 4.11 | 5.42 | 8.53 | 4.0 | 6.5 |
| Ex2-55 | ETM-55 | 4.18 | 5.63 | 8.57 | 3.1 | 5.0 |
| Ex2-56 | ETM-56 | 4.27 | 5.46 | 8.38 | 4.2 | 6.8 |
| Ex2-57 | ETM-57 | 4.14 | 5.47 | 8.66 | 2.7 | 4.4 |
| Ex2-58 | ETM-58 | 4.15 | 5.52 | 8.67 | 3.7 | 6.0 |
| Ex2-59 | ETM-59 | 4.12 | 5.51 | 8.60 | 3.4 | 5.5 |
| Ex2-60 | ETM-60 | 4.21 | 5.59 | 8.54 | 2.7 | 4.3 |

In the second experimental example group (Ex2-1 to Ex2-60), the turn-on voltage at a luminance of 0.1 Cd/$m^2$ was 4.10V to 4.29V, the driving voltage at a current density of 10 mA/$cm^2$ was 5.40V to 5.80V, and the driving voltage at a current density of 100 mA/$cm^2$ was 8.31V to 8.70V. The luminance at a current density of 10 mA/$cm^2$ was 2.6 Cd/A to 4.3 Cd/A, and the external quantum efficiency at a current density of 10 mA/$cm^2$ was 4.1% to 7.0%.

Comparing the first experimental example group (Ex1-1 to Ext-40) with the second experimental example group (Ex2-1 to Ex2-60), the luminance and external quantum efficiency were similar, but the second experimental example group (Ex1-1 to Ex2-60) exhibited an increase in both turn-on voltage and driving voltage.

Figure 4A:
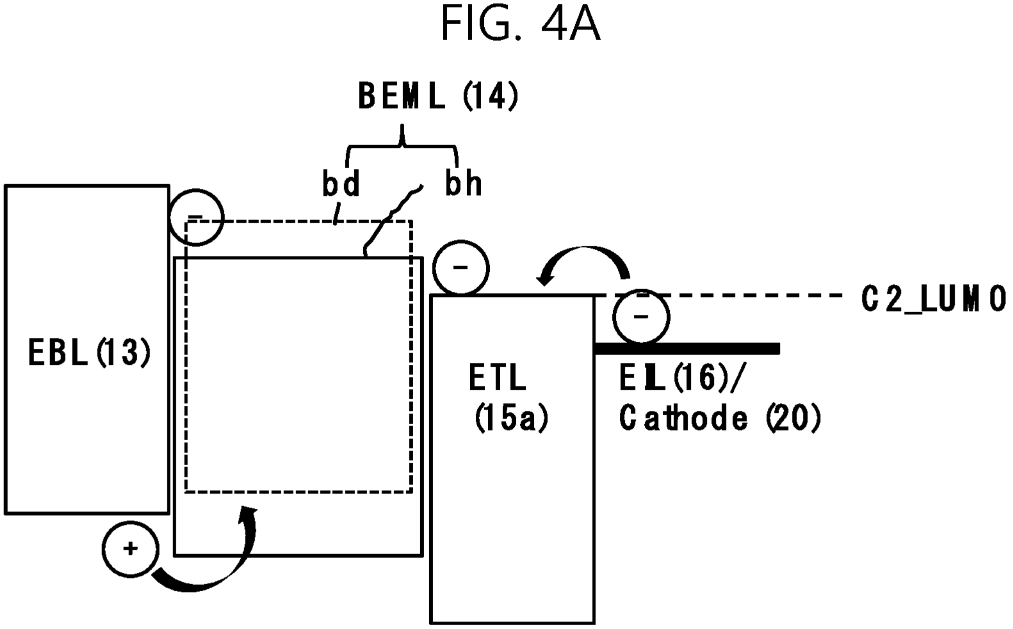
FIGS. 4A and 4B are energy band diagrams illustrating hole and electron transport characteristics of a blue light emitting layer and surrounding layers when a second material and a first material, evaluated in a first experimental example group and a second experimental example group, are respectively used for an electron transport layer adjacent to the cathode according to one embodiment.
Figure 4B:
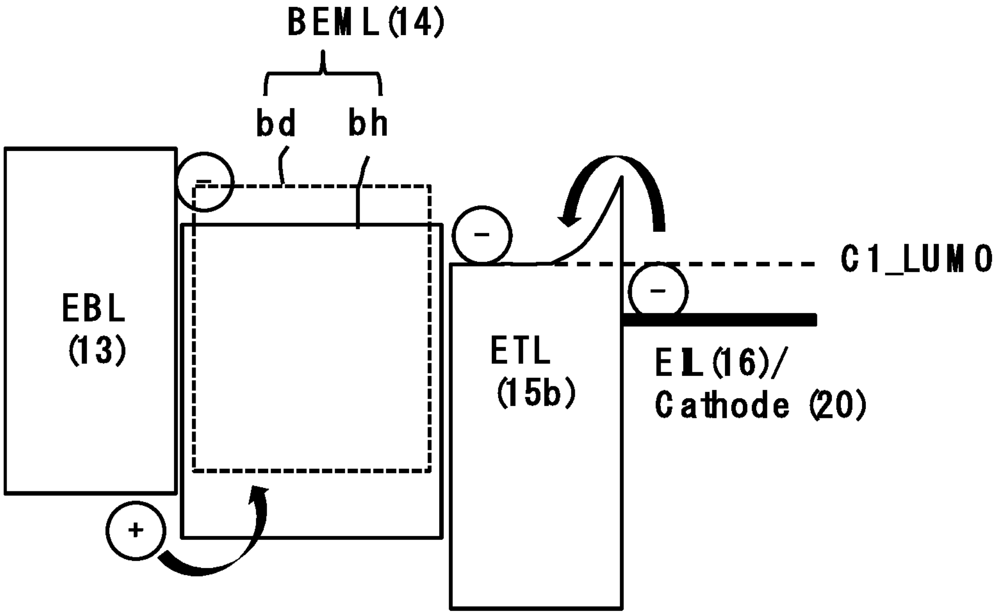

FIGS. 4A and 4B illustrate energy band diagrams illustrating hole and electron transport properties of a blue light emitting layer and surrounding layers when the second material and the first material, reviewed through the first experimental example group and the second experimental example group, are used as the electron transport layer adjacent to the cathode.

As can be seen from the results of Table 1 and FIG. 4A, the electron transport layer 15*a* using the second material C2 of Formula 2 of the first experimental example group (Ex1-1 to Ext-40) has a small difference between the work function of the electron injection layer 16 and the cathode 20 and the LUMO energy level of the second material C2 itself, and is capable of transporting electrons smoothly. In addition, in the first experimental example group (Ex1-1 to Ext-40), there is little or no repulsive force when the second material C2 reacts with a lithium compound, so even when voltage is supplied to the cathode 20, the electron transport layer 15*a* exhibits excellent electron injection properties without change in the energy barrier when the electrons are supplied to the second material C2.

Meanwhile, as can be seen from the results of Table 2 and FIG. 4B, in the electron transport layer 15*b* containing the first material C1 used for the second experimental example group Ex2-1 to Ex2-60, the first material C1 of Formula 1, in the initial state when no voltage is applied, has a LUMO energy level similar to that of the second material C2 and has a high electron transport ability, but has a large force repelling the lithium compound constituting the electron injection layer 16, increases the energy barrier at the interface with the electron injection layer 16 compared to the intrinsic LUMO energy level when the voltage is supplied to the cathode 20, and exhibits an increase in turn-on voltage and driving voltage in supplying electrons.

In consideration of the results of the first and second experimental example groups, the present inventors conducted experiments with respect to the third experimental example group and the fourth experimental example group that include formation of an electron transport layer 15 using a mixture of the first material C1 that has high electron transport ability and the second material C2 that has no repulsive force against the material constituting the electron injection layer 16 and facilitates electron injection.

In the third experimental example group (Ex3-1 to Ex3-60) of Table 3, in the structure of the light emitting device of FIG. 3, the electron transport layer 15 is formed by co-depositing a mixture of the second material C2 of Formula 2 and the first material C1 of Formula 1 at a weight ratio of 1:1. As shown in Table 3, the second material C2 is changed to ETMB-04, ETMB-09, ETMB-12, or ETMB-17, and the first material C1 is changed to ETM-01, ETM-02, ETM-07, ETM-08, ETM-13, ETM-16, ETM-17, ETM-19, ETM-21, ETM-22, ETM-30, ETM-38, ETM-41, ETM-50, or ETM-53. In each of the experimental examples, the turn-on voltage at a luminance of 0.1 Cd/$m^2$, the driving voltage at a current density of 10 mA/$cm^2$, the driving voltage at a current density of 100 mA/$cm^2$, and the luminance and the external quantum efficiency at a current density of 10 mA/$cm^2$ were comparatively evaluated.

TABLE 3

| | ETL (C2 + 1) | | Turn-on voltage [V] at | Voltage [V] at 10 | Voltage [V] at | Luminance [Cd/A | EQE (%) at |
|---|---|---|---|---|---|---|---|
| Item | C2 | C1 | 0.1 Cd/$m^2$ | mA/$cm^2$ | 100 mA/$cm^2$ | at 10 mA/$cm^2$ | 10 mA/$cm^2$ |
| Ex3-1 | ETMB-04 | ETM-01 | 2.75 | 4.00 | 4.70 | 5.4 | 8.7 |
| Ex3-2 | ETMB-04 | ETM-02 | 2.82 | 3.88 | 4.82 | 5.5 | 8.9 |
| Ex3-3 | ETMB-04 | ETM-07 | 2.87 | 3.72 | 4.97 | 5.6 | 9.1 |
| Ex3-4 | ETMB-04 | ETM-08 | 2.76 | 3.90 | 4.67 | 5.6 | 8.9 |
| Ex3-5 | ETMB-04 | ETM-13 | 2.71 | 3.60 | 4.96 | 5.6 | 9.1 |
| Ex3-6 | ETMB-04 | ETM-16 | 2.79 | 3.98 | 4.66 | 5.7 | 9.2 |
| Ex3-7 | ETMB-04 | ETM-17 | 2.80 | 3.73 | 4.82 | 5.4 | 8.7 |
| Ex3-8 | ETMB-04 | ETM-19 | 2.72 | 3.90 | 4.97 | 5.7 | 9.2 |
| Ex3-9 | ETMB-04 | ETM-21 | 2.85 | 3.93 | 4.68 | 5.8 | 9.4 |
| Ex3-10 | ETMB-04 | ETM-22 | 2.81 | 3.90 | 4.85 | 5.6 | 8.9 |
| Ex3-11 | ETMB-04 | ETM-30 | 2.85 | 3.96 | 4.83 | 5.6 | 9.0 |
| Ex3-12 | ETMB-04 | ETM-38 | 2.89 | 3.67 | 4.74 | 5.6 | 9.1 |
| Ex3-13 | ETMB-04 | ETM-41 | 2.75 | 3.98 | 4.88 | 5.8 | 9.3 |

TABLE 3-continued

| Item | ETL (C2 + 1) C2 | C1 | Turn-on voltage [V] at 0.1 Cd/$m^2$ | Voltage [V] at 10 mA/$cm^2$ | Voltage [V] at 100 mA/$cm^2$ | Luminance [Cd/A at 10 mA/$cm^2$ | EQE (%) at 10 mA/$cm^2$ |
|---|---|---|---|---|---|---|---|
| Ex3-14 | ETMB-04 | ETM-50 | 2.84 | 3.65 | 4.63 | 5.8 | 9.4 |
| Ex3-15 | ETMB-04 | ETM-53 | 2.82 | 3.94 | 4.80 | 5.8 | 9.4 |
| Ex3-16 | ETMB-09 | ETM-01 | 2.85 | 3.87 | 4.93 | 5.4 | 8.6 |
| Ex3-17 | ETMB-09 | ETM-02 | 2.70 | 3.74 | 4.88 | 5.5 | 8.8 |
| Ex3-18 | ETMB-09 | ETM-07 | 2.77 | 3.99 | 4.98 | 5.3 | 8.5 |
| Ex3-19 | ETMB-09 | ETM-08 | 2.87 | 3.98 | 4.99 | 5.4 | 8.7 |
| Ex3-20 | ETMB-09 | ETM-13 | 2.77 | 3.82 | 4.95 | 5.6 | 9.0 |
| Ex3-21 | ETMB-09 | ETM-16 | 2.81 | 3.63 | 4.70 | 5.4 | 8.7 |
| Ex3-22 | ETMB-09 | ETM-17 | 2.76 | 3.62 | 4.86 | 5.6 | 9.1 |
| Ex3-23 | ETMB-09 | ETM-19 | 2.72 | 3.74 | 4.89 | 5.4 | 8.7 |
| Ex3-24 | ETMB-09 | ETM-21 | 2.75 | 3.73 | 4.63 | 5.3 | 8.5 |
| Ex3-25 | ETMB-09 | ETM-22 | 2.75 | 3.68 | 4.78 | 5.6 | 9.0 |
| Ex3-26 | ETMB-09 | ETM-30 | 2.88 | 3.61 | 4.88 | 5.3 | 8.6 |
| Ex3-27 | ETMB-09 | ETM-38 | 2.85 | 3.85 | 4.87 | 5.7 | 9.1 |
| Ex3-28 | ETMB-09 | ETM-41 | 2.70 | 3.98 | 4.74 | 5.3 | 8.5 |
| Ex3-29 | ETMB-09 | ETM-50 | 2.71 | 3.94 | 4.75 | 5.9 | 9.4 |
| Ex3-30 | ETMB-09 | ETM-53 | 2.72 | 3.67 | 4.64 | 5.7 | 9.1 |
| Ex3-31 | ETMB-12 | ETM-01 | 2.89 | 3.63 | 4.96 | 5.5 | 8.8 |
| Ex3-32 | ETMB-12 | ETM-02 | 2.76 | 3.92 | 4.66 | 5.8 | 9.4 |
| Ex3-33 | ETMB-12 | ETM-07 | 2.84 | 3.91 | 4.73 | 5.6 | 9.0 |
| Ex3-34 | ETMB-12 | ETM-08 | 2.83 | 3.79 | 4.83 | 5.9 | 9.4 |
| Ex3-35 | ETMB-12 | ETM-13 | 2.87 | 3.74 | 4.88 | 5.8 | 9.2 |
| Ex3-36 | ETMB-12 | ETM-16 | 2.75 | 3.61 | 4.80 | 5.7 | 9.1 |
| Ex3-37 | ETMB-12 | ETM-17 | 2.87 | 3.74 | 4.80 | 5.7 | 9.1 |
| Ex3-38 | ETMB-12 | ETM-19 | 2.72 | 3.77 | 4.72 | 5.4 | 8.7 |
| Ex3-39 | ETMB-12 | ETM-21 | 2.77 | 3.78 | 5.01 | 5.9 | 9.4 |
| Ex3-40 | ETMB-12 | ETM-22 | 2.79 | 3.75 | 4.77 | 5.7 | 9.1 |
| Ex3-41 | ETMB-12 | ETM-30 | 2.74 | 3.95 | 4.74 | 5.9 | 9.4 |
| Ex3-42 | ETMB-12 | ETM-38 | 2.75 | 3.75 | 4.82 | 5.4 | 8.6 |
| Ex3-43 | ETMB-12 | ETM-41 | 2.81 | 3.90 | 4.76 | 5.6 | 9.0 |
| Ex3-44 | ETMB-12 | ETM-50 | 2.80 | 3.67 | 4.90 | 5.8 | 9.3 |
| Ex3-45 | ETMB-12 | ETM-53 | 2.78 | 3.84 | 4.75 | 5.6 | 8.9 |
| Ex3-46 | ETMB-17 | ETM-01 | 2.84 | 3.90 | 4.95 | 5.5 | 8.9 |
| Ex3-47 | ETMB-17 | ETM-02 | 2.83 | 3.86 | 4.65 | 5.5 | 8.8 |

TABLE 3-continued

| Item | ETL (C2 + 1) C2 | C1 | Turn-on voltage [V] at 0.1 Cd/m$^2$ | Voltage [V] at 10 mA/cm$^2$ | Voltage [V] at 100 mA/cm$^2$ | Luminance [Cd/A at 10 mA/cm$^2$ | EQE (%) at 10 mA/cm$^2$ |
|---|---|---|---|---|---|---|---|
| Ex3-48 | ETMB-17 | ETM-07 | 2.77 | 3.87 | 4.78 | 5.5 | 8.9 |
| Ex3-49 | ETMB-17 | ETM-08 | 2.83 | 3.74 | 4.92 | 5.5 | 8.9 |
| Ex3-50 | ETMB-17 | ETM-13 | 2.81 | 3.87 | 4.88 | 5.4 | 8.7 |
| Ex3-51 | ETMB-17 | ETM-16 | 2.75 | 3.63 | 4.65 | 5.4 | 8.8 |
| Ex3-52 | ETMB-17 | ETM-17 | 2.82 | 3.71 | 4.88 | 5.4 | 8.6 |
| Ex3-53 | ETMB-17 | ETM-19 | 2.82 | 3.84 | 4.90 | 5.6 | 9.0 |
| Ex3-54 | ETMB-17 | ETM-21 | 2.87 | 3.89 | 4.69 | 5.6 | 9.0 |
| Ex3-55 | ETMB-17 | ETM-22 | 2.84 | 3.93 | 4.89 | 5.6 | 9.1 |
| Ex3-56 | ETMB-17 | ETM-30 | 2.77 | 3.85 | 5.00 | 5.5 | 8.8 |
| Ex3-57 | ETMB-17 | ETM-38 | 2.85 | 3.95 | 4.98 | 5.7 | 9.2 |
| Ex3-58 | ETMB-17 | ETM-41 | 2.77 | 3.83 | 4.98 | 5.6 | 9.0 |
| Ex3-59 | ETMB-17 | ETM-50 | 2.88 | 3.86 | 4.89 | 5.3 | 8.6 |
| Ex3-60 | ETMB-17 | ETM-53 | 2.78 | 3.78 | 4.77 | 5.3 | 8.5 |

In the third experimental example group (Ex3-1 to Ex3-60), the turn-on voltage at a luminance of 0.1 Cd/m$^2$ was 2.70V to 2.89V, the driving voltage at a current density of 10 mA/cm$^2$ was 3.60V to 4.00V, and the driving voltage at a current density of 100 mA/cm$^2$ was 4.63 V to 5.01 V. In addition, the luminance at a current density of 10 mA/cm$^2$ was 5.3 Cd/A to 5.9 Cd/A and the external quantum efficiency was 8.5 to 9.4%. The results showed that the third experimental example group (Ex3-1 to Ex3-60) exhibited a turn-on voltage at a luminance of 0.1 Cd/m$^2$ of 2.70V to 2.89V, which had a small variation range of 0.19 V or less, and was not greater than those of the first experimental example group (Ex1-1 to Ext-40), and the remaining driving voltages, which had a small variation range and were not large compared to the first experimental example group (Ex1-1 to Ext-40). In addition, the results showed that both the luminance efficiency and external quantum efficiency of the third experimental example group (Ex3-1 to Ex3-60) were improved compared to the first experimental example group (Ex1-1 to Ext-40), and the improvement was up to 2 fold. The results of the third experimental example group (Ex3-1 to Ex3-60) showed that the turn-on voltage was 2.8V on average, which was decreased to 66% of the turn-on voltage, 4.2V, of the second experimental example group (Ex2-1 to Ex2-60), and the remaining driving voltage was also significantly decreased in the third experimental example group (Ex3-1 to Ex3-60). In addition, the luminance efficiency or external quantum efficiency of the third experimental example group (Ex3-1 to Ex3-60) was improved compared the second experimental example group (Ex2-1 to Ex-60) and the improvement was up to 2 fold.

Figure 5A:
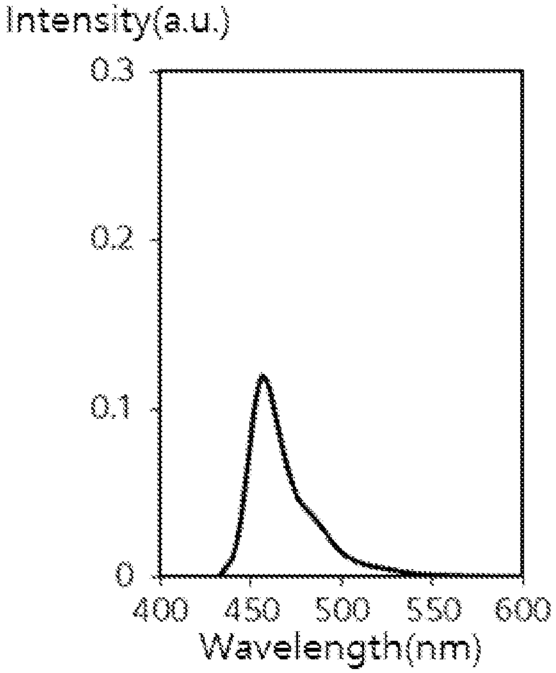
FIGS. 5A, 5B and 5C are graphs showing emission spectra of first, second and third experimental example groups, respectively, according to one embodiment.
Figure 5B:
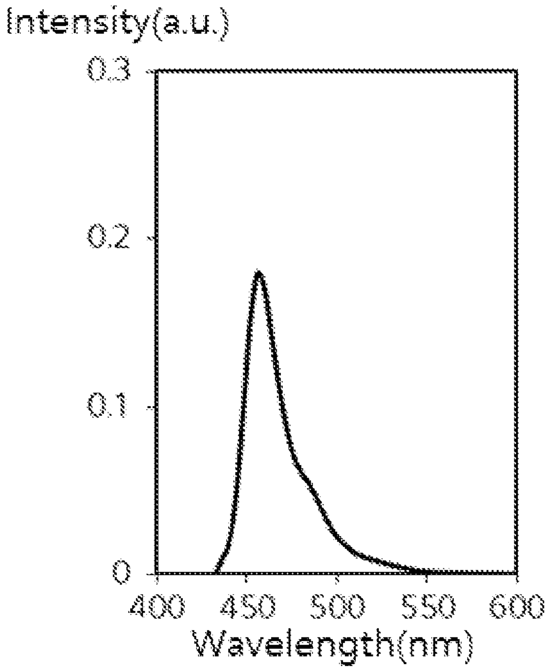
Figure 5C:
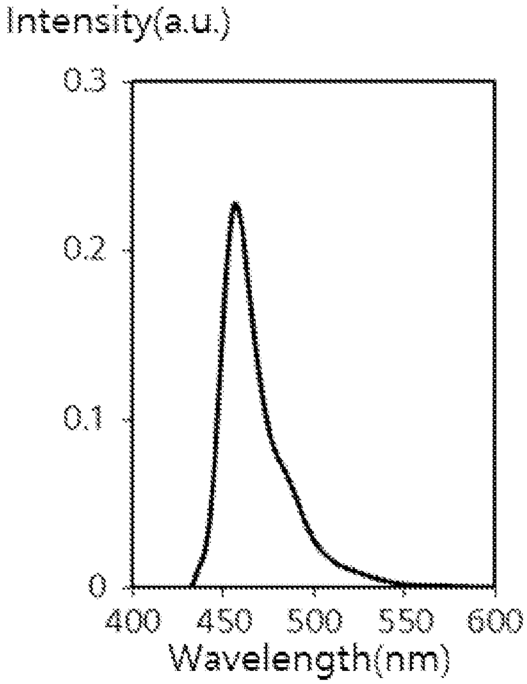

FIGS. 5A to 5C are graphs showing the emission spectra of first to third experimental example groups.

Specifically, FIG. 5A is an emission spectrum of Experimental Example Ext-4 of the first experimental example group, FIG. 5B is an emission spectrum of Experimental Example Ex2-1 of the second experimental example group, and FIG. 5C is an emission spectrum of experimental example Ex3-1 of the third experimental example group.

The results of comparison therebetween showed that the third experimental example group exhibited excellent blue light emission efficiency, as shown in FIG. 5C.

Hereinafter, a fourth experimental example group (Ex4-1 to Ex4-27), in which the electron transport layer 15 was formed by co-depositing the second material C2 and the first material C1 at different weight ratios in the structure of FIG. 3, will be described with reference to Table 4 and FIGS. 6A to 6C.

Figure 6A:
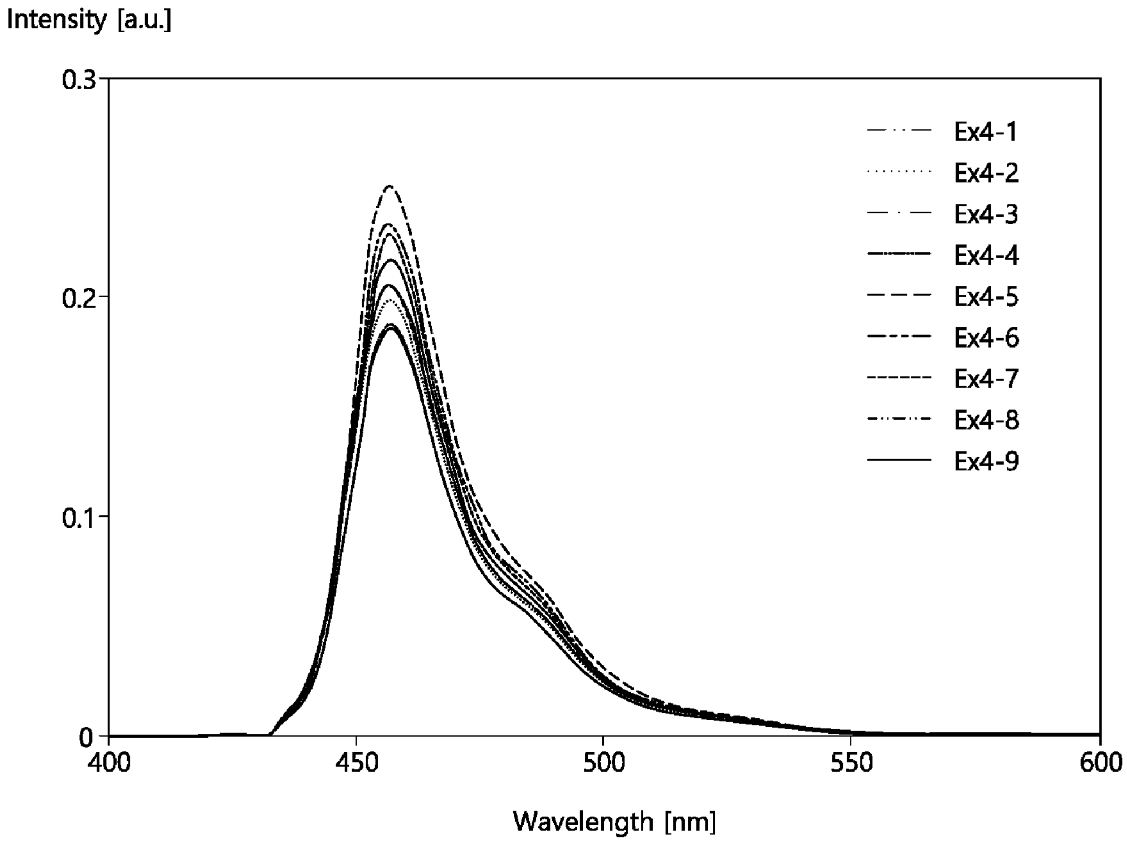
FIGS. 6A to 6C are graphs illustrating the emission spectra of a fourth experimental example group according to one embodiment.
Figure 6B:
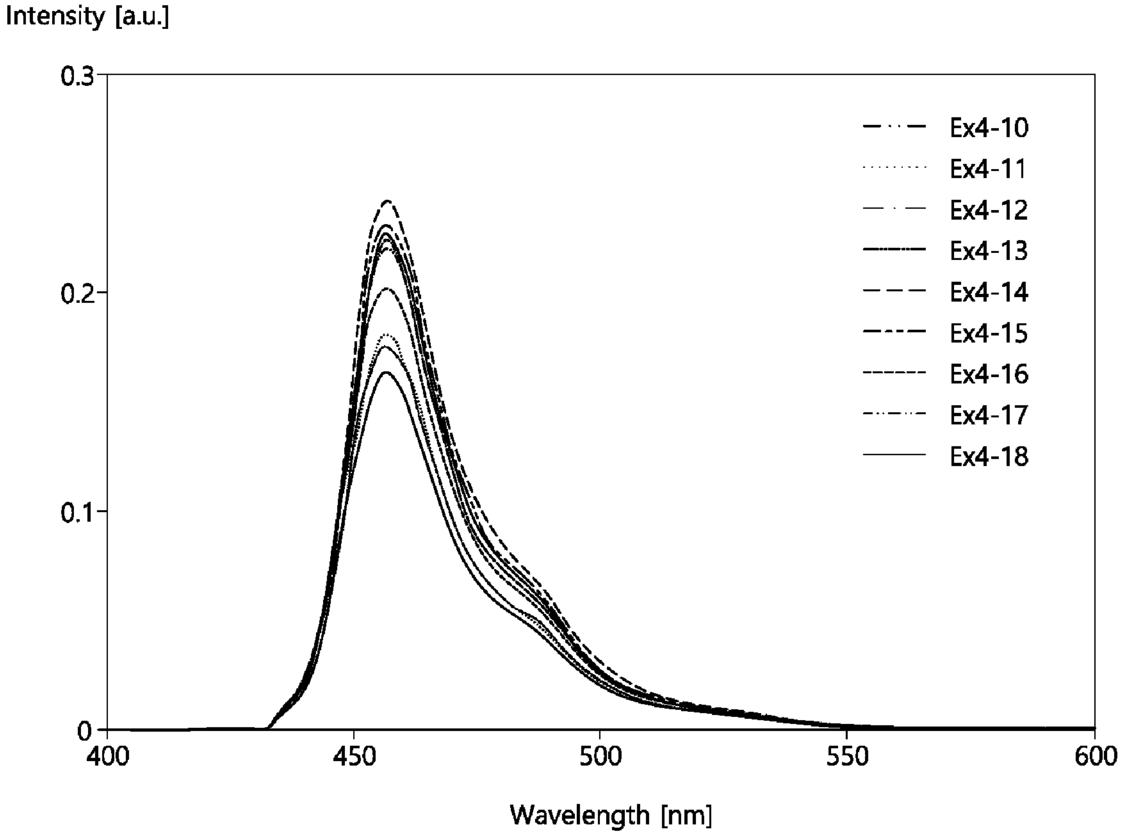
Figure 6C:
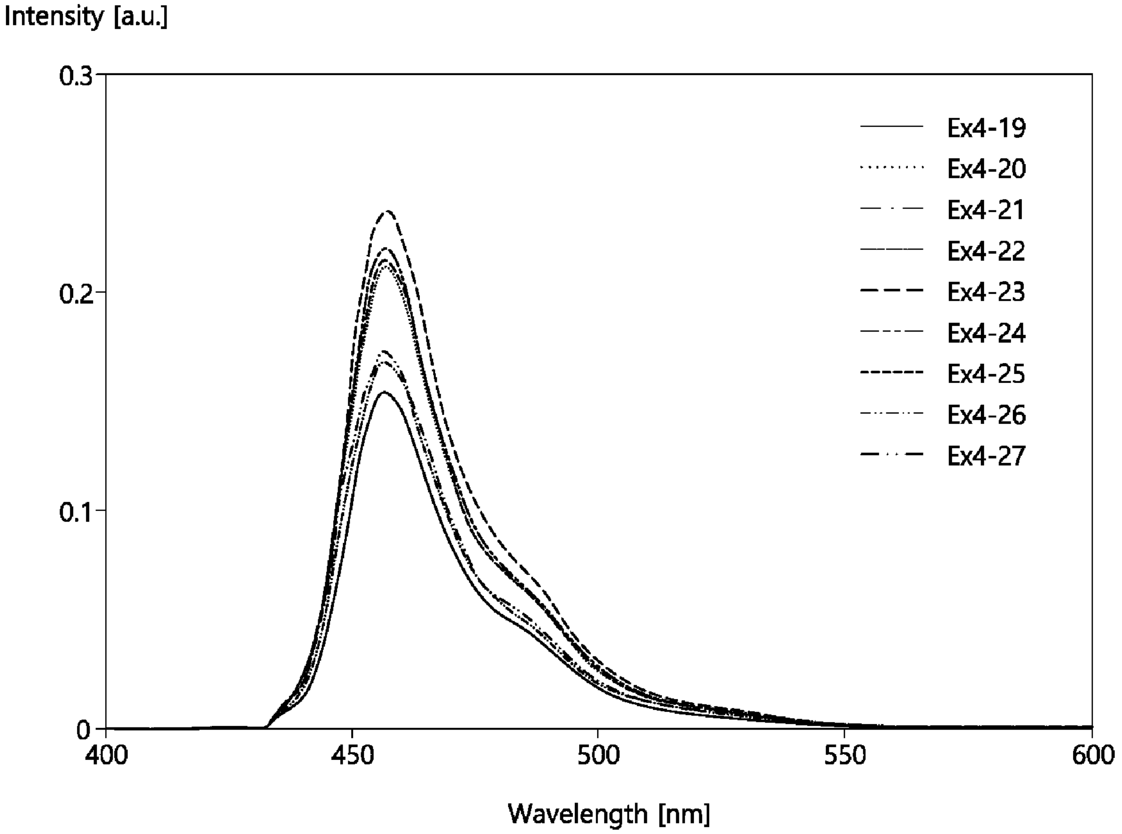

FIGS. 6A to 6C are graphs showing the emission spectra of the fourth experimental example group.

Regarding the materials for the electron transport layer 15 in the structure of the light emitting device of FIG. 3, experimental Examples Ex4-1 to Ex4-9 of the fourth experimental example group shown in Table 4 use ETMB-04 as the second material C2 and ETM-07 as the first material C1 at a weight ratio of 1:9, 2:8, 3:7, 4:6, 5:5, 6:4, 7:3, 8:2 or 9:1, which gradually increases in the ratio of the second material C2. Regarding the materials for the electron transport layer 15 in the structure of the light emitting device of FIG. 3, the experimental examples Ex4-10 to Ex4-18 of the fourth experimental example group shown in Table 4 use ETMB-09 as the second material C2 and ETM-13 as the first material C1 at a weight ratio of 1:9, 2:8, 3:7, 4:6, 5:5, 6:4, 7:3, 8:2 or 9:1, which gradually increases in the ratio of the second material C2.

In each of the experimental examples, the turn-on voltage at a luminance of 0.1 Cd/m$^2$, the driving voltage at a current density of 10 mA/cm$^2$, the driving voltage at a current density of 100 mA/cm$^2$, and the luminance and the external quantum efficiency at a current density of 10 mA/cm$^2$ were comparatively evaluated.

TABLE 4

| | ETL (C2 + C1) | | | Turn-on voltage [V] | Voltage [V] at | Voltage [V] at | Luminance [Cd/A] at | EQE (%) at 10 |
|---|---|---|---|---|---|---|---|---|
| Item | C2 | C1 | Ratio | at 0.1 Cd/$m^2$ | 10 mA/$cm^2$ | 100 mA/$cm^2$ | 10 mA/$cm^2$ | mA/$cm^2$ |
| Ex4-1 | ETMB-04 | ETM-07 | 1:9 | 3.83 | 5.11 | 6.75 | 4.2 | 6.7 |
| Ex4-2 | ETMB-04 | ETM-07 | 2:8 | 3.58 | 4.85 | 5.84 | 5.0 | 8.0 |
| Ex4-3 | ETMB-04 | ETM-07 | 3:7 | 3.19 | 4.46 | 5.34 | 5.0 | 8.0 |
| Ex4-4 | ETMB-04 | ETM-07 | 4:6 | 2.97 | 4.13 | 4.93 | 5.4 | 8.7 |
| Ex4-5 | ETMB-04 | ETM-07 | 5:5 | 2.89 | 3.83 | 4.68 | 5.7 | 9.2 |
| Ex4-6 | ETMB-04 | ETM-07 | 6:4 | 2.85 | 3.94 | 4.67 | 5.8 | 9.3 |
| Ex4-7 | ETMB-04 | ETM-07 | 7:2 | 2.71 | 3.61 | 5.00 | 5.9 | 7.9 |
| Ex4-8 | ETMB-04 | ETM-07 | 8:2 | 2.72 | 3.96 | 4.80 | 4.9 | 7.8 |
| Ex4-9 | ETMB-04 | ETM-07 | 9:1 | 2.80 | 3.73 | 4.86 | 4.4 | 7.0 |
| Ex4-10 | ETMB-04 | ETM-13 | 1:9 | 3.95 | 4.93 | 6.79 | 4.0 | 6.4 |
| Ex4-11 | ETMB-04 | ETM-13 | 2:8 | 3.65 | 4.63 | 5.90 | 4.2 | 6.7 |
| Ex4-12 | ETMB-04 | ETM-13 | 3:7 | 3.36 | 4.34 | 5.31 | 5.2 | 8.3 |
| Ex4-13 | ETMB-04 | ETM-13 | 4:6 | 2.76 | 3.75 | 4.71 | 5.5 | 8.8 |
| Ex4-14 | ETMB-04 | ETM-13 | 5:5 | 2.78 | 3.78 | 4.76 | 5.7 | 9.1 |
| Ex4-15 | ETMB-04 | ETM-13 | 6:4 | 2.84 | 3.96 | 4.95 | 5.6 | 8.9 |
| Ex4-16 | ETMB-04 | ETM-13 | 7:2 | 2.79 | 3.98 | 4.97 | 4.7 | 7.5 |
| Ex4-17 | ETMB-04 | ETM-13 | 8:2 | 2.89 | 3.71 | 4.96 | 4.1 | 6.6 |
| Ex4-18 | ETMB-04 | ETM-13 | 9:1 | 2.81 | 3.63 | 4.90 | 3.9 | 6.2 |
| Ex4-19 | ETMB-09 | ETM-13 | 1:9 | 4.19 | 5.01 | 6.56 | 3.7 | 5.9 |
| Ex4-20 | ETMB-09 | ETM-13 | 2:8 | 3.51 | 4.72 | 5.36 | 4.9 | 7.8 |
| Ex4-21 | ETMB-09 | ETM-13 | 3:7 | 3.44 | 3.92 | 4.96 | 5.0 | 8.0 |
| Ex4-22 | ETMB-09 | ETM-13 | 4:6 | 3.04 | 3.72 | 4.56 | 5.4 | 8.7 |
| Ex4-23 | ETMB-09 | ETM-13 | 5:5 | 2.90 | 3.75 | 4.70 | 5.8 | 9.3 |
| Ex4-24 | ETMB-09 | ETM-13 | 6:4 | 2.71 | 3.71 | 4.90 | 5.4 | 8.7 |
| Ex4-25 | ETMB-09 | ETM-13 | 7:2 | 2.76 | 3.73 | 4.93 | 5.1 | 8.2 |
| Ex4-26 | ETMB-09 | ETM-13 | 8:2 | 2.89 | 3.73 | 4.72 | 4.1 | 6.6 |
| Ex4-27 | ETMB-09 | ETM-13 | 9:1 | 2.82 | 3.98 | 4.72 | 3.9 | 6.3 |

As can be seen from Table 4, Experimental Examples (Ex4-4, Ex4-5, Ex4-6, Ex4-13, Ex4-14, Ex4-15, Ex4-22, Ex4-23, Ex4-24) of the fourth experimental example group (Ex4-1 to Ex4-27) including the second material C2 and the first material C1 at a weight ratio of 4:6 to 6:4 (wt % ratio) had a decreased turn-on voltage of 2.71V to 3.04V. In addition, it can be seen that the luminance is 5.4 Cd/A to 5.8 Cd/A and the external quantum efficiency is 8.7% to 9.3%.

This can also be seen from the graphs showing the emission spectra of the fourth experimental example group (Ex4-1 to Ex4-27) shown in FIGS. 6A to 6C. In addition, Experimental Examples (Ex4-4, Ex4-5, Ex4-6, Ex4-13, Ex4-14, Ex4-15, Ex4-22, Ex4-23, Ex4-24) of the fourth experimental example group (Ex4-1 to Ex4-27) including the second material C2 and the first material C1 at a weight ratio of 4:6 to 6:4 (wt % ratio) had a decreased turn-on voltage and driving voltage and improved luminance efficiency and external quantum efficiency compared to the first experimental example group or the second experimental example group including the electron transport layer containing a single material.

Meanwhile, the result of experiments on the fourth experimental example group also showed that, when either one of the second material and the first material constituting the electron transport layer is not present as a dopant, but the second material and the first material are used at a ratio equivalent or similar to 1:1, that is, in the range of 4:6 to 6:4, to constitute the layer, both luminance and efficiency are improved.

Hereinafter, the significance of the material for the electron-blocking layer will be investigated based on an example in which the electron transport layer contains benzimidazole represented by Formula 9 in the blue fluorescent stack contacting the cathode and an experimental example in which the material of the electron-blocking layer facing the electron transport layer via the blue light emitting layer interposed therebetween is changed.

Meanwhile, experiments of the fifth and sixth experimental example groups were performed using the following EBM-01 to EBM-12 as the materials of the electron-blocking layer. The electron-blocking layer materials EBM-01 to EBM-12 are all spirofluorene, and there is a difference between the groups EBM-01 to EBM-04 and EBM-05 to EMB-12 depending on whether or not substitution with deuterium was performed.

<EBM-01>

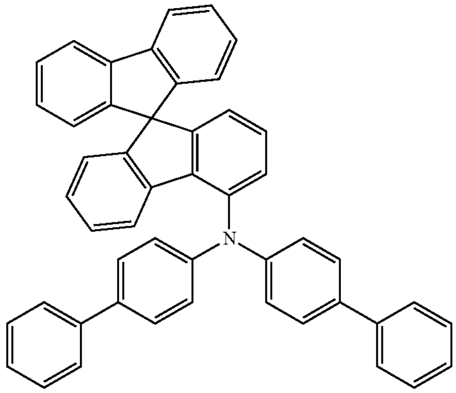

<EBM-02>

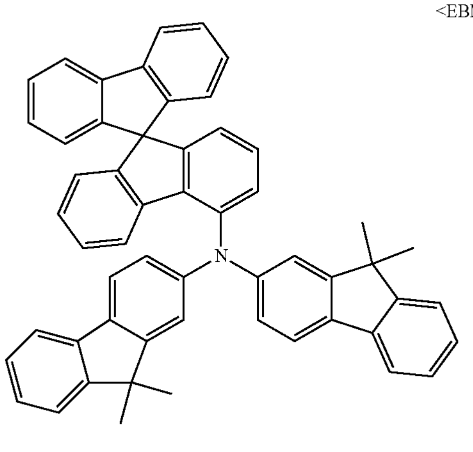

-continued

<EBM-03>

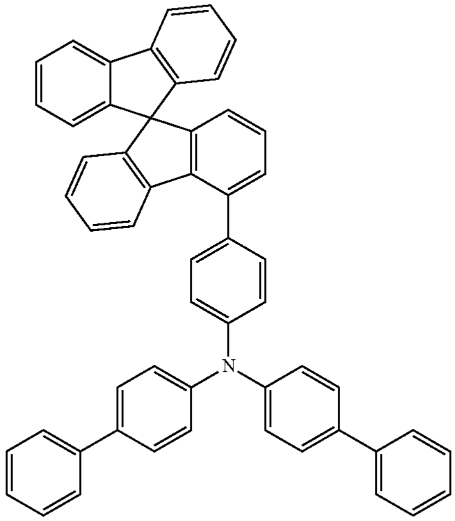

<EBM-04>

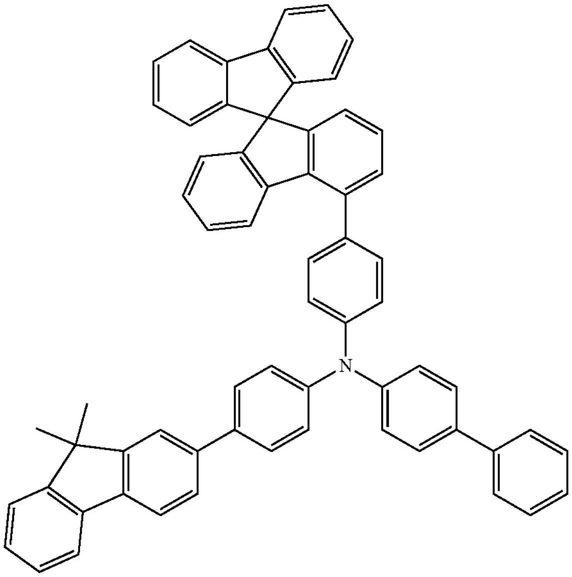

<EBM-05>

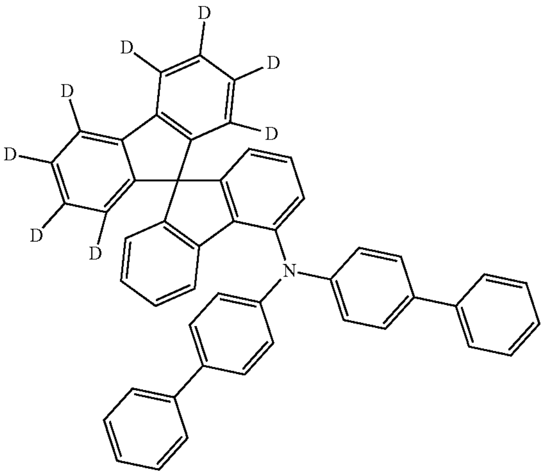

-continued
<EBM-06>
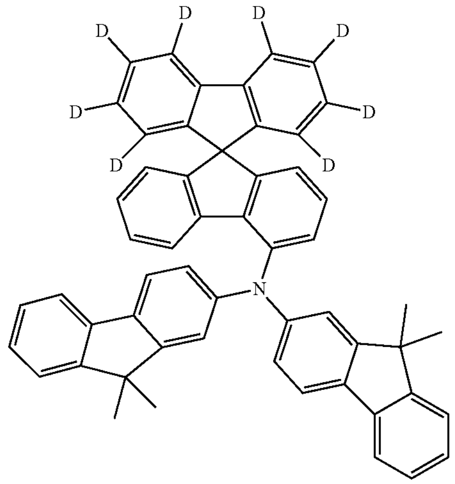
<EBM-07>
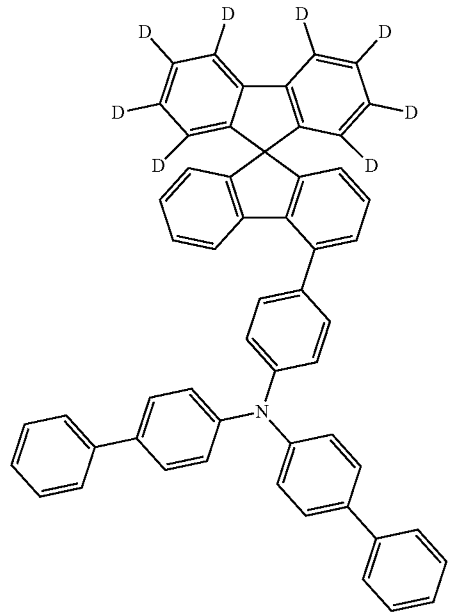
-continued
<EBM-08>
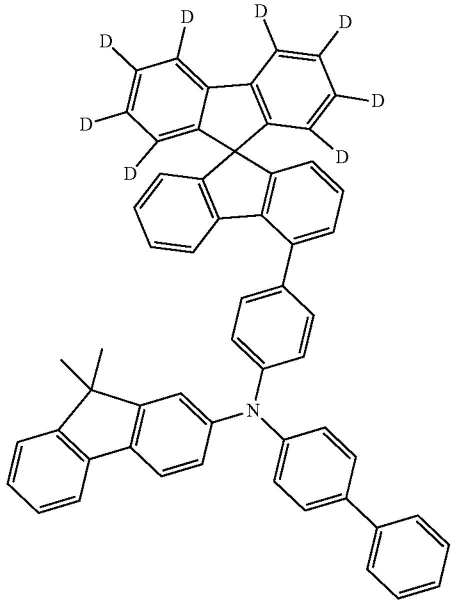
<EBM-09>
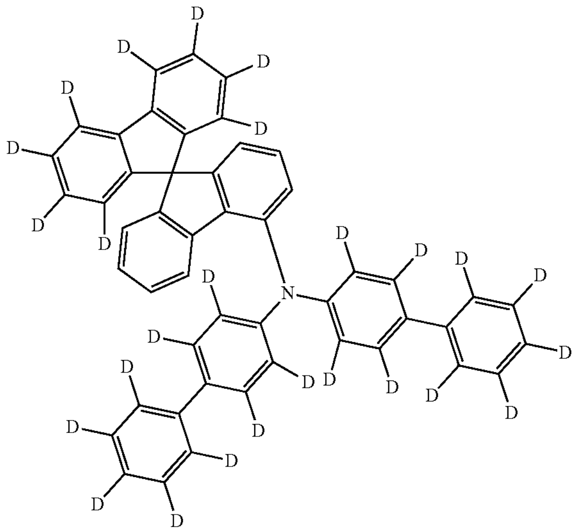

-continued

<EBM-10>

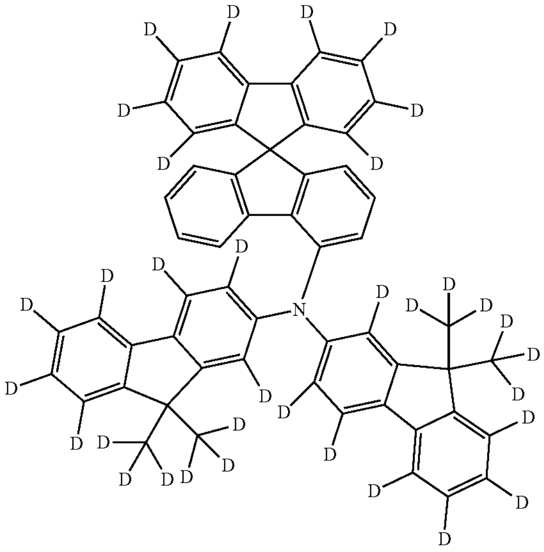

-continued

<EBM-12>

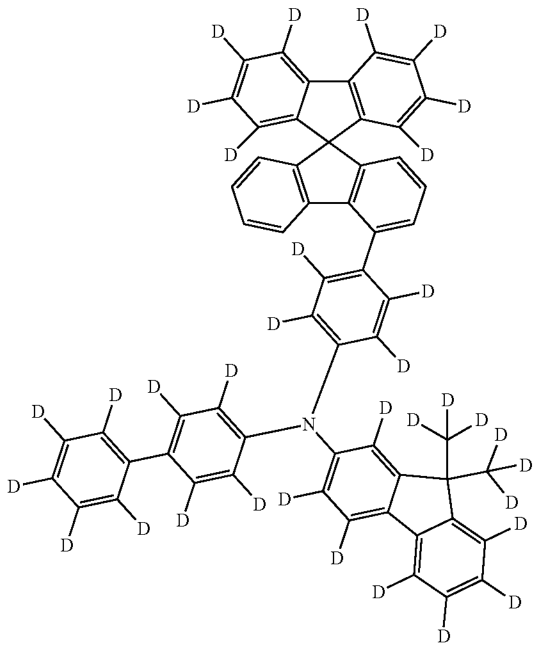

<EBM-11>

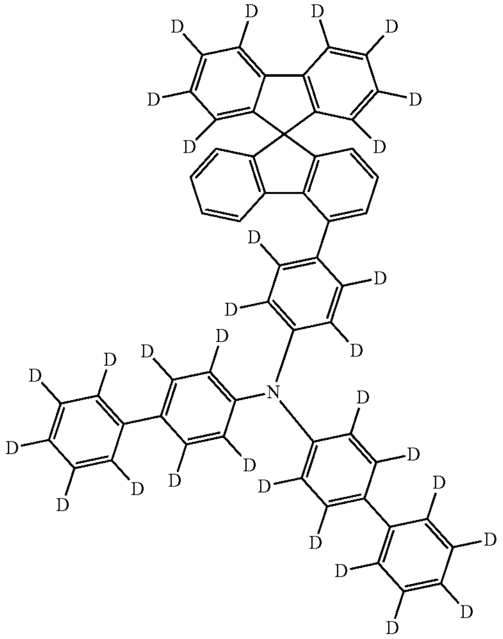

Figure 7:
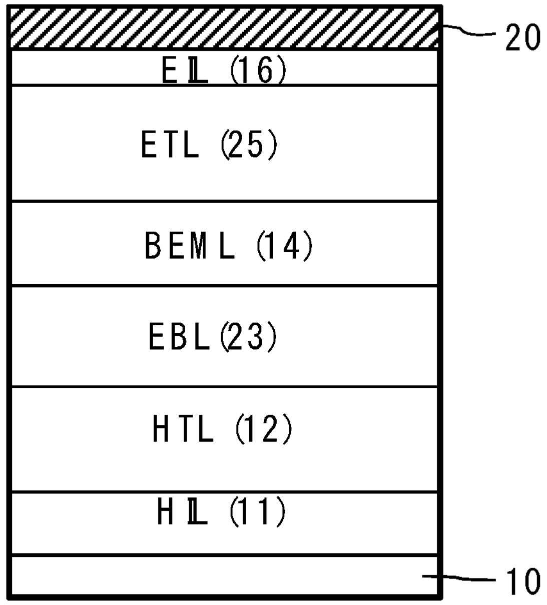
FIG. 7 is a cross-sectional view illustrating light emitting devices used in fifth and sixth experimental example groups according to one embodiment.
Figure 8:
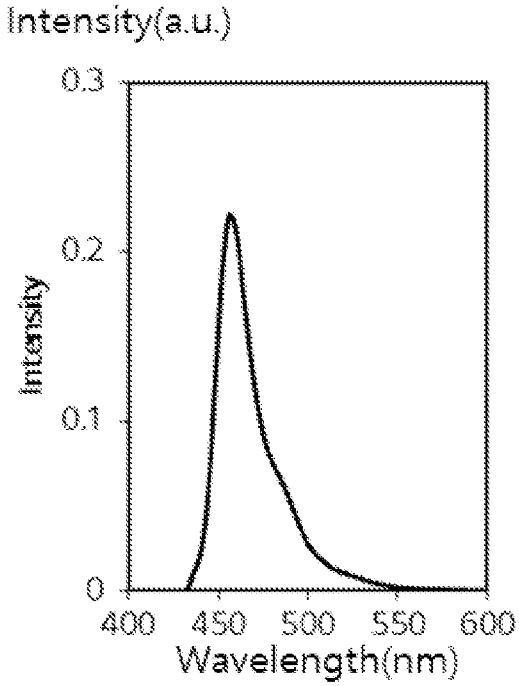
FIG. 8 is a graph showing the emission spectrum of a sixth experimental example group according to one embodiment.

FIG. 7 is a cross-sectional view illustrating the light emitting devices used in the fifth to sixth experimental example groups according to one embodiment, and FIG. 8 is a graph showing the emission spectrum of the sixth experimental example group according to one embodiment.

The light emitting devices used in the fifth experimental example group (Ex5-1 to Ex5-42) include the following configuration sequentially on the anode 10 made of ITO, as shown in FIG. 7.

That is, a mixture of DNTPD of Formula 5 and $MgF_2$ at a ratio of 1:1 is deposited to a thickness of 7.5 nm on the anode 10 to form a hole injection layer HIL 11.

Then, α-NPD is deposited to a thickness of 80 nm on the hole injection layer (HIL) 11 to form a hole transport layer (HTL) 12.

Then, an electron-blocking layer (EBL) 23 is formed to a thickness of 20 nm on the hole transport layer 12. As shown in Tables 5 and 6, in the fifth and sixth experimental example groups, EBM-01 to EBM-12, mentioned above, are used as the electron-blocking material. Then, MADN of Formula 7 and a boron-based dopant of doped with DABNA-1 of Formula 8 at 3 wt % are formed on the electron-blocking layer 13 to form a blue light emitting layer BEML 14 having a thickness of 30 nm.

Then, in respective experimental examples (Ex5-1 to Ex5-42) of the fifth experimental example group, the electron transport layer (ETL) 25 is formed to a thickness of 25 nm using the ZADN of Formula 9 as a single material or the first material of Formula 1 as a single material.

Then, an electron injection layer (EIL) 16 having a thickness of 2 nm is formed using LiF on the electron transport layer 25. Then, a cathode 20 made of an aluminum (Al) component is formed on the electron injection layer 16.

Meanwhile, as shown in Table 5, Experimental Examples Ex5-1 to Ex5-12 of the fifth experimental example group (Ex5-1 to Ex5-42) are obtained using ZADN of Formula 9 as a material for the electron transport layer and changing to one of EBM-01 to EBM-12 as a material for the electron-blocking layer.

[Formula 9]

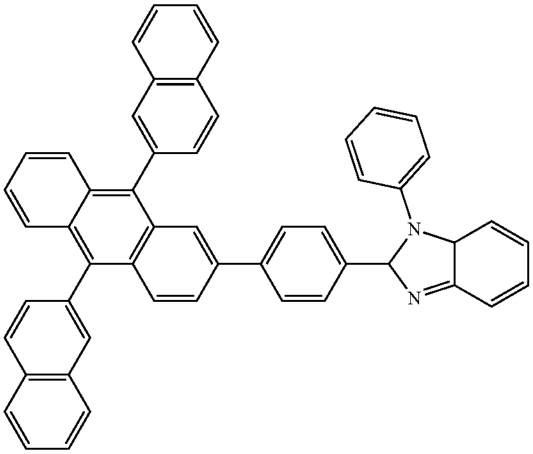

In addition, Experimental Examples Ex5-13 to Ex5-27 are obtained by using EBM-01 as the electron-blocking layer material and changing the electron transport layer material to ETM-07, ETM-09, ETM-12, ETM-14, ETM-18, ETM-22, ETM-28, ETM-32, ETM-37, ETM-41, ETM-44, ETM-48, ETM-51, ETM-54, or ETM-58. Experimental Examples Ex5-28 to Ex5-42 are obtained by using EBM-03 as the electron-blocking layer material and changing the electron transport layer material to ETM-07, ETM-09, ETM-12, ETM-14, ETM-18, ETM-22, ETM-28, ETM-32, ETM-37, ETM-41, ETM-44, ETM-48, ETM-51, ETM-54, or ETM-58.

In each experimental example, the turn-on voltage at a luminance of 0.1 Cd/$m^2$, the driving voltage at a current density of 10 mA/$cm^2$, the driving voltage at a current density of 100 mA/$cm^2$, and the luminance and the external quantum efficiency at current densities of 55 mA/$cm^2$ as well as 10 mA/$cm^2$ were comparatively evaluated. The remaining experimental examples were comparatively evaluated based on the lifespan of Ex5-2 in the fifth experimental example group.

TABLE 5

| Item | Structure EBM (C3) | Structure ETL | Voltage [V] at 0.1 Cd/$m^2$ | Voltage [V] at 10 mA/$cm^2$ | Voltage [V] at 100 mA/$cm^2$ | Luminance [Cd/A] at 10 mA/$cm^2$ | EQE (%) at 10 mA/$cm^2$ | Lifespan (%) at 55 mA/$cm^2$ |
|---|---|---|---|---|---|---|---|---|
| Ex5-1 | EBM-01 | ZADN | 2.89 | 3.62 | 4.70 | 5.1 | 8.2 | 98 |
| Ex5-2 | EBM-02 | ZADN | 2.89 | 3.79 | 4.62 | 4.6 | 7.3 | 100 |
| Ex5-3 | EBM-03 | ZADN | 2.75 | 3.76 | 4.50 | 4.7 | 7.5 | 99 |
| Ex5-4 | EBM-04 | ZADN | 2.77 | 3.70 | 4.53 | 4.9 | 7.9 | 94 |
| Ex5-5 | EBM-05 | ZADN | 2.86 | 3.62 | 4.69 | 5.0 | 8.0 | 105 |
| Ex5-6 | EBM-06 | ZADN | 2.80 | 3.62 | 4.65 | 4.5 | 7.3 | 107 |
| Ex5-7 | EBM-07 | ZADN | 2.79 | 3.66 | 4.68 | 4.8 | 7.7 | 106 |
| Ex5-8 | EBM-08 | ZADN | 2.80 | 3.75 | 4.67 | 4.4 | 7.1 | 101 |
| Ex5-9 | EBM-09 | ZADN | 2.75 | 3.65 | 4.70 | 4.6 | 7.3 | 113 |
| Ex5-10 | EBM-10 | ZADN | 2.77 | 3.77 | 4.62 | 5.0 | 8.1 | 114 |
| Ex5-11 | EBM-11 | ZADN | 2.86 | 3.76 | 4.50 | 4.7 | 7.5 | 113 |
| Ex5-12 | EBM-12 | ZADN | 2.80 | 3.76 | 4.53 | 5.0 | 8.0 | 108 |
| Ex5-13 | EBM-01 | ETM-07 | 3.69 | 4.65 | 7.08 | 4.5 | 7.2 | 69 |
| Ex5-14 | EBM-01 | ETM-09 | 3.67 | 4.60 | 7.14 | 5.1 | 8.2 | 65 |
| Ex5-15 | EBM-01 | ETM-12 | 3.67 | 4.51 | 7.01 | 5.2 | 8.3 | 82 |
| Ex5-16 | EBM-01 | ETM-14 | 3.69 | 4.54 | 7.08 | 5.1 | 8.2 | 66 |
| Ex5-17 | EBM-01 | ETM-18 | 3.68 | 4.62 | 7.12 | 5.0 | 8.0 | 74 |
| Ex5-18 | EBM-01 | ETM-22 | 3.59 | 4.60 | 7.17 | 4.7 | 7.5 | 81 |
| Ex5-19 | EBM-01 | ETM-28 | 3.62 | 4.56 | 7.14 | 4.5 | 7.3 | 79 |
| Ex5-20 | EBM-01 | ETM-32 | 3.64 | 4.55 | 7.13 | 4.5 | 7.2 | 64 |
| Ex5-21 | EBM-01 | ETM-37 | 3.64 | 4.65 | 7.19 | 5.1 | 8.3 | 86 |
| Ex5-22 | EBM-01 | ETM-41 | 3.63 | 4.60 | 7.18 | 4.8 | 7.7 | 76 |
| Ex5-23 | EBM-01 | ETM-44 | 3.52 | 4.68 | 7.17 | 4.8 | 7.9 | 71 |

TABLE 5-continued

| Item | Structure EBM (C3) | ETL | Voltage [V] at 0.1 Cd/$m^2$ | Voltage [V] at 10 mA/$cm^2$ | Voltage [V] at 100 mA/$cm^2$ | Luminance [Cd/A] at 10 mA/$cm^2$ | EQE (%) at 10 mA/$cm^2$ | Lifespan (%) at 55 mA/$cm^2$ |
|---|---|---|---|---|---|---|---|---|
| Ex5-24 | EBM-01 | ETM-48 | 3.52 | 4.66 | 7.07 | 4.6 | 7.4 | 76 |
| Ex5-25 | EBM-01 | ETM-51 | 3.63 | 4.62 | 7.19 | 4.4 | 7.1 | 85 |
| Ex5-26 | EBM-01 | ETM-54 | 3.68 | 4.52 | 7.16 | 4.7 | 7.6 | 75 |
| Ex5-27 | EBM-01 | ETM-58 | 3.59 | 4.58 | 7.04 | 4.43 | 7.1 | 69 |
| Ex5-28 | EBM-03 | ETM-07 | 3.53 | 4.65 | 7.11 | 4.3 | 7.0 | 85 |
| Ex5-29 | EBM-03 | ETM-09 | 3.56 | 4.59 | 7.16 | 4.6 | 7.4 | 73 |
| Ex5-30 | EBM-03 | ETM-12 | 3.58 | 4.56 | 7.17 | 4.7 | 7.6 | 81 |
| Ex5-31 | EBM-03 | ETM-14 | 3.58 | 4.65 | 7.16 | 5.1 | 8.3 | 71 |
| Ex5-32 | EBM-03 | ETM-18 | 3.70 | 4.70 | 7.18 | 4.7 | 7.6 | 84 |
| Ex5-33 | EBM-03 | ETM-22 | 3.53 | 4.66 | 7.05 | 5.2 | 8.3 | 72 |
| Ex5-34 | EBM-03 | ETM-28 | 3.52 | 4.63 | 7.17 | 4.7 | 7.5 | 86 |
| Ex5-35 | EBM-03 | ETM-32 | 3.50 | 4.67 | 7.07 | 5.2 | 8.3 | 66 |
| Ex5-36 | EBM-03 | ETM-37 | 3.55 | 4.68 | 7.03 | 4.8 | 7.8 | 84 |
| Ex5-37 | EBM-03 | ETM-41 | 3.51 | 4.56 | 7.16 | 4.6 | 7.4 | 79 |
| Ex5-38 | EBM-03 | ETM-44 | 3.57 | 4.60 | 7.19 | 5.0 | 8.1 | 77 |
| Ex5-39 | EBM-03 | ETM-48 | 3.62 | 4.51 | 7.13 | 5.1 | 8.1 | 80 |
| Ex5-40 | EBM-03 | ETM-51 | 3.60 | 4.62 | 7.06 | 4.4 | 7.1 | 71 |
| Ex5-41 | EBM-03 | ETM-54 | 3.6 | 4.68 | 7.10 | 4.5 | 7.2 | 86 |
| Ex5-42 | EBM-03 | ETM-58 | 3.56 | 4.59 | 7.15 | 4.7 | 7.6 | 85 |

In Experimental Examples Ex5-1 to Ex5-12 of the fifth experimental example group (Ex5-1 to Ext1-42), when the electron transport layer material was the same as ZADN and only the electron-blocking layer material was different, the lifespan was prolonged depending on the deuterium substitution rate. At this time, the turn-on voltage at a luminance of 0.1 Cd/$m^2$ was about 2.8V on average. In comparison, in Experimental Examples Ex5-13 to Ex5-42, when the electron-blocking layer was spirofluorene that is not substituted with deuterium, the external quantum efficiency was improved by 8% or more because the electron transport layer material was changed to the material having high external quantum efficiency of Formula 1, but the turn-on voltage increased to the level of 3.6V on average. In addition, the lifespan also decreased in Experimental Examples Ex5-13 to Ex5-42.

In the sixth experimental example group (Ex6-1 to Ex6-60), as shown in Table 6, the material of the electron-blocking layer was changed to one of EBM-01 to EBM-12, and the material of the electron transport layer was a mixture of two materials, wherein one was ZADN and the other was changed to ETM-07, ETM-14, ETM-28, ETM-37, or ETM-54. In each experimental example, the turn-on voltage at a luminance of 0.1 Cd/$m^2$, the driving voltage at a current density of 10 mA/$cm^2$, the driving voltage at a current density of 100 mA/$cm^2$, and the luminance and the external quantum efficiency at a current density of 55 mA/$cm^2$ were comparatively evaluated. The remaining experimental examples were comparatively evaluated based on the lifespan of Ex5-2 in the fifth experimental example group. The materials of the electron transport layer co-deposited herein were mixed at the weight ratio of 1:1 (5:5).

TABLE 6

| Item | Structure EBM (C3) | Structure ETL (ZADN + C1) ZADN | Structure ETL (ZADN + C1) C1 | Voltage [V] at 0.1 Cd/$m^2$ | Voltage [V] at 10 mA/$cm^2$ | Voltage [V] at 100 mA/$cm^2$ | Luminance [Cd/A] at 10 mA/$cm^2$ | EQE (%) at 10 mA/$cm^2$ | Lifespan (%) at 55 mA/$cm^2$ |
|---|---|---|---|---|---|---|---|---|---|
| Ex6-1 | EBM-01 | ZADN | ETM-07 | 2.74 | 3.76 | 4.68 | 5.1 | 9.0 | 75 |
| Ex6-2 | EBM-01 | ZADN | ETM-14 | 2.82 | 3.66 | 4.59 | 5.3 | 8.5 | 77 |

TABLE 6-continued

| Item | Structure EBM (C3) | ETL (ZADN + C1) ZADN | ETL (ZADN + C1) C1 | Voltage [V] at 0.1 Cd/m$^2$ | Voltage [V] at 10 mA/cm$^2$ | Voltage [V] at 100 mA/cm$^2$ | Luminance [Cd/A] at 10 mA/cm$^2$ | EQE (%) at 10 mA/cm$^2$ | Lifespan (%) at 55 mA/cm$^2$ |
|---|---|---|---|---|---|---|---|---|---|
| Ex6-3 | EBM-01 | ZADN | ETM-28 | 2.77 | 3.69 | 4.65 | 5.6 | 9.0 | 83 |
| Ex6-4 | EBM-01 | ZADN | ETM-37 | 2.75 | 3.70 | 4.52 | 5.5 | 8.8 | 76 |
| Ex6-5 | EBM-01 | ZADN | ETM-54 | 2.72 | 3.79 | 4.61 | 5.4 | 8.6 | 83 |
| Ex6-6 | EBM-02 | ZADN | ETM-07 | 2.74 | 3.76 | 4.68 | 5.1 | 9.0 | 75 |
| Ex6-7 | EBM-02 | ZADN | ETM-14 | 2.82 | 3.66 | 4.59 | 5.3 | 8.5 | 77 |
| Ex6-8 | EBM-02 | ZADN | ETM-28 | 2.77 | 3.69 | 4.65 | 5.6 | 9.0 | 83 |
| Ex6-9 | EBM-02 | ZADN | ETM-37 | 2.75 | 3.70 | 4.52 | 5.5 | 8.8 | 76 |
| Ex6-10 | EBM-02 | ZADN | ETM-54 | 2.72 | 3.79 | 4.61 | 5.4 | 8.6 | 83 |
| Ex6-11 | EBM-03 | ZADN | ETM-07 | 2.74 | 3.76 | 4.68 | 5.1 | 9.0 | 75 |
| Ex6-12 | EBM-03 | ZADN | ETM-14 | 2.82 | 3.66 | 4.59 | 5.3 | 8.5 | 77 |
| Ex6-13 | EBM-03 | ZADN | ETM-28 | 2.77 | 3.69 | 4.65 | 5.6 | 9.0 | 83 |
| Ex6-14 | EBM-03 | ZADN | ETM-37 | 2.75 | 3.70 | 4.52 | 5.5 | 8.8 | 76 |
| Ex6-15 | EBM-03 | ZADN | ETM-54 | 2.72 | 3.79 | 4.61 | 5.4 | 8.6 | 83 |
| Ex6-16 | EBM-04 | ZADN | ETM-07 | 2.74 | 3.76 | 4.68 | 5.1 | 9.0 | 75 |
| Ex6-17 | EBM-04 | ZADN | ETM-14 | 2.82 | 3.66 | 4.59 | 5.3 | 8.5 | 77 |
| Ex6-18 | EBM-04 | ZADN | ETM-28 | 2.77 | 3.69 | 4.65 | 5.6 | 9.0 | 83 |
| Ex6-19 | EBM-04 | ZADN | ETM-37 | 2.75 | 3.70 | 4.52 | 5.5 | 8.8 | 76 |
| Ex6-20 | EBM-04 | ZADN | ETM-54 | 2.72 | 3.79 | 4.61 | 5.4 | 8.6 | 83 |
| Ex6-21 | EBM-05 | ZADN | ETM-07 | 2.74 | 3.76 | 4.68 | 5.1 | 9.0 | 75 |
| Ex6-22 | EBM-05 | ZADN | ETM-14 | 2.82 | 3.66 | 4.59 | 5.3 | 8.5 | 77 |
| Ex6-23 | EBM-05 | ZADN | ETM-28 | 2.77 | 3.69 | 4.65 | 5.6 | 9.0 | 83 |
| Ex6-24 | EBM-05 | ZADN | ETM-37 | 2.75 | 3.70 | 4.52 | 5.5 | 8.8 | 76 |
| Ex6-25 | EBM-05 | ZADN | ETM-54 | 2.72 | 3.79 | 4.61 | 5.4 | 8.6 | 83 |
| Ex6-26 | EBM-06 | ZADN | ETM-07 | 2.74 | 3.76 | 4.68 | 5.1 | 9.0 | 75 |
| Ex6-27 | EBM-06 | ZADN | ETM-14 | 2.82 | 3.66 | 4.59 | 5.3 | 8.5 | 77 |
| Ex6-28 | EBM-06 | ZADN | ETM-28 | 2.77 | 3.69 | 4.65 | 5.6 | 9.0 | 83 |
| Ex6-29 | EBM-06 | ZADN | ETM-37 | 2.75 | 3.70 | 4.52 | 5.5 | 8.8 | 76 |
| Ex6-30 | EBM-06 | ZADN | ETM-54 | 2.72 | 3.79 | 4.61 | 5.4 | 8.6 | 83 |
| Ex6-31 | EBM-07 | ZADN | ETM-07 | 2.74 | 3.76 | 4.68 | 5.1 | 9.0 | 75 |
| Ex6-32 | EBM-07 | ZADN | ETM-14 | 2.82 | 3.66 | 4.59 | 5.3 | 8.5 | 77 |
| Ex6-33 | EBM-07 | ZADN | ETM-28 | 2.77 | 3.69 | 4.65 | 5.6 | 9.0 | 83 |
| Ex6-34 | EBM-07 | ZADN | ETM-37 | 2.75 | 3.70 | 4.52 | 5.5 | 8.8 | 76 |
| Ex6-35 | EBM-07 | ZADN | ETM-54 | 2.72 | 3.79 | 4.61 | 5.4 | 8.6 | 83 |
| Ex6-36 | EBM-08 | ZADN | ETM-07 | 2.74 | 3.76 | 4.68 | 5.1 | 9.0 | 75 |
| Ex6-37 | EBM-08 | ZADN | ETM-14 | 2.82 | 3.66 | 4.59 | 5.3 | 8.5 | 77 |
| Ex6-38 | EBM-08 | ZADN | ETM-28 | 2.77 | 3.69 | 4.65 | 5.6 | 9.0 | 83 |

TABLE 6-continued

| Item | Structure EBM (C3) | ETL (ZADN + C1) ZADN | C1 | Voltage [V] at 0.1 Cd/m$^2$ | Voltage [V] at 10 mA/cm$^2$ | Voltage [V] at 100 mA/cm$^2$ | Luminance [Cd/A] at 10 mA/cm$^2$ | EQE (%) at 10 mA/cm$^2$ | Lifespan (%) at 55 mA/cm$^2$ |
|---|---|---|---|---|---|---|---|---|---|
| Ex6-39 | EBM-08 | ZADN | ETM-37 | 2.75 | 3.70 | 4.52 | 5.5 | 8.8 | 76 |
| Ex6-40 | EBM-08 | ZADN | ETM-54 | 2.72 | 3.79 | 4.61 | 5.4 | 8.6 | 83 |
| Ex6-41 | EBM-09 | ZADN | ETM-07 | 2.74 | 3.76 | 4.68 | 5.1 | 9.0 | 75 |
| Ex6-42 | EBM-09 | ZADN | ETM-14 | 2.82 | 3.66 | 4.59 | 5.3 | 8.5 | 77 |
| Ex6-43 | EBM-09 | ZADN | ETM-28 | 2.77 | 3.69 | 4.65 | 5.6 | 9.0 | 83 |
| Ex6-44 | EBM-09 | ZADN | ETM-37 | 2.75 | 3.70 | 4.52 | 5.5 | 8.8 | 76 |
| Ex6-45 | EBM-09 | ZADN | ETM-54 | 2.72 | 3.79 | 4.61 | 5.4 | 8.6 | 83 |
| Ex6-46 | EBM-10 | ZADN | ETM-07 | 2.74 | 3.76 | 4.68 | 5.1 | 9.0 | 75 |
| Ex6-47 | EBM-10 | ZADN | ETM-14 | 2.82 | 3.66 | 4.59 | 5.3 | 8.5 | 77 |
| Ex6-48 | EBM-10 | ZADN | ETM-28 | 2.77 | 3.69 | 4.65 | 5.6 | 9.0 | 83 |
| Ex6-49 | EBM-10 | ZADN | ETM-37 | 2.75 | 3.70 | 4.52 | 5.5 | 8.8 | 76 |
| Ex6-50 | EBM-10 | ZADN | ETM-54 | 2.72 | 3.79 | 4.61 | 5.4 | 8.6 | 83 |
| Ex6-51 | EBM-11 | ZADN | ETM-07 | 2.74 | 3.76 | 4.68 | 5.1 | 9.0 | 75 |
| Ex6-52 | EBM-11 | ZADN | ETM-14 | 2.82 | 3.66 | 4.59 | 5.3 | 8.5 | 77 |
| Ex6-53 | EBM-11 | ZADN | ETM-28 | 2.77 | 3.69 | 4.65 | 5.6 | 9.0 | 83 |
| Ex6-54 | EBM-11 | ZADN | ETM-37 | 2.75 | 3.70 | 4.52 | 5.5 | 8.8 | 76 |
| Ex6-55 | EBM-11 | ZADN | ETM-54 | 2.72 | 3.79 | 4.61 | 5.4 | 8.6 | 83 |
| Ex6-56 | EBM-12 | ZADN | ETM-07 | 2.74 | 3.76 | 4.68 | 5.1 | 9.0 | 75 |
| Ex6-57 | EBM-12 | ZADN | ETM-14 | 2.82 | 3.66 | 4.59 | 5.3 | 8.5 | 77 |
| Ex6-58 | EBM-12 | ZADN | ETM-28 | 2.77 | 3.69 | 4.65 | 5.6 | 9.0 | 83 |
| Ex6-59 | EBM-12 | ZADN | ETM-37 | 2.75 | 3.70 | 4.52 | 5.5 | 8.8 | 76 |
| Ex6-60 | EBM-12 | ZADN | ETM-54 | 2.72 | 3.79 | 4.61 | 5.4 | 8.6 | 83 |

As can be seen from the results of the sixth experimental example group (Ex6-1 to Ex6-60), the turn-on voltage at a luminance of 0.1 Cd/m$^2$ was increased to about 2.8V on average compared to the fifth experimental example group (Ex5-1 to Ex5-42), and the external quantum efficiency was high, around 8.5 to 9.0%. In addition, as the deuterium substitution rate of the electron-blocking layer increases, the lifespan is prolonged. As a result, it can be seen that the sixth experimental example group (Ex6-1 to Ex6-60) had a similar lifespan at a higher external quantum efficiency than Ex5-2 of the fifth Experimental Example group. It can be seen that FIG. 8 shows a spectrum similar to that described in FIG. 5C showing the emission spectra of the third experimental example group. FIG. 8 shows the spectrum regarding Ex6-56 of the sixth experimental example group.

It can also be seen that the fifth experimental example group and the sixth experimental example group exhibit excellent electron injection efficiency and thus improved external quantum efficiency when a mixture of the first material C1 of Formula 1 having good electron transport efficiency with ZADN including benzimidazole having excellent compatibility with the electron injection layer is used for the electron transport layer of the blue fluorescent unit close to the cathode. It can be seen that the lifespan characteristics are improved when the third material C3 constituting the electron-blocking layer has more deuterium substitution sites. Here, ZADN mixed in the electron transport layer includes benzimidazole, similar to the second material C2 of Formula 2 above, has good compatibility with the electron injection layer, and has a similar effect of lowering interfacial resistance during electron injection. The same effect is obtained even if ZADN is replaced with the second material C2.

Figure 9:
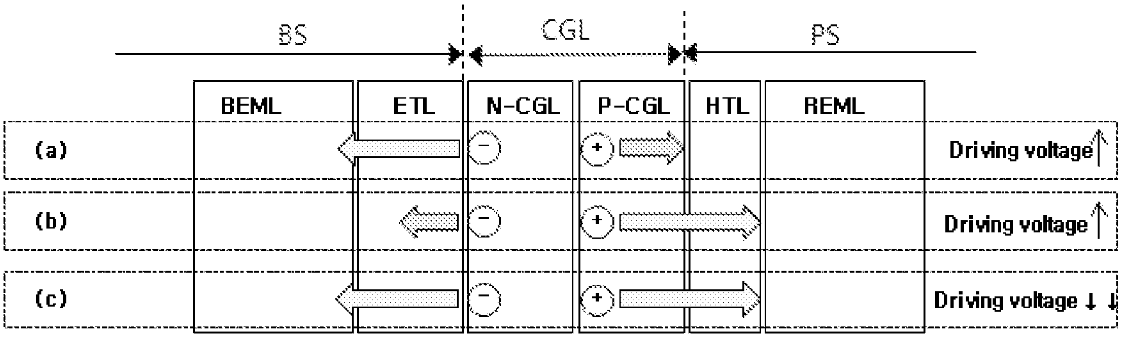
FIG. 9 is a schematic diagram illustrating a change in driving voltage due to the transport capability of the electron transport layer of the blue fluorescent stack and the hole generation capability of a p-type charge generation layer between the blue fluorescent stack and the phosphorescent stack according to one embodiment.

FIG. 9 is a schematic diagram illustrating a change in driving voltage due to the transport capability of the electron transport layer of the blue fluorescent stack and the hole generation capability of a p-type charge generation layer between the blue fluorescent stack and the phosphorescent stack.

As shown in FIG. 9, when the blue fluorescent stack BS and the phosphorescent stack PS are adjacent to each other, an n-type charge generation layer N-CGL and a p-type charge generation layer P-CGL are provided between the two stacks, which respectively supply the generated electrons to the blue fluorescent stack BS and supply the generated holes to the phosphorescent stack PS.

Part (a), part (b) and part (c) of FIG. 9 all show that the n-type charge generation layer N-CGL has the same electron generation capability.

Part (a) of FIG. 9 shows an example in which the electron transport layer ETL has excellent electron transport ability and the p-type charge generation layer P-CGL has low hole generation ability, wherein electrons generated in the n-type charge generation layer N-CGL can be rapidly transferred to the blue light emitting layer BEML and then annihilated, but holes generated in the p-type charge generation layer P-CGL require a large driving voltage to transfer to the red phosphorescent light emitting layer REML. In addition, a difference in electron and hole transport capability occurs between adjacent stacks, so electrons supplied first to each light emitting layer block holes to suppress the excitation action, or a reverse action occurs, resulting in a decrease in the recombination rate of electrons and holes in the light emitting layer.

Part (b) of FIG. 9 is an example in which the electron transport capability of the electron transport layer (ETL) is low and the hole generation ability of the p-type charge generation layer P-CGL is excellent, in contrast to (a) of FIG. 9, wherein holes generated in the p-type charge generation layer P-CGL can be rapidly supplied to the red phosphorescent light emitting layer REML through the hole transport layer HTL of the phosphorescent stack PS, but a large driving voltage is required in order to transfer electrons from the n-type charge generation layer N-CGL through the electron transport layer ETL to the blue light emitting layer BEML.

Part (c) of FIG. 9 shows an example in which the p-type charge generation layer P-CGL has excellent hole generation ability and thus the electron transport layer ETL of the blue fluorescent stack BS has excellent electron transport capability. In this case, the driving voltage is expected to be reduced.

As described above, when the electron transport layer (ETL) contains the first material of Formula 1, excellent electron transport ability can be obtained. The blue fluorescent stack BS contacting the phosphorescent stack PS contains at least the first material of Formula 1 as the material for the electron transport layer ETL, and contains the fourth material C4 of Formula 4 as the p-type dopant material of the p-type charge generation layer P-CGL as the fourth material C4 of Formula 4, to implement the example of part (c) of FIG. 9.

In a seventh Experimental Example group[, PD-01 to PD-03, having physical properties different from the fourth material C4 of Formula 4, were presented, and PD-04 to PD-36 may be used as examples of the fourth material C4 of Formula 4.

PD-01

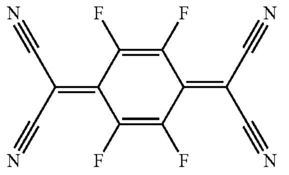

-continued

PD-02

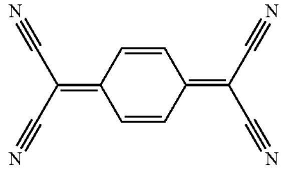

PD-03

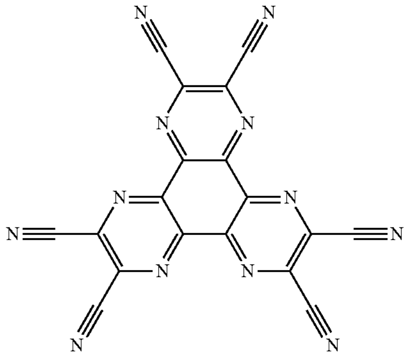

PD-04

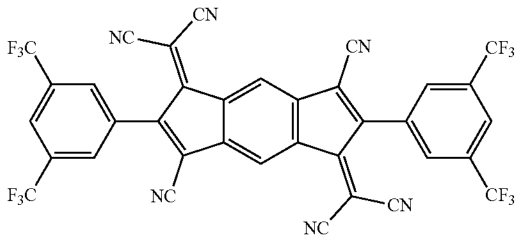

PD-05

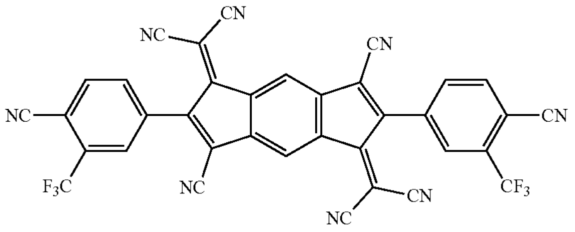

PD-06

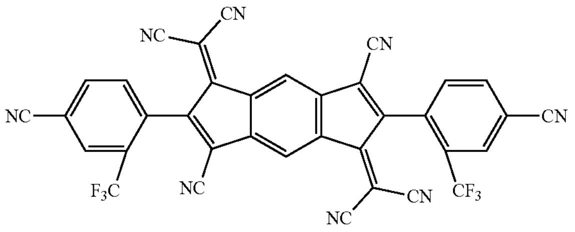

PD-07

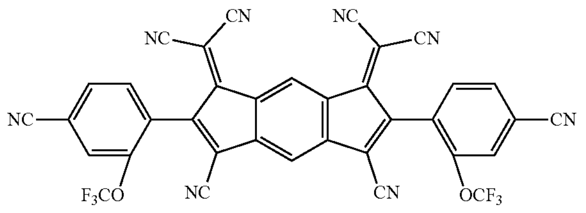

-continued
PD-08
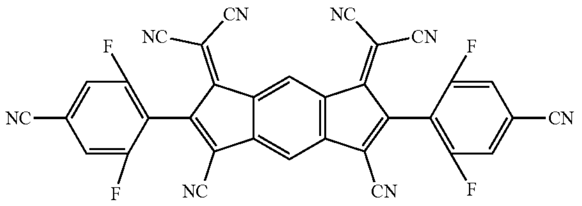
PD-09
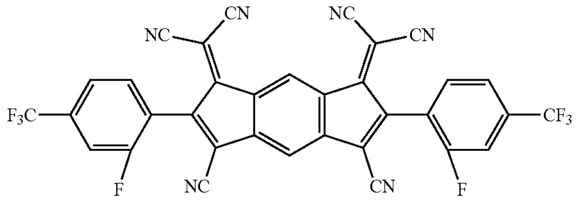
PD-10
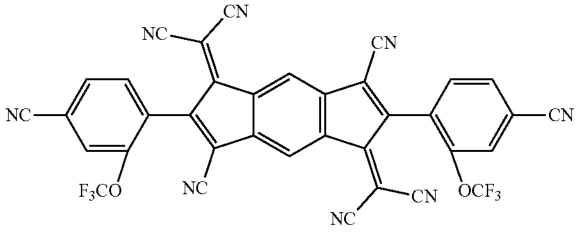
PD-11
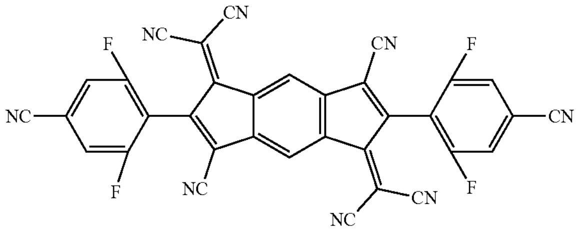
PD-12
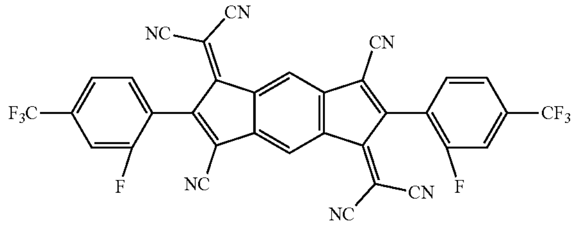
PD-13
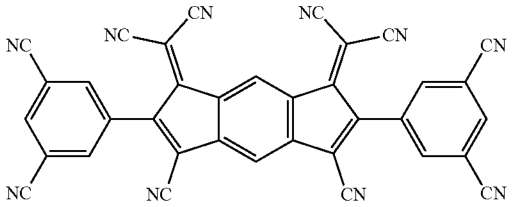
-continued
PD-14
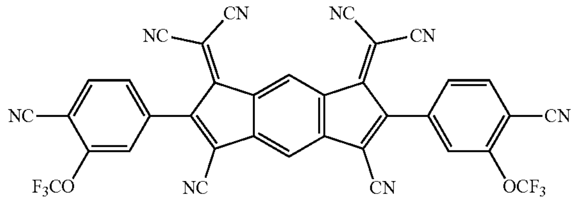
PD-15
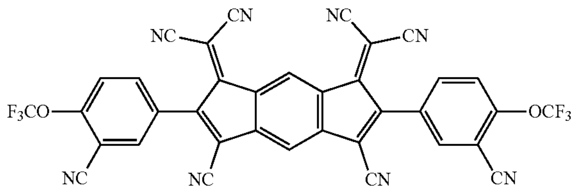
PD-16
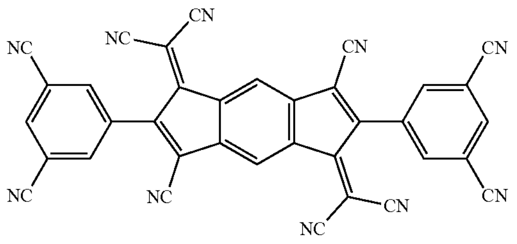
PD-17
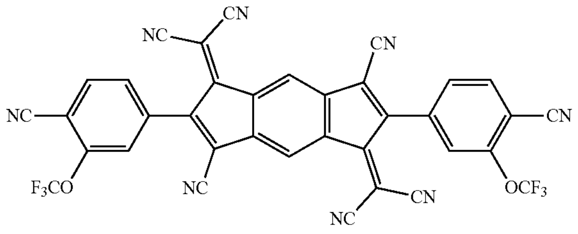
PD-18
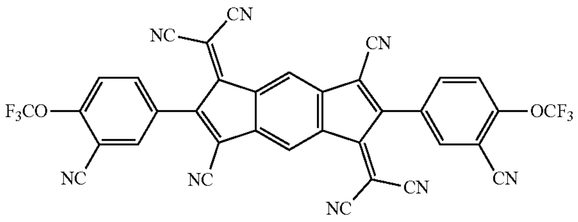
PD-19
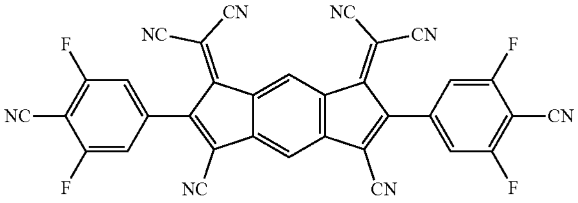

-continued
PD-20
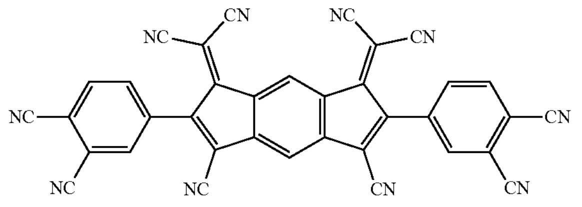
PD-21
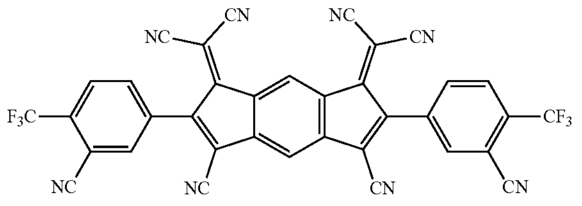
PD-22
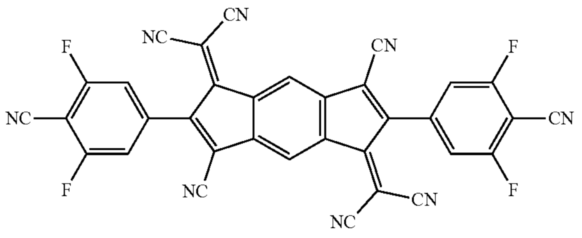
PD-23
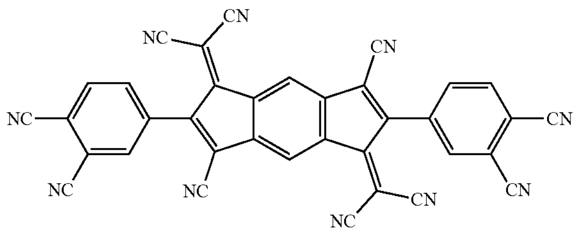
PD-24
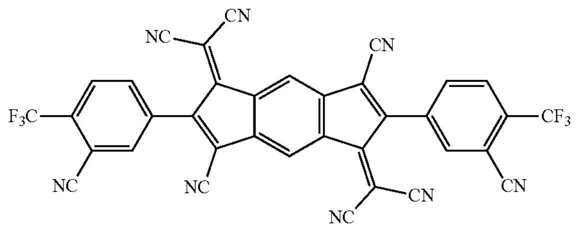
PD-25
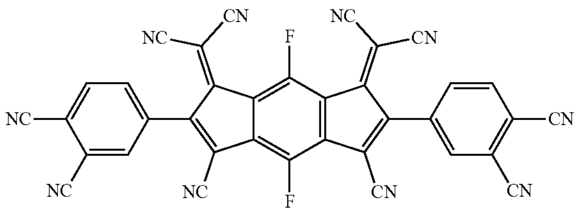
-continued
PD-26
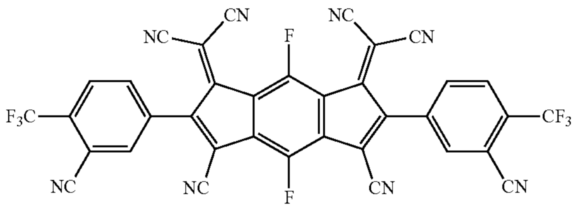
PD-27
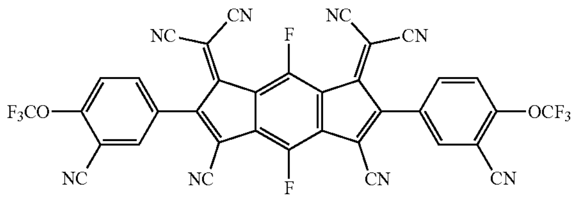
PD-28
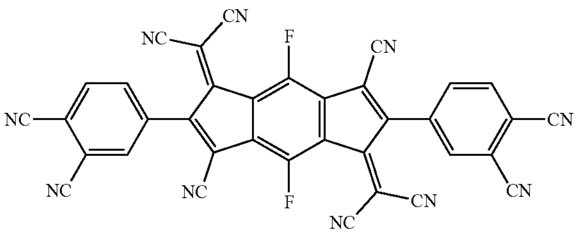
PD-29
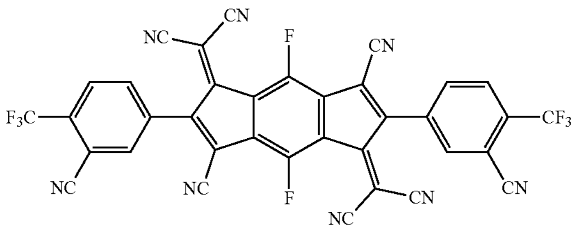
PD-30
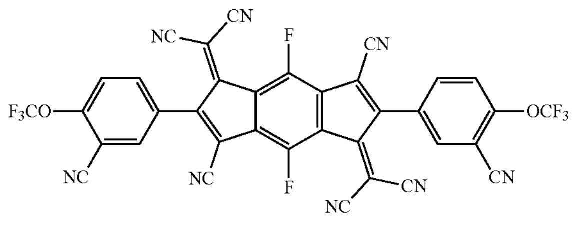
PD-31
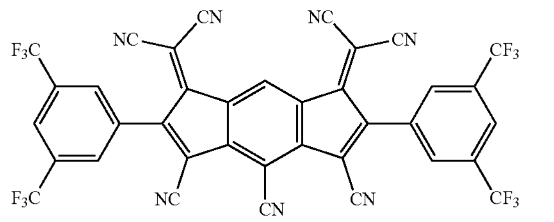

-continued

PD-32

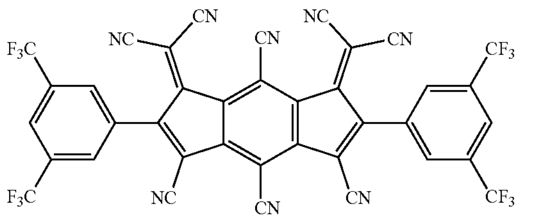

PD-33

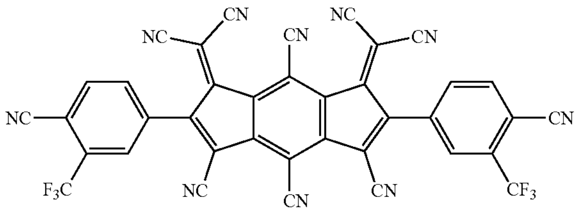

PD-34

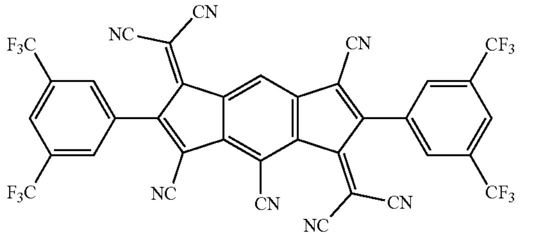

PD-35

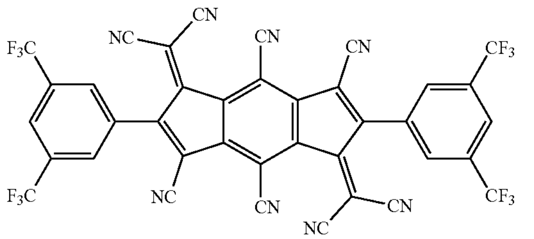

PD-36

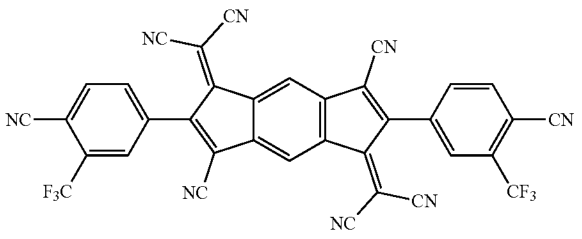

Figure 10:
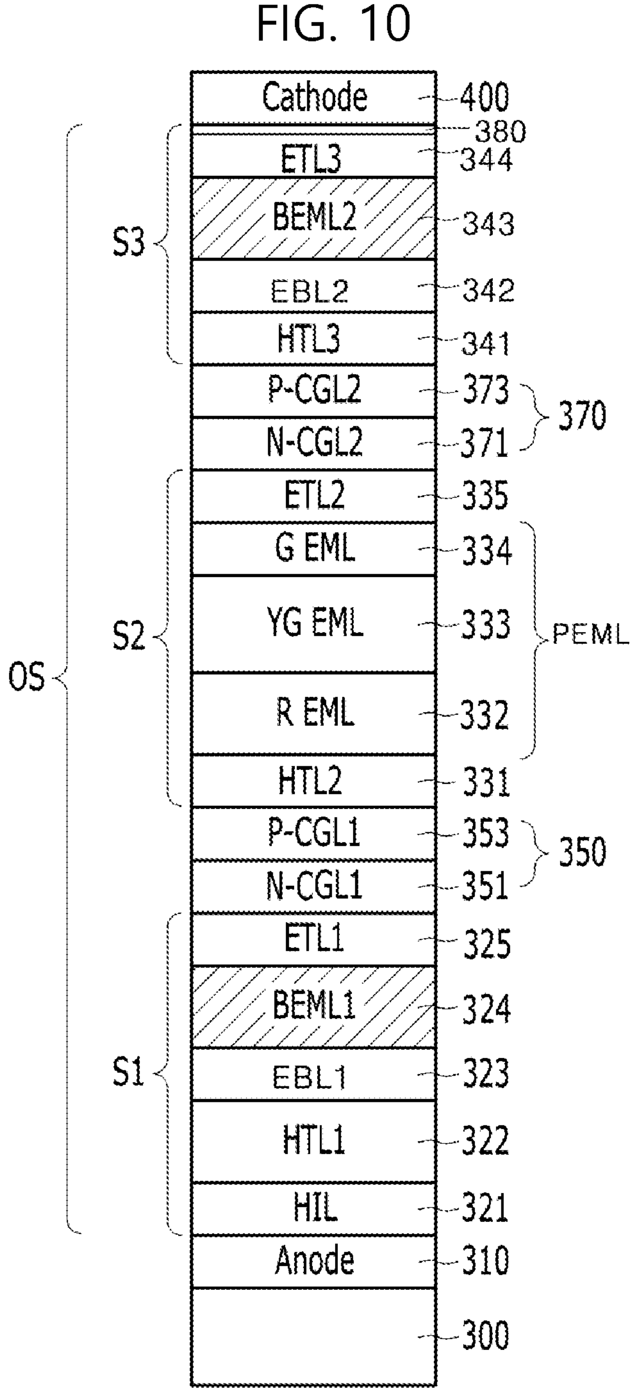
FIG. 10 is a light emitting device to which a seventh experimental example group and an eighth experimental example group are applied according to one embodiment.
Figure 11A:
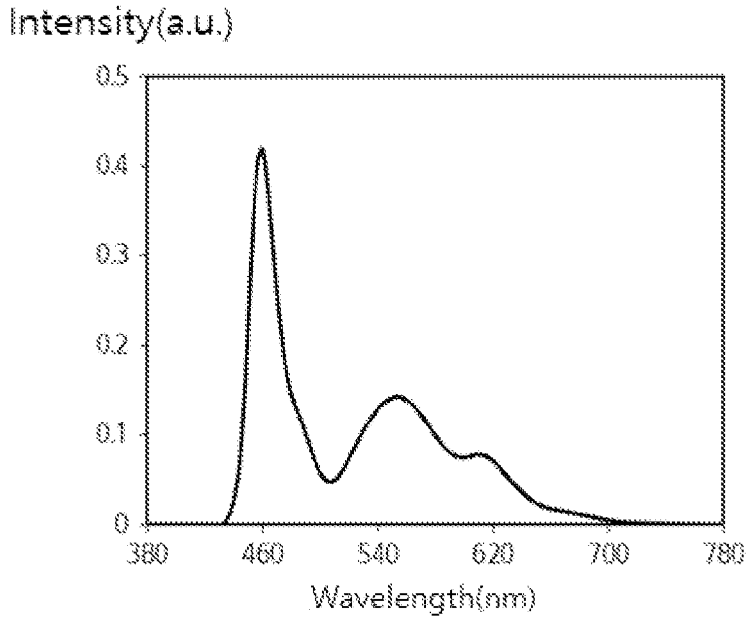
FIGS. 11A and 11B are graphs showing emission spectra of the seventh experimental example group and the eighth experimental example group, respectively according to one embodiment.
Figure 11B:
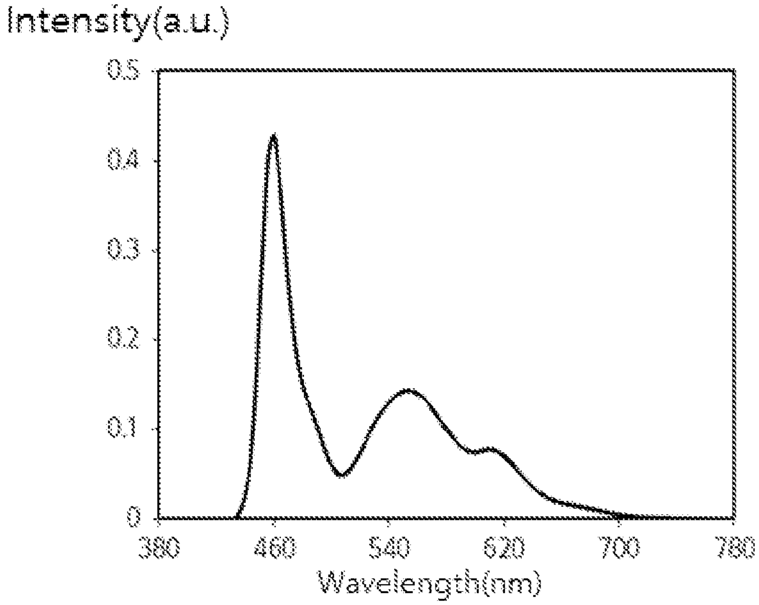

FIG. 10 illustrates light emitting devices to which the seventh experimental example group and the eighth experimental example group are applied according to one embodiment, and FIGS. 11A and 11B are graphs showing the emission spectra of the seventh experimental example group and the eighth experimental example group, respectively, according to one embodiment.

Hereinafter, the light emitting devices of the seventh experimental example group (Ex7-1 to Ex7-44) and the eighth experimental example group (Ex8-1 to Ex8-54) are formed using the stacked structure shown in FIG. 10 in the following process.

An anode 310 containing ITO is formed on a substrate 300.

Then, $MgF_2$ is deposited to a thickness of 5 nm to form a hole injection layer (HIL) 321.

Then, DNTPD is deposited to a thickness of 100 nm to form a first hole transport layer (HTL1) 322.

Then, TCTA is deposited to a thickness of 5 nm to form a first electron-blocking layer (EBL1) 323.

Then, a first blue light emitting layer (BEML1) 324 having a thickness of 20 nm is formed using MADN as a host bh and doping 5 wt % of DABNA-1 with a blue dopant bd.

Then, a first electron transport layer (ETL1) 325 is formed to a thickness of 15 nm using one selected from the above-mentioned materials of ETM-01 to ETM-60.

Then, a first n-type charge generation layer N-CGL1 351 having a thickness of 15 nm is formed using Bphen as a host and doping with 2 wt % of lithium (Li).

Then, a first p-type charge generation layer P-CGL1 353 having a thickness of 7 nm is formed using DNTPB as a host and doping with 20 wt % of the above-described p-type dopants of PD-01 to PD-36.

The first n-type charge generation layer N-CGL1 351 and the p-type charge generation layer P-CGL1 353 constitutes a first charge generation layer 350.

Then, BPBPA is deposited to a thickness of 20 nm to form a second hole transport layer (HTL2) 331.

Then, a red phosphorescent light emitting layer (R EML) 332 having a thickness of 10 nm is formed using BPBPA and TPBi as hosts at a weight ratio of 1:1 and then doping with 5 wt % $Ir(piq)_2acac$.

Then, a yellow-green phosphorescent light emitting layer (YG EML) 333 having a thickness of 20 nm is formed using CBP and TPBi as hosts at a weight ratio of 1:1 and then doping with 15 wt % PD-01.

Then, a green phosphorescent light emitting layer (G EML) 334 having a thickness of 10 nm is formed using CBP and TPBi as hosts at a weight ratio of 1:1 and then doping with 15 wt % $Ir(ppy)_3$.

Then, TPBi is deposited to a thickness of 20 nm to form a second electron transport layer (ETL2) 335.

Then, a second n-type charge generation layer N-CGL2 371 is formed using Bphen as a host and doping with 3 wt % Li.

Then, a second p-type charge generation layer P-CGL2 373 is formed using DNTPD as a host and doping with 20 wt % of any of the above-described p-type dopants of PD-01 to PD-03.

The second n-type charge generation layer N-CGL2 371 and the p-type charge generation layer P-CGL2 373 constitutes a first charge generation layer 370.

Then, a third hole transport layer (HTL3) 341 is formed to a thickness of 100 nm using DNTPD.

Then, a second electron-blocking layer (EBL2) 342 is formed to a thickness of 5 nm using TCTA.

Then, a second blue light emitting layer (BEML2) 343 is formed to a thickness of 200 nm using MADN as a host and doping with DABNA-1 at 5 wt %.

Then, a third electron transport layer (ETL3) 344 is formed to a thickness of 20 nm using ZADN.

Then, LiF is deposited to a thickness of 1.5 nm to form an electron injection layer 380.

Then, Al is deposited to a thickness of 100 nm to form a cathode 400, thereby forming a light emitting device.

The following experimental examples were performed while changing the materials of the first electron transport layer 325 and the first p-type charge generation layer 353 on both sides of the first n-type charge generation layer 351 in the light emitting device shown in FIG. 10.

In each of Experimental Examples Ex7-1 to Ex7-44 of the seventh experimental example group, the material of the p-type dopant of the first p-type charge generation layer and the material of the first electron transport layer in the light emitting device of FIG. 10 were changed as shown in the following reference table.

[Reference Table 1]

| Structure | p-dopant | ETL1 |
|---|---|---|
| Ex7-1 | PD-01 | ETM-02 |
| Ex7-2 | PD-01 | ETM-07 |
| Ex7-3 | PD-01 | ETM-14 |
| Ex7-4 | PD-01 | ETM-22 |
| Ex7-5 | PD-01 | ETM-28 |
| Ex7-6 | PD-01 | ETM-35 |
| Ex7-7 | PD-01 | ETM-37 |
| Ex7-8 | PD-01 | ETM-46 |
| Ex7-9 | PD-01 | ETM-54 |
| Ex7-10 | PD-02 | ETM-02 |
| Ex7-11 | PD-02 | ETM-07 |
| Ex7-12 | PD-02 | ETM-14 |
| EX7-13 | PD-02 | ETM-22 |
| EX7-14 | PD-02 | ETM-28 |
| Ex7-15 | PD-02 | ETM-35 |
| Ex7-16 | PD-02 | ETM-37 |
| Ex7-17 | PD-02 | ETM-46 |
| Ex7-18 | PD-02 | ETM-54 |
| Ex7-19 | PD-03 | ETM-02 |
| Ex7-20 | PD-03 | ETM-07 |

-continued

[Reference Table 1]

| Structure | p-dopant | ETL1 |
|---|---|---|
| Ex7-21 | PD-03 | ETM-14 |
| Ex7-22 | PD-03 | ETM-22 |
| Ex7-23 | PD-03 | ETM-28 |
| Ex7-24 | PD-03 | ETM-35 |
| Ex7-25 | PD-03 | ETM-37 |
| Ex7-26 | PD-03 | ETM-46 |
| Ex7-27 | PD-03 | ETM-54 |
| Ex7-28 | PD-04 | ZADN |
| Ex7-29 | PD-05 | ZADN |
| Ex7-30 | PD-06 | ZADN |
| Ex7-31 | PD-07 | ZADN |
| Ex7-32 | PD-08 | ZADN |
| Ex7-33 | PD-09 | ZADN |
| Ex7-34 | PD-10 | ZADN |
| Ex7-35 | PD-11 | ZADN |
| Ex7-36 | PD-12 | ZADN |
| Ex7-37 | PD-13 | ZADN |
| Ex7-38 | PD-14 | ZADN |
| Ex7-39 | PD-16 | ZADN |
| Ex7-40 | PD-20 | ZADN |
| Ex7-41 | PD-22 | ZADN |
| Ex7-42 | PD-24 | ZADN |
| Ex7-43 | PD-26 | ZADN |
| Ex7-44 | PD-30 | ZADN |

As shown in Table 7, the seventh experimental example group (Ex7-1 to Ex7-44) yielded the following results.

TABLE 7

| | Voltage @ 10 mA/cm$^2$ (V) | R_Efficiency @10 mA/cm$^2$ (cd/A) | G_Efficiency @10 mA/cm$^2$ (cd/A) | B_Efficiency @10 mA/cm$^2$ (cd/A) | W_Efficiency @10 mA/cm$^2$ (cd/A) | CIEx | CIEy |
|---|---|---|---|---|---|---|---|
| Ex7-1 | 12.09 | 6.0 | 23.33 | 4.26 | 66.0 | 0.290 | 0.325 |
| Ex7-2 | 12.11 | 5.9 | 23.49 | 4.18 | 66.1 | 0.291 | 0.329 |
| Ex7-3 | 12.18 | 6.0 | 23.55 | 4.28 | 66.5 | 0.290 | 0.325 |
| Ex7-4 | 12.19 | 6.0 | 23.32 | 4.20 | 65.9 | 0.291 | 0.327 |
| Ex7-5 | 12.09 | 5.9 | 23.31 | 4.2 | 65.8 | 0.292 | 0.329 |
| Ex7-6 | 12.03 | 6.0 | 23.55 | 4.3 | 66.5 | 0.289 | 0.325 |
| Ex7-7 | 12.16 | 5.9 | 23.48 | 4.3 | 66.2 | 0.289 | 0.325 |
| Ex7-8 | 12.08 | 5.9 | 23.50 | 4.3 | 66.3 | 0.290 | 0.326 |
| Ex7-9 | 12.16 | 6.0 | 23.46 | 4.2 | 66.3 | 0.291 | 0.327 |
| Ex7-10 | 12.10 | 5.9 | 23.41 | 4.2 | 66.1 | 0.290 | 0.326 |
| Ex7-11 | 12.13 | 6.0 | 23.57 | 4.3 | 66.6 | 0.289 | 0.324 |
| Ex7-12 | 12.02 | 6.0 | 23.52 | 4.2 | 66.4 | 0.292 | 0.328 |
| Ex7-13 | 12.08 | 6.0 | 23.38 | 4.2 | 66.1 | 0.292 | 0.328 |
| Ex7-14 | 12.15 | 6.0 | 23.40 | 4.2 | 66.2 | 0.291 | 0.327 |
| Ex7-15 | 12.14 | 5.9 | 23.39 | 4.3 | 66.1 | 0.289 | 0.324 |
| Ex7-16 | 12.15 | 6.0 | 23.43 | 4.2 | 66.2 | 0.293 | 0.330 |
| Ex7-17 | 12.19 | 6.0 | 23.38 | 4.2 | 66.1 | 0.293 | 0.329 |
| Ex7-18 | 12.09 | 5.9 | 23.58 | 4.3 | 66.4 | 0.289 | 0.326 |
| Ex7-19 | 12.16 | 6.0 | 23.48 | 4.2 | 66.2 | 0.292 | 0.329 |
| Ex7-20 | 12.12 | 6.0 | 23.54 | 4.3 | 66.5 | 0.289 | 0.324 |
| Ex7-21 | 12.00 | 5.9 | 23.36 | 4.2 | 65.8 | 0.291 | 0.329 |
| Ex7-22 | 12.20 | 5.9 | 23.47 | 4.2 | 66.2 | 0.291 | 0.328 |
| Ex7-23 | 12.06 | 6.0 | 23.36 | 4.3 | 66.2 | 0.291 | 0.325 |
| Ex7-24 | 12.06 | 6.0 | 23.53 | 4.2 | 66.4 | 0.291 | 0.328 |
| Ex7-25 | 12.20 | 6.0 | 23.62 | 4.3 | 66.7 | 0.289 | 0.324 |
| Ex7-26 | 12.02 | 6.0 | 23.51 | 4.2 | 66.3 | 0.291 | 0.328 |
| Ex7-27 | 12.01 | 6.0 | 23.45 | 4.3 | 66.4 | 0.289 | 0.324 |
| Ex7-28 | 12.11 | 6.0 | 23.48 | 4.1 | 66.3 | 0.290 | 0.325 |
| Ex7-29 | 12.11 | 5.9 | 23.28 | 4.1 | 65.7 | 0.290 | 0.327 |
| Ex7-30 | 12.05 | 5.9 | 23.31 | 4.0 | 65.8 | 0.290 | 0.327 |
| Ex7-31 | 12.16 | 6.0 | 23.35 | 4.15 | 65.9 | 0.293 | 0.330 |
| Ex7-32 | 12.10 | 6.0 | 23.12 | 4.02 | 65.3 | 0.296 | 0.334 |
| Ex7-33 | 12.13 | 6.0 | 23.44 | 4.10 | 66.0 | 0.294 | 0.333 |
| Ex7-34 | 12.01 | 5.9 | 23.20 | 4.09 | 65.5 | 0.294 | 0.332 |
| Ex7-35 | 12.18 | 5.9 | 23.21 | 4.1 | 65.4 | 0.293 | 0.331 |
| Ex7-36 | 12.14 | 6.0 | 23.27 | 4.0 | 65.6 | 0.295 | 0.335 |
| Ex7-37 | 12.09 | 6.0 | 23.18 | 4.1 | 65.5 | 0.295 | 0.333 |
| Ex7-38 | 12.05 | 5.9 | 23.43 | 4.1 | 65.9 | 0.294 | 0.334 |
| Ex7-39 | 12.16 | 5.9 | 23.32 | 4.0 | 65.6 | 0.295 | 0.335 |
| Ex7-40 | 12.10 | 5.9 | 23.30 | 4.1 | 65.6 | 0.294 | 0.334 |

TABLE 7-continued

| | Voltage @ 10 mA/cm$^2$ (V) | R_Efficiency @10 mA/cm$^2$ (cd/A) | G_Efficiency @10 mA/cm$^2$ (cd/A) | B_Efficiency @10 mA/cm$^2$ (cd/A) | W_Efficiency @10 mA/cm$^2$ (cd/A) | CIEx | CIEy |
|---|---|---|---|---|---|---|---|
| Ex7-41 | 12.07 | 6.0 | 23.46 | 4.2 | 66.2 | 0.293 | 0.330 |
| Ex7-42 | 12.01 | 6.0 | 23.24 | 4.1 | 65.6 | 0.295 | 0.333 |
| Ex7-43 | 12.20 | 5.9 | 23.11 | 4.0 | 65.2 | 0.296 | 0.335 |
| Ex7-44 | 12.11 | 6.0 | 23.31 | 4.0 | 65.7 | 0.296 | 0.336 |

Experimental Examples Ex7-1 to Ex7-27 of the seventh experimental example group used any one of PD-01, Pd-02, and PD-03 as the p-type organic dopant, and exhibited a driving voltage of about 12V and a blue light emission efficiency (B_efficiency) of about 4.2 Cd/A on average. Experimental Examples Ex7-28 to Ex7-44 of the seventh experimental example group exhibited device characteristics when the first electron transport layer contained a single material of ZADN, had a driving voltage slightly higher than 12V, and had no great variation in light emission efficiency.

Hereinafter, the experiments of the eighth experimental example group (Ex8-1 to Ex8-54) using the fourth material C4 of Formula 4, having excellent hole transport ability as a p-type dopant, will be described. The experiments were performed under the conditions that the p-type dopant of the first p-type charge generation layer used in the experimental example of the eighth experimental example group was PD-04, PD-06, PD-12, PD-20, PD-22, or PD-30, and the material of each first electron transport layer was changed to ETM-02, ETM-07, ETM-14, ETM-22, ETM-28, ETM-35, ETM-37, ETM-46, or ETM-54.

In each of Experimental Examples Ex8-1 to Ex8-54 of the eighth Experimental Example group, the p-type dopant of the first p-type charge generation layer and the material of the first electron transport layer were changed in the light emitting device of FIG. 10, as shown in Reference Table 2 below.

[Reference Table 2]

| | p-dopant | ETL1 |
|---|---|---|
| Ex8-1 | PD-04 | ETM-02 |
| Ex8-2 | PD-04 | ETM-07 |
| Ex8-3 | PD-04 | ETM-14 |
| Ex8-4 | PD-04 | ETM-22 |
| Ex8-5 | PD-04 | ETM-28 |
| Ex8-6 | PD-04 | ETM-35 |
| Ex8-7 | PD-04 | ETM-37 |
| Ex8-8 | PD-04 | ETM-46 |
| Ex8-9 | PD-04 | ETM-54 |
| Ex8-10 | PD-06 | ETM-02 |
| Ex8-11 | PD-06 | ETM-07 |
| Ex8-12 | PD-06 | ETM-14 |
| Ex8-13 | PD-06 | ETM-22 |

-continued

[Reference Table 2]

| | p-dopant | ETL1 |
|---|---|---|
| Ex8-14 | PD-06 | ETM-28 |
| Ex8-15 | PD-06 | ETM-35 |
| Ex8-16 | PD-06 | ETM-37 |
| Ex8-17 | PD-06 | ETM-46 |
| Ex8-18 | PD-06 | ETM-54 |
| Ex8-19 | PD-12 | ETM-02 |
| Ex8-20 | PD-12 | ETM-07 |
| Ex8-21 | PD-12 | ETM-14 |
| Ex8-22 | PD-12 | ETM-22 |
| Ex8-23 | PD-12 | ETM-28 |
| Ex8-24 | PD-12 | ETM-35 |
| Ex8-25 | PD-12 | ETM-37 |
| Ex8-26 | PD-12 | ETM-46 |
| Ex8-27 | PD-12 | ETM-54 |
| Ex8-28 | PD-20 | ETM-02 |
| Ex8-29 | PD-20 | ETM-07 |
| Ex8-30 | PD-20 | ETM-14 |
| Ex8-31 | PD-20 | ETM-22 |
| Ex8-32 | PD-20 | ETM-28 |
| Ex8-33 | PD-20 | ETM-35 |
| Ex8-34 | PD-20 | ETM-37 |
| Ex8-35 | PD-20 | ETM-46 |
| Ex8-36 | PD-20 | ETM-54 |
| Ex8-37 | PD-22 | ETM-02 |
| Ex8-38 | PD-22 | ETM-07 |
| Ex8-39 | PD-22 | ETM-14 |
| Ex8-40 | PD-22 | ETM-22 |
| Ex8-41 | PD-22 | ETM-28 |
| Ex8-42 | PD-22 | ETM-35 |
| Ex8-43 | PD-22 | ETM-37 |
| Ex8-44 | PD-22 | ETM-46 |
| EX8-45 | PD-22 | ETM-54 |
| Ex8-46 | PD-30 | ETM-02 |
| Ex8-47 | PD-30 | ETM-07 |
| Ex8-48 | PD-30 | ETM-14 |
| Ex8-49 | PD-30 | ETM-22 |
| Ex8-50 | PD-30 | ETM-28 |
| EX8-51 | PD-30 | ETM-35 |
| Ex8-52 | PD-30 | ETM-37 |
| Ex8-53 | PD-30 | ETM-46 |
| Ex8-54 | PD-30 | ETM-54 |

In addition, the results for the eighth experimental example group (Ex8-1 to Ex8-54) are shown in Table 8 below.

TABLE 8

| | Voltage @ 10 mA/cm$^2$ (V) | R_Efficiency @10 mA/cm$^2$ (cd/A) | G_Efficiency @10 mA/cm$^2$ (cd/A) | B_Efficiency @10 mA/cm$^2$ (cd/A) | W_Efficiency @10 mA/cm$^2$ (cd/A) | CIEx | CIEy |
|---|---|---|---|---|---|---|---|
| Ex8-1 | 11.36 | 6.0 | 23.57 | 4.33 | 66.5 | 0.288 | 0.323 |
| Ex8-2 | 11.39 | 6.0 | 23.55 | 4.23 | 66.5 | 0.291 | 0.328 |
| Ex8-3 | 11.42 | 5.9 | 23.38 | 4.31 | 66.1 | 0.288 | 0.323 |
| Ex8-4 | 11.41 | 6.0 | 23.50 | 4.26 | 66.4 | 0.291 | 0.326 |
| Ex8-5 | 11.35 | 6.0 | 23.71 | 4.3 | 66.9 | 0.288 | 0.324 |
| Ex8-6 | 11.35 | 5.9 | 23.55 | 4.2 | 66.2 | 0.291 | 0.330 |
| Ex8-7 | 11.48 | 6.0 | 23.35 | 4.2 | 66.0 | 0.292 | 0.329 |

TABLE 8-continued

| | Voltage @ 10 mA/cm$^2$ (V) | R_Efficiency @10 mA/cm$^2$ (cd/A) | G_Efficiency @10 mA/cm$^2$ (cd/A) | B_Efficiency @10 mA/cm$^2$ (cd/A) | W_Efficiency @10 mA/cm$^2$ (cd/A) | CIEx | CIEy |
|---|---|---|---|---|---|---|---|
| Ex8-8 | 11.38 | 6.0 | 23.50 | 4.3 | 66.4 | 0.289 | 0.324 |
| Ex8-9 | 11.34 | 5.9 | 23.55 | 4.3 | 66.4 | 0.287 | 0.323 |
| Ex8-10 | 11.42 | 6.0 | 23.37 | 4.2 | 66.0 | 0.292 | 0.328 |
| Ex8-11 | 11.32 | 6.0 | 23.26 | 4.2 | 65.8 | 0.291 | 0.327 |
| Ex8-12 | 11.33 | 6.0 | 23.47 | 4.2 | 66.3 | 0.292 | 0.329 |
| Ex8-13 | 11.45 | 6.0 | 23.55 | 4.3 | 66.5 | 0.290 | 0.327 |
| Ex8-14 | 11.49 | 6.0 | 23.67 | 4.3 | 66.8 | 0.289 | 0.324 |
| Ex8-15 | 11.32 | 5.9 | 23.50 | 4.3 | 66.3 | 0.287 | 0.323 |
| Ex8-16 | 11.42 | 5.9 | 23.27 | 4.2 | 65.7 | 0.292 | 0.328 |
| Ex8-17 | 11.40 | 5.9 | 23.32 | 4.3 | 65.9 | 0.289 | 0.325 |
| Ex8-18 | 11.35 | 5.9 | 23.49 | 4.3 | 66.2 | 0.288 | 0.323 |
| EX8-19 | 11.42 | 6.0 | 23.45 | 4.3 | 66.3 | 0.290 | 0.325 |
| Ex8-20 | 11.43 | 5.9 | 23.34 | 4.3 | 66.0 | 0.289 | 0.325 |
| EX8-21 | 11.42 | 6.0 | 23.46 | 4.3 | 66.4 | 0.288 | 0.323 |
| Ex8-22 | 11.35 | 6.0 | 23.65 | 4.3 | 66.8 | 0.289 | 0.325 |
| Ex8-23 | 11.47 | 5.9 | 23.54 | 4.3 | 66.4 | 0.288 | 0.325 |
| Ex8-24 | 11.48 | 6.0 | 23.50 | 4.3 | 66.4 | 0.289 | 0.324 |
| EX8-25 | 11.44 | 5.9 | 23.47 | 4.3 | 66.2 | 0.289 | 0.325 |
| Ex8-26 | 11.43 | 6.0 | 23.51 | 4.3 | 66.5 | 0.289 | 0.324 |
| Ex8-27 | 11.32 | 6.0 | 23.66 | 4.3 | 66.8 | 0.288 | 0.324 |
| Ex8-28 | 11.42 | 6.0 | 23.65 | 4.3 | 66.8 | 0.289 | 0.324 |
| Ex8-29 | 11.42 | 6.0 | 23.50 | 4.2 | 66.3 | 0.292 | 0.328 |
| Ex8-30 | 11.45 | 5.9 | 23.41 | 4.2 | 66.1 | 0.290 | 0.326 |
| Ex8-31 | 11.35 | 6.0 | 23.58 | 4.2 | 66.5 | 0.291 | 0.327 |
| Ex8-32 | 11.32 | 5.9 | 23.24 | 4.2 | 65.7 | 0.290 | 0.327 |
| Ex8-33 | 11.36 | 5.9 | 23.34 | 4.3 | 65.9 | 0.288 | 0.324 |
| Ex8-34 | 11.37 | 6.0 | 23.56 | 4.3 | 66.5 | 0.289 | 0.324 |
| Ex8-35 | 11.45 | 5.9 | 23.49 | 4.3 | 66.2 | 0.288 | 0.324 |
| Ex8-36 | 11.32 | 6.0 | 23.52 | 4.3 | 66.5 | 0.289 | 0.323 |
| Ex8-37 | 11.34 | 5.9 | 23.41 | 4.3 | 66.1 | 0.289 | 0.326 |
| Ex8-38 | 11.50 | 6.0 | 23.56 | 4.3 | 66.6 | 0.289 | 0.324 |
| Ex8-39 | 11.34 | 5.9 | 23.58 | 4.2 | 66.4 | 0.291 | 0.328 |
| Ex8-40 | 11.30 | 6.0 | 23.66 | 4.3 | 66.8 | 0.289 | 0.324 |
| Ex8-41 | 11.44 | 5.9 | 23.27 | 4.3 | 65.8 | 0.289 | 0.323 |
| Ex8-42 | 11.33 | 6.0 | 23.39 | 4.3 | 66.1 | 0.290 | 0.326 |
| Ex8-43 | 11.33 | 6.0 | 23.47 | 4.2 | 66.2 | 0.292 | 0.329 |
| Ex8-44 | 11.47 | 6.0 | 23.55 | 4.3 | 66.5 | 0.289 | 0.324 |
| Ex8-45 | 11.30 | 5.9 | 23.36 | 4.2 | 66.0 | 0.290 | 0.326 |
| Ex8-46 | 11.34 | 6.0 | 23.41 | 4.2 | 66.2 | 0.291 | 0.327 |
| Ex8-47 | 11.32 | 5.9 | 23.23 | 4.2 | 65.6 | 0.290 | 0.326 |
| Ex8-48 | 11.44 | 6.0 | 23.33 | 4.3 | 66.1 | 0.289 | 0.323 |
| Ex8-49 | 11.38 | 6.0 | 23.38 | 4.2 | 66.0 | 0.292 | 0.329 |
| Ex8-50 | 11.34 | 6.0 | 23.48 | 4.2 | 66.3 | 0.292 | 0.328 |
| Ex8-51 | 11.45 | 6.0 | 23.39 | 4.3 | 66.2 | 0.290 | 0.325 |
| Ex8-52 | 11.32 | 5.9 | 23.31 | 4.3 | 65.9 | 0.290 | 0.325 |
| Ex8-53 | 11.33 | 6.0 | 23.51 | 4.3 | 66.5 | 0.289 | 0.324 |
| Ex8-54 | 11.39 | 5.9 | 23.31 | 4.2 | 65.8 | 0.291 | 0.328 |

In Table 8, the eighth experimental example group (Ex8-1 to Ex8-54) exhibited a blue light emission efficiency (B efficiency) of 4.2 Cd/A and a driving voltage of 11.3V on average, which is about 0.7V lower than that of the seventh experimental example group (Ex7-1 to Ex7-44). FIG. 11A shows a white emission spectrum corresponding to Ex7-1 in the seventh experimental example group and FIG. 11B shows a white emission spectrum corresponding to Ex8-1 in the eighth experimental example group.

Regarding the white emission spectrum of each of the seventh experimental example group and the eighth experimental example group, each of them includes a blue light emitting layer in the light emitting device and thus exhibits high blue light emission efficiency, and includes a red phosphorescent light emitting layer, a yellow-green phosphorescent light emitting layer and a green phosphorescent light emitting layer in the phosphorescent stack.

That is, the experimental results for the seventh and eighth experimental example groups showed that the electron transport layer and the p-type charge generation layer adjacent to each other with the n-type charge generation layer therebetween maintain a predetermined efficiency or higher and the driving voltage is reduced when materials having excellent electron transport ability and hole generation ability are used.

Hereinafter, a light emitting display device to which the light emitting device described above is applied will be described.

Figure 12:
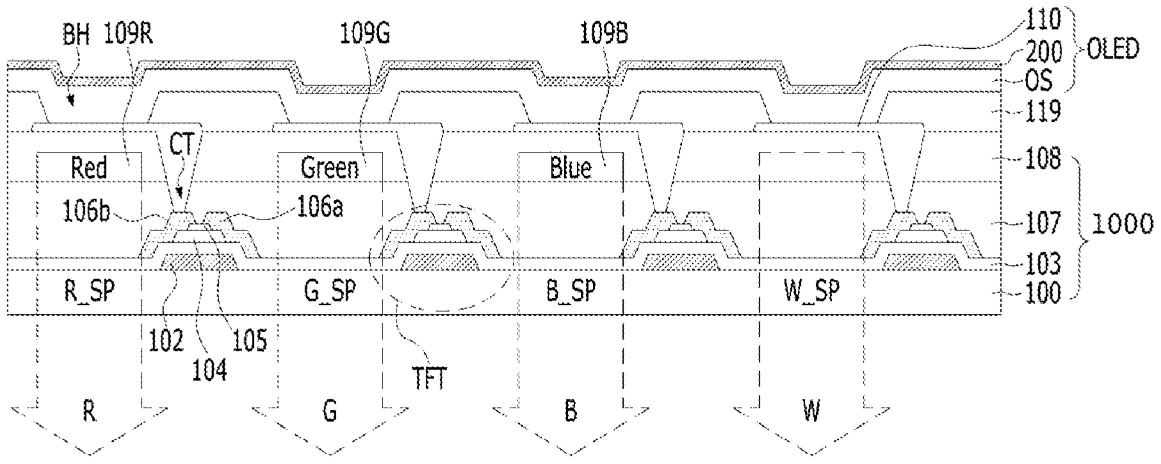
FIG. 12 is a cross-sectional view illustrating a light emitting display device according to one embodiment of the present disclosure.

FIG. 12 is a cross-sectional view illustrating a light emitting display device according to the present disclosure.

The light emitting device may be commonly applied to a plurality of subpixels to emit white light.

As shown in FIG. 12, the light emitting display device of the present disclosure includes a substrate 100 having a plurality of subpixels R_SP, G_SP, B_SP, and W_SP emitting red light R, green light G, blue light B and white light W, respectively, a light emitting device (also referred to as "OLED, organic light emitting diode") commonly provided on the substrate 100, a thin film transistor (TFT) provided in each of the subpixels and connected to the anode 110 of the light emitting device (OLED) and a color filter 109R, 109G or 109B provided below the anode 110 of at least one of the subpixels.

The illustrated example relates to a configuration including the white subpixel W_SP, but the present disclosure is not limited thereto. A configuration in which the white subpixel W_SP is omitted and only the red, green, and blue subpixels R_SP, G_SP, and B_SP are provided is also possible. In some cases, a combination of a cyan subpixel, a magenta subpixel, and a yellow subpixel capable of creating white by replacing the red, green, and blue subpixels is possible.

The thin film transistor TFT includes, for example, a gate electrode 102, a semiconductor layer 104, and a source electrode 106*a* and a drain electrode 106*b* connected to respective sides of the semiconductor layer 104. In addition, a channel protection layer 105 may be further provided on the portion where the channel of the semiconductor layer 104 is located in order to prevent direct connection between the source and drain electrodes 106*a* and 106*b*.

A gate insulating layer 103 is provided between the gate electrode 102 and the semiconductor layer 104.

The semiconductor layer 104 may be formed of, for example, an oxide semiconductor, amorphous silicon, polycrystalline silicon, or a combination thereof. For example, when the semiconductor layer 104 is an oxide semiconductor, the heating temperature required for forming the thin film transistor can be lowered, and thus the substrate 100 can be selected from among a greater variety of available types thereof, so the semiconductor layer 104 can be advantageously applied to a flexible display device.

In addition, the drain electrode 106*b* of the thin film transistor TFT may be connected to the anode 110 in a contact hole CT provided in the first and second passivation layers 107 and 108.

The first passivation layer 107 is provided to primarily protect the thin film transistor TFT, and color filters 109R, 109G, and 109B may be provided thereon.

When the plurality of subpixels includes a red subpixel, a green subpixel, a blue subpixel, and a white subpixel, the color filter may include first to third color filters 109R, 109G, and 109B in the remaining subpixels, respectively, excluding the white subpixel W_SP, and allows the emitted white light to pass through the anode 110 for each wavelength. A second passivation layer 108 is formed under the anode 110 to cover the first to third color filters 109R, 109G, and 109B. The anode 110 is formed on the surface of the second passivation layer 108 and connected to the thin film transistor TFT through the contact hole CT.

Here, a configuration from the substrate 100 to the thin film transistor TFT, color filters 109R, 109G, and 109B, and the first and second passivation layers 107 and 108 is referred to as a “thin film transistor array substrate” 1000.

The light emitting device OLED is formed on the thin film transistor array substrate 1000 including the bank 119 defining a light emitting part BH. The light emitting device OLED, for example, includes a transparent anode 110, a cathode 200 that faces the anode 110 and is formed of a reflective electrode, and an electron transport and blocking unit ETBU disposed in each of the blue light emitting stacks S1 and S3, among the stacks divided by the first and second charge generation layers 150 and 170, between the anode 110 and the cathode 200, as described with reference to FIGS. 1, 2A, 2B and 5, wherein the electron transport and blocking unit ETBU includes an electron-blocking layer 123 or 142 formed of the electron-blocking material of Formula 2, a blue light emitting layer 124 or 143 containing a boron-based blue dopant and an electron transport layer 125 or 144 containing the electron transport material of Formula 1.

The anode 110 is divided for each subpixel, and the remaining layers of the white light emitting device OLED are integrally provided in the entire display area, rather than being divided into individual subpixels.

Meanwhile, the light emitting device OLED including an internal stack OS between the anode 110 and the cathode 200 may include the structure of the light emitting device described with reference to FIGS. 1, 2A, 2B and 3, the structure of the light emitting device described with reference to FIG. 7, and the structure of the light emitting device described with reference to FIG. 10. Alternatively, the electron transport layer, the electron-blocking layer, and the p-type organic dopant of each experimental example may be disposed in another stack or charge generation layer.

One feature of the light emitting device (OLED) of the present disclosure is that the internal stack OS in the light emitting device OLED includes at least a blue fluorescent stack and a phosphorescent stack, and the electron transport layer of the blue fluorescent stack, contacting the cathode, is formed of a mixture of a first material of Formula 1, having high electron transport capability, and a second material having excellent electron injection efficiency without a force repelling the electron injection layer.

Another feature of the light emitting device (OLED) of the present disclosure is that, when the electron transport layer includes the first material of Formula 1, the material of the electron-blocking layer facing the blue fluorescent light emitting layer is substituted with deuterium to prevent electrons from accumulating at the interface between the electron-blocking layer and the blue fluorescent light emitting layer based on the excellent electron transport efficiency of the material.

Another feature of the light emitting device (OLED) of the present disclosure is that the electron transport layer and the p-type charge generation layer disposed on respective sides of the n-type charge generation layer are formed of materials having excellent electron transport efficiency and hole generation efficiency, respectively, thereby maintaining the balance between holes and electrons and reducing the driving voltage. In this case, one of the materials of Formula 1 may be used for the electron transport layer, and one of the materials of Formula 4 may be used as the dopant of the p-type charge generation layer.

In the light emitting device of the present disclosure, when the electron transport layer formed of a material having high electron transport capability is applied, the material of the electron-blocking layer contacting the blue fluorescent light emitting layer is substituted with deuterium, thereby preventing or at least reducing accumulation of electrons or excitons at the interface between the blue fluorescent light emitting layer and the electron-blocking layer, and providing the effects of improving driving voltage, luminance and quantum efficiency without reducing the lifespan.

In addition, improving the efficiency in the blue fluorescent stack including the blue fluorescent light emitting layer can reduce the number of blue stacks required in a light emitting device realizing white light, and can thus reduce the number of stacks required to realize white with the same efficiency, thereby improving yield based on reduced driving voltage and simplified processing.

In the light emitting device and light emitting display device of the present disclosure, efficiency improvement, driving voltage reduction, and lifespan improvement can be achieved by changing the configuration of the peripheral layer of the blue light emitting layer in the blue fluorescent stack contacting the cathode.

The light emitting device according to an embodiment of the present disclosure includes n (wherein n is a natural number of 2 or more) stacks between an anode and a cathode facing each other, wherein an $n^{th}$ stack contacting the cathode is a first blue stack, wherein the first blue stack includes a first hole transport layer, a first electron-blocking layer, a first blue light emitting layer containing a boron-based dopant having an emission peak of 430 nm to 480 nm, a first electron transport layer contacting the first blue light emitting layer, and an electron injection layer having two sides contacting the first electron transport layer and the cathode, respectively, wherein the first electron transport layer contains a mixture of a first material of Formula 1 and a second material of Formula 2.

[Formula 1]

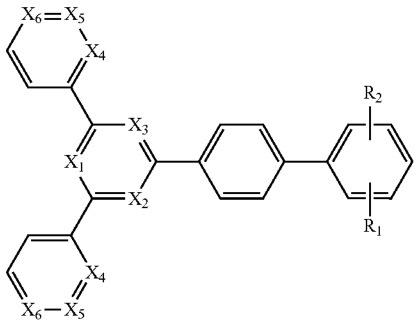

$R_1$ and $R_2$ are each independently selected from a cycloalkyl group, an aryl group, a heteroaryl group, and a carbazole group. $X_1$, $X_2$ and $X_3$ are each independently N or CH. At least one of $X_4$, $X_5$ and $X_6$ must be N, and the remaining ones be CH.

[Formula 2]

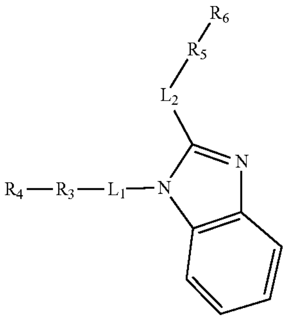

$L_1$ and $L_2$ may be independently a single bond. or $L_1$ and $L_2$ may independently include one selected from a phenyl group and a naphthyl group. In some embodiments, $L_1$ and $L_2$ may independently include one selected from a phenylene group and a naphthylene group.

$R_3$, $R_4$ and $R_6$ may independently include one selected from a phenyl group, a naphthyl group, and an anthracene group. $R_5$ may be a single bond or may include one selected from a methyl, an ethyl, a phenyl group, a naphthyl group, and an anthracene group.

In some embodiments, $R_3$ may be independently selected from a phenylene group, a naphthylene group, and an anthrylene group. $R_4$ may be selected from a phenyl group, a naphthyl group, and an anthracene group. $R_5$ may be a single bond or include an alkylene group, such as a phenylene group, a naphthylene group, and an anthrylene group. $R_6$ may be selected from an alkyl group such as a phenyl group, a naphthyl group, and an anthracene group.

The at least two stacks may further comprise a second blue stack contacting the anode and a phosphorescent stack between the first blue stack and the second blue stack.

The second blue stack may comprise a second electron transport layer, materials constituting the second electron transport layer being different from materials constituting the first electron transport layer.

The phosphorescent stack may comprise a third hole transport layer, a red phosphorescent light emitting layer, a green phosphorescent light emitting layer, and a third electron transport layer.

The phosphorescent stack may comprise a third hole transport layer, a red phosphorescent light emitting layer, a yellow-green phosphorescent light emitting layer, a green phosphorescent light emitting layer, and a third electron transport layer.

The electron injection layer may be a compound including a metal.

The electron injection layer may be LiF or Liq.

The thickness of the electron injection layer may be ⅛ to 1/100 of the thickness of the first electron transport layer.

In the first electron transport layer, the weight ratio of the first material to the second material may be 4:6 to 6:4.

The first electron-blocking layer may contain a third material represented by Formula 3.

[Formula 3]

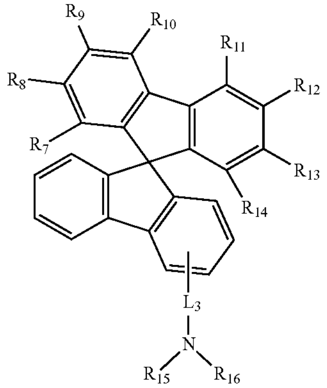

$L_3$ may be a single bond. Or $L_3$ may include one selected from a phenyl group or a naphthyl group. In some embodiments, $L_3$ is selected from a phenylene group and a naphthylene group. $R_7$ to $R_{14}$ may be deuterium. Or $R_7$ to $R_{14}$ may be substituted with deuterium. $R_{15}$ and $R_{16}$ may be independently selected from a phenyl group, a deuterium-substituted phenyl group, a biphenyl group, a deuterium-substituted biphenyl group, a fluorenyl group, a deuterium-substituted fluorenyl group, a heteroaryl group, a deuterium-substituted heteroaryl group, a carbazole group, a deuterium-substituted carbazole group, a dibenzofuran group, a deuterium-substituted dibenzofuran group, a dibenzothiophene group, and a deuterium-substituted dibenzothiophene group.

At least one of the stacks closer to the anode than the $n^{th}$ stack is a second blue stack, wherein the second blue stack includes a second hole transport layer, a second electron-blocking layer, a second blue light emitting layer containing a boron-based dopant having an emission peak of 430 nm to 480 nm, and a second electron transport layer contacting the second blue light emitting layer, and a charge generation unit including an n-type charge generation layer and a p-type charge generation layer is present between the second blue stack and the next stack adjacent to the second blue stack.

The second electron transport layer may include the first material and may not include the second material, and the second electron transport layer may contact the n-type charge generation layer.

The p-type charge generation layer may contain a fourth material of Formula 4 as a p-type dopant.

[Formula 4]

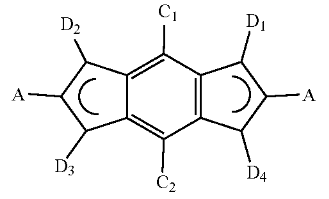

A is selected from hydrogen, deuterium, a halogen group, a cyano group, a malononitrile group, a trifluoromethyl group, a trifluoromethoxy group, a substituted or unsubstituted aryl or heteroaryl group, a substituted or unsubstituted $C_1$-$C_{12}$ alkyl group, a substituted or unsubstituted $C_1$-$C_{12}$ alkoxy group. In the Formula 2, a substituent of A may include one of a cyano group, a halogen group, a trifluoromethyl group, a trifluoromethoxy group, hydrogen and deuterium. $C_1$ and $C_2$ are each independently one of hydrogen, deuterium, a halogen group, or a cyano group. $D_1$ to $D_4$ are each independently connected by a single or double bond and are substituted with one of a halogen group, a cyano group, a malononitrile group, a trifluoromethyl group, and a trifluoromethoxy group, and at least two thereof include a cyano group.

The next stack adjacent to the second blue stack via the charge generation unit interposed therebetween may be a phosphorescent stack including at least a red phosphorescent light emitting layer.

The phosphorescent stack may further include a green light emitting layer or a yellow/green light emitting layer that contacts the red phosphorescent light emitting layer.

The n-type charge generation layer may include any one of an alkali metal, an alkaline earth metal, and a transition metal as an n-type dopant in the electron transport host.

The first blue stack may be adjacent to the phosphorescent stack opposite the cathode, and the first hole transport layer of first blue stack may contact the p-type charge generation layer including a p-type dopant.

The light emitting display device according to another embodiment of the present disclosure includes a substrate including a plurality of subpixels, a thin film transistor provided in each of the subpixels on the substrate, and the light emitting device connected to the thin film transistor.

The light emitting device of the present disclosure and a light emitting display device including the same have the following effects.

First, in the blue stack in contact with the cathode, the electron transport layer in contact with the electron injection layer made of an inorganic compound adjacent to the cathode is formed of two materials, thereby improving material efficiency and controlling the driving voltage.

Second, when a material having high electron transport capability is applied to the electron transport layer, the electron-blocking layer in contact with the blue fluorescent light emitting layer is formed of a deuterium-substituted material, thereby preventing accumulation of electrons or excitons at the interface between the blue fluorescent light emitting layer and the electron-blocking layer and obtaining effects of improving driving voltage, luminance, and quantum efficiency without reducing the lifespan.

Third, improvement in efficiency in a blue fluorescent stack having a blue fluorescent light emitting layer is capable of reducing the number of blue stacks required for a light emitting device realizing white and thus the number of stacks required to realize the same white color, thereby improving yield based on reduced driving voltage and simplified processing.

Fourth, the driving voltage can be reduced and the efficiency of realization of white color by the light emitting device implemented based on a plurality of stacks and color characteristics can be improved by changing the material of the p-type charge generation layer, which has different physical properties, between the blue fluorescent stack and the phosphorescent light emitting stack in the stack structure in which the blue fluorescent stack and the phosphorescent light emitting stack are connected.

It will be apparent to those skilled in the art that various modifications and variations can be made in the present disclosure without departing from the spirit or scope of the disclosure. Thus, it is intended that the present disclosure covers such modifications and variations thereto, provided they fall within the scope of the appended claims and their equivalents.

What is claimed is:

1. A light emitting device comprising:

at least two stacks between an anode and a cathode, wherein an $n^{th}$ stack contacting the cathode is a first blue stack, wherein the first blue stack comprises:

a first hole transport layer;

a first electron-blocking layer;

a first blue light emitting layer containing a boron-based dopant having an emission peak of 430 nm to 480 nm;

a first electron transport layer contacting the first blue light emitting layer; and an electron injection layer having two sides contacting the first electron transport layer and the cathode, respectively, wherein the first electron transport layer comprises a mixture of a first material and a second material,

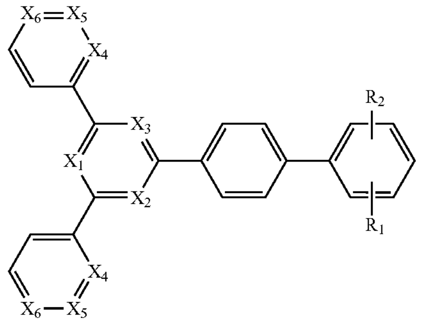

wherein $R_1$ and $R_2$ are each independently selected from a cycloalkyl group, an aryl group, a heteroaryl group, and an unsubstituted or aryl-substituted carbazole group;

$X_1$, $X_2$, $X_3$, $X_4$, $X_5$, and $X_6$ are each independently N or CH; and at least one of $X_4$, $X_5$, and $X_6$ is N, and wherein the second material is represented by Formula 2 below:

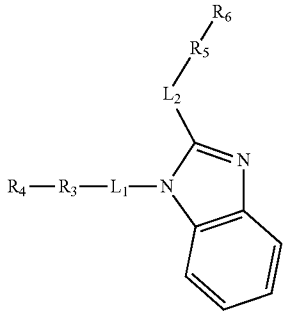

wherein $L_1$ and $L_2$ are independently selected from a single bond, a phenyl group and a naphthyl group;

$R_3$, $R_4$, and $R_6$ are independently selected from a phenyl group, a naphthyl group, and an anthracene group; and $R_5$ is a single bond, methyl, ethyl, a phenyl group, a naphthyl group, and an anthracene group.

2. The light emitting device according to claim 1, wherein the electron injection layer comprises a metal.

3. The light emitting device according to claim 1, wherein the electron injection layer comprises lithium fluoride LiF or Liq.

4. The light emitting device according to claim 1, wherein the electron injection layer has a thickness of ⅛ to 1/100 of a thickness of the first electron transport layer.

5. The light emitting device according to claim 1, wherein a weight ratio of the first material to the second material in the first electron transport layer is 4:6 to 6:4.

6. The light emitting device according to claim 1, wherein the first electron-blocking layer comprises a third material of Formula 3 below:

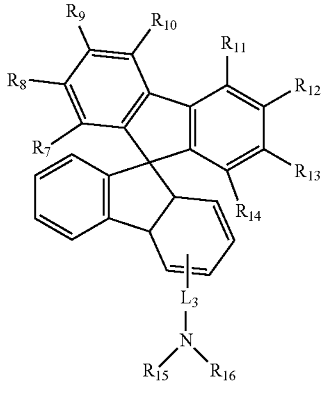

wherein $L_3$ is a single bond, a phenyl group, and a naphthyl group;

$R_7$ to $R_{14}$ are deuterium; and $R_{15}$ and $R_{16}$ are each independently selected from a phenyl group, a deuterium-substituted phenyl group, a biphenyl group, a deuterium-substituted biphenyl group, a fluorenyl group, a deuterium-substituted fluorenyl group, a heteroaryl group, a deuterium-substituted heteroaryl group, a carbazole group, a deuterium-substituted carbazole group, a dibenzofuran group, a deuterium-substituted dibenzofuran group, a dibenzothiophene group, and a deuterium-substituted dibenzothiophene group.

7. The light emitting device according to claim 1, wherein at least one among the stacks closer to the anode than the $n^{th}$ stack is a second blue stack, wherein the second blue stack comprises:

a second hole transport layer;

a second electron-blocking layer;

a second blue light emitting layer comprising a boron-based dopant having the emission peak of 430 nm to 480 nm; and a second electron transport layer contacting the second blue light emitting layer, wherein the light emitting device further comprises a charge generation unit comprising a first charge generation layer including an electron-transporting host and a second charge generation layer including a hole-transporting host between the second blue stack and a next stack adjacent to the second blue stack.

8. The light emitting device according to claim 7, wherein the second electron transport layer comprises the first material, but lacks the second material, and the second electron transport layer contacts the first charge generation layer.

9. The light emitting device according to claim 7, wherein the second charge generation layer comprises a fourth material of Formula 4 below as a dopant:

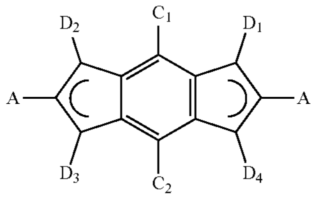

wherein A is selected from hydrogen, deuterium, a halogen group, a cyano group, a malononitrile group, a trifluoromethyl group, a trifluoromethoxy group, a substituted or unsubstituted aryl or heteroaryl group, a substituted or unsubstituted $C_1$-$C_{12}$ alkyl group, a substituted or unsubstituted $C_1$-$C_{12}$ alkoxy group, wherein, when A is a substituted aryl or heteroaryl group, a substituted $C_1$-$C_{12}$ alkyl group or a substituted, a substituent of A includes one of a cyano group, a halogen group, a trifluoromethyl group, a trifluoromethoxy group, hydrogen and deuterium;

wherein $C_1$ and $C_2$ are each independently one of hydrogen, deuterium, halogen group, or a cyano group; and wherein $D_1$ to $D_4$ are each independently connected by a single or double bond, and are substituted with one of halogen group, a cyano group, a malononitrile group, a trifluoromethyl group, and a trifluoromethoxy group, and at least two of $D_1$ to $D_4$ comprise a cyano group.

10. The light emitting device according to claim 7, wherein the next stack adjacent to the second blue stack with the charge generation unit interposed therebetween is a phosphorescent stack comprising at least a red phosphorescent light emitting layer.

11. The light emitting device according to claim 10, wherein the phosphorescent stack further comprises a green light emitting layer or a yellow/green light emitting layer that contacts the red phosphorescent light emitting layer.

12. The light emitting device according to claim 7, wherein the first charge generation layer comprises any one of an alkali metal, an alkaline earth metal, and a transition metal as a dopant in the electron-transporting host.

13. The light emitting device according to claim 10, wherein the next stack adjacent to the second blue stack with the charge generation unit interposed therebetween is a phosphorescent stack, and wherein the first blue stack is adjacent to the phosphorescent stack opposite the cathode, and the first hole transport layer of the first blue stack contacts the second charge generation layer.

14. The light emitting device according to claim 1, wherein the at least two stacks further comprise a second blue stack contacting the anode and a phosphorescent stack between the first blue stack and the second blue stack.

15. The light emitting device according to claim 14, wherein the second blue stack comprises a second electron transport layer, materials constituting the second electron transport layer being different from materials constituting the first electron transport layer.

16. The light emitting device according to claim 14, wherein the phosphorescent stack comprises a third hole transport layer, a red phosphorescent light emitting layer, a green phosphorescent light emitting layer, and a third electron transport layer.

17. The light emitting device according to claim 14, wherein the phosphorescent stack comprises a third hole transport layer, a red phosphorescent light emitting layer, a yellow-green phosphorescent light emitting layer, a green phosphorescent light emitting layer, and a third electron transport layer.

18. A light emitting display device comprising:

a substrate including a plurality of subpixels:

a thin film transistor provided in each of the plurality of subpixels on the substrate; and the light emitting device according to claim 1, the light emitting device connected to the thin film transistor.

* * * * *